US009957215B2

(12) United States Patent
Perez et al.

(10) Patent No.: US 9,957,215 B2
(45) Date of Patent: May 1, 2018

(54) PLANT EXTRACT COMPOSITIONS FOR FORMING PROTECTIVE COATINGS

(71) Applicant: aPEEL Technology, Inc., Goleta, CA (US)

(72) Inventors: Louis Perez, Santa Barbara, CA (US); Camille Mol, Santa Barbara, CA (US); Ronald C. Bakus, II, Santa Barbara, CA (US); James Rogers, Goleta, CA (US); Gabriel Rodriguez, Goleta, CA (US)

(73) Assignee: aPEEL Technology, Inc., Goleta, CA (US)

( * ) Notice: Subject to any disclaimer, the term of this patent is extended or adjusted under 35 U.S.C. 154(b) by 0 days. days.

(21) Appl. No.: 15/680,541

(22) Filed: Aug. 18, 2017

(65) Prior Publication Data

US 2018/0044276 A1 Feb. 15, 2018

Related U.S. Application Data

(63) Continuation of application No. PCT/US2016/065917, filed on Dec. 9, 2016.

(Continued)

(51) Int. Cl.
*C07C 51/09* (2006.01)
*C07C 51/36* (2006.01)
(Continued)

(52) U.S. Cl.
CPC ............ *C07C 51/09* (2013.01); *A23B 7/16* (2013.01); *A23L 3/3454* (2013.01); *C07C 51/36* (2013.01);
(Continued)

(58) Field of Classification Search
CPC ......... C07C 51/09; C07C 51/36; C07C 67/08; C08G 63/00; C08G 63/06; C09D 5/00; C09D 167/00; C09D 167/04
See application file for complete search history.

(56) References Cited

U.S. PATENT DOCUMENTS 2,213,557 A 9/1940 Tisdale
2,324,448 A 7/1943 Gottlieb
(Continued)

FOREIGN PATENT DOCUMENTS

DE 2505428 8/1976
DE 3622191 1/1988
(Continued)

OTHER PUBLICATIONS

Graca, J. et al., Linear and branched poly (omega-hydroxyacid) esters in plant cutins, 2010, J. Agric. Food Chem., vol. 58, No. 17, pp. 9666-9674 (Year: 2010).*

(Continued)

*Primary Examiner* — Yate K Cutliff
(74) *Attorney, Agent, or Firm* — Fenwick & West LLP

(57) ABSTRACT

Described herein are methods of preparing cutin-derived monomers, oligomers, or combinations thereof from cutin-containing plant matter. The methods can include heating the cutin-derived plant matter in a solvent at elevated temperature and pressure. In some preferred embodiments, the methods can be carried out without the use of additional acidic or basic species.

30 Claims, 39 Drawing Sheets

Related U.S. Application Data

(60) Provisional application No. 62/265,726, filed on Dec. 10, 2015.

(51) Int. Cl.

| | | |
|---|---|---|
| *C07C 67/08* | (2006.01) | |
| *C08G 63/06* | (2006.01) | |
| *C08G 63/00* | (2006.01) | |
| *C09D 167/00* | (2006.01) | |
| *C09D 167/04* | (2006.01) | |
| *A23B 7/16* | (2006.01) | |
| *A23L 3/3454* | (2006.01) | |
| *C09D 5/00* | (2006.01) | |

(52) U.S. Cl.
CPC .............. *C07C 67/08* (2013.01); *C08G 63/00* (2013.01); *C08G 63/06* (2013.01); *C09D 5/00* (2013.01); *C09D 167/00* (2013.01); *C09D 167/04* (2013.01); *A23V 2002/00* (2013.01)

(56) References Cited

U.S. PATENT DOCUMENTS

| | | | |
|---|---|---|---|
| 3,232,765 | A | 2/1966 | Rosenthal et al. |
| 3,997,674 | A | 12/1976 | Ukai |
| 4,002,775 | A | 1/1977 | Kabara |
| 4,421,775 | A | 12/1983 | Chan, Jr. |
| 4,423,071 | A | 12/1983 | Chignac et al. |
| 4,654,370 | A | 3/1987 | Marriott, III et al. |
| 4,661,359 | A | 4/1987 | Seaborne |
| 4,710,228 | A | 12/1987 | Seaborne et al. |
| 4,732,708 | A * | 3/1988 | Ekman .................... C07C 51/09 554/138 |
| 5,051,448 | A | 9/1991 | Shashoua |
| 5,110,509 | A | 5/1992 | Peter et al. |
| 2,363,232 | A | 11/1994 | Witt |
| 5,376,391 | A | 12/1994 | Nisperos |
| 5,607,970 | A | 3/1997 | Ishihara et al. |
| 5,658,768 | A | 8/1997 | Quinlan |
| 5,827,553 | A | 10/1998 | Dimitroglou et al. |
| 5,832,527 | A | 11/1998 | Kawaguchi |
| 5,906,831 | A | 5/1999 | Larsson et al. |
| 5,925,395 | A | 7/1999 | Chen |
| 5,939,117 | A | 8/1999 | Chen et al. |
| 6,165,529 | A | 12/2000 | Yang |
| 6,241,971 | B1 | 6/2001 | Fox et al. |
| 6,254,645 | B1 | 7/2001 | Kellis, Jr. et al. |
| 6,255,451 | B1 | 7/2001 | Koch et al. |
| 6,294,186 | B1 | 9/2001 | Beerse et al. |
| 6,348,217 | B1 | 2/2002 | Santos et al. |
| 6,503,492 | B2 | 1/2003 | McGlone et al. |
| 7,375,135 | B2 | 5/2008 | Najib-Fruchart et al. |
| 7,550,617 | B2 | 6/2009 | Imig et al. |
| 7,732,470 | B2 | 6/2010 | Imig et al. |
| 7,785,897 | B2 | 8/2010 | Agnes et al. |
| 7,851,002 | B2 | 12/2010 | Hekal et al. |
| 7,931,926 | B2 | 4/2011 | Lidster et al. |
| 7,943,336 | B2 | 5/2011 | Viksoe-Nielsen et al. |
| 8,101,221 | B2 | 1/2012 | Chen et al. |
| 8,119,178 | B2 | 2/2012 | Lidster et al. |
| 8,197,870 | B2 | 6/2012 | Krasutsky et al. |
| 8,247,609 | B2 | 8/2012 | Roques et al. |
| 8,263,751 | B2 | 9/2012 | Peterson |
| 8,424,243 | B1 | 4/2013 | Narciso et al. |
| 8,501,445 | B2 | 8/2013 | Yoshikawa et al. |
| 8,546,115 | B2 | 10/2013 | Buchert et al. |
| 8,609,169 | B2 | 12/2013 | Chen et al. |
| 8,752,328 | B2 | 6/2014 | Kaiser et al. |
| 8,846,355 | B2 | 9/2014 | Yoshikawa et al. |
| 9,095,152 | B2 | 8/2015 | Munger |
| 9,102,125 | B2 | 8/2015 | Battersby et al. |
| 9,284,432 | B2 | 3/2016 | Yoshikawa et al. |
| 9,770,041 | B2 | 9/2017 | Dong et al. |
| 2001/0042341 | A1 | 11/2001 | Hamersky et al. |
| 2002/0043577 | A1 | 4/2002 | Krasutsky et al. |
| 2004/0120919 | A1 | 6/2004 | Nguyen et al. |
| 2004/0220283 | A1 | 11/2004 | Zhang et al. |
| 2005/0233039 | A1 | 10/2005 | Wolfe et al. |
| 2008/0026120 | A1 | 1/2008 | Petcavich |
| 2008/0038471 | A1 | 2/2008 | Boger et al. |
| 2008/0254987 | A1 | 10/2008 | Liu et al. |
| 2008/0262190 | A1 | 10/2008 | Koskimies et al. |
| 2008/0310991 | A1 | 12/2008 | Webster et al. |
| 2009/0104446 | A1 | 4/2009 | Guillet et al. |
| 2009/0142453 | A1 | 6/2009 | Lobisser et al. |
| 2009/0325240 | A1 | 12/2009 | Daniell |
| 2010/0029778 | A1 | 2/2010 | Bailey et al. |
| 2010/0278784 | A1 | 11/2010 | Pojasek et al. |
| 2011/0244095 | A1 | 10/2011 | Sardo |
| 2011/0280942 | A1 | 11/2011 | Schad et al. |
| 2012/0251675 | A1 | 10/2012 | Sowa et al. |
| 2013/0209617 | A1 | 8/2013 | Lobisser et al. |
| 2013/0216488 | A1 | 8/2013 | Hernandez-Brenes et al. |
| 2014/0033926 | A1 | 2/2014 | Fassel et al. |
| 2014/0199449 | A1 | 7/2014 | Hernandez et al. |
| 2014/0205722 | A1 | 7/2014 | Quintanar Guerrero et al. |
| 2014/0221308 | A1 | 8/2014 | Baker et al. |
| 2014/0234921 | A1 | 8/2014 | Nyyssola et al. |
| 2014/0348945 | A1 | 11/2014 | Dong et al. |
| 2015/0030780 | A1 | 1/2015 | Rogers |
| 2015/0079248 | A1 | 3/2015 | Nussinovitch et al. |
| 2016/0002483 | A1 | 1/2016 | Zhao et al. |
| 2016/0213030 | A1 | 7/2016 | Schad |
| 2016/0256429 | A1 | 9/2016 | Spanova et al. |
| 2016/0324172 | A1 | 11/2016 | Williams et al. |
| 2017/0049119 | A1 | 2/2017 | Perez et al. |
| 2017/0073532 | A1 | 3/2017 | Perez et al. |
| 2017/0332650 | A1 | 11/2017 | Holland |

FOREIGN PATENT DOCUMENTS

| | | | |
|---|---|---|---|
| EP | 0104043 | 3/1984 | |
| JP | 62-126931 | 6/1987 | |
| WO | WO 93/06735 | 4/1993 | |
| WO | WO 2001/001980 | 1/2001 | |
| WO | WO 2004/030455 | 4/2004 | |
| WO | WO 2009/119730 | 10/2009 | |
| WO | WO 2012/042404 | 4/2012 | |
| WO | WO-2015028299 A1 * | 3/2015 | .............. A61K 36/81 |
| WO | WO 2015/052433 | 4/2015 | |
| WO | WO 2015/176020 | 11/2015 | |
| WO | WO 2016/168319 | 10/2016 | |
| WO | WO 2016/187581 | 11/2016 | |
| WO | WO 2017/048951 | 3/2017 | |
| WO | WO 2017/100636 | 6/2017 | |
| WO | WO 2017/132281 | 8/2017 | |

OTHER PUBLICATIONS

Kolattukudy, P.E. Cutin from plants, online 3a 2005, Biopolymers, 40 pages (Year: 2005).*

Matic, M., The chemistry of Plant Cuticles: a study of cutin form *Agave americana* L.,1956, Biochemical Journal, vol. 63, No. 1, pp. 168-176 (Year: 1956).*

Osman, S. F., et al., Preparation , Isolation, and Characterization of Cutin Monomers and oligomers from Tomato Peels, 1999, J. Agric, Food Chem, vol. 47, No. 2, pp. 799-802. (Year: 1999).*

Alvaro, J. et al. "Effects of peracetic acid disinfectant on the postharvest of some fresh vegetables", Journal of Food Engineering, 2009, vol. 95, pp. 11-15.

Andrade, Ricardo D. et al.: "Atomizing spray systems for application of edible coatings", Comprehensive Reviews in Food Science and Food Safety, vol. 11, No. 3, Apr. 9, 2012, pp. 323-337.

Ayala-Zavala, J.F., et al., "High Relative Humidity In-Package of Fresh-Cut Fruits and Vegetables: Advantage or Disadvantage Considering Microbiological Problems and Antimicrobial Delivering Systems?" J. Food Science, 2008, vol. 73, pp. R41-R47.

Ben-Yehoshua, S., et al. "Modified-atmosphere packaging of fruits and vegetables: reducing condensation of water in bell peppers and mangoes", Acta Hort (ISHS), 1998, vol. 464, pp. 387-92.

(56) References Cited

OTHER PUBLICATIONS

Bewick, T., et al. "Evaluation of Epicuticular Wax Removal from Whole Leaves with Chloroform," Weed Technology, Jul. - SePages, 1993, vol. 7, No. 3, pp. 706-716.
Bourtoom, T., "Edible films and coatings: characteristics and properties", International Food Research Journal, 2008, vol. 15, No. 3, pp. 237-248.
Cantwell, M., "Properties and recommended conditions for long-term storage of fresh fruits and vegetables," Nov. 2001, 8 Pages.
Cochran, H.D. "Solvation in supercritical water", Fluid Phase Equilibria, 1992, vol. 71, Pages 1-16.
DeEll, J.R., et al. "Addition of sorbitol with KMnO4 improves broccoli quality retention in modified atmosphere packages", 2006, J Food Qual, vol. 29, Pages 65-75.
Elgimabi, M.N., et al., "Effects of Bactericides and Sucrose-Pulsing on Vase Life of Rose Cut Flowers (Rosa hybirida)", Botany Research International, 2009, vol. 2, No. 3, pp. 164-168.
Gabler, M., et al. "Impact of Postharvest Hot Water or Ethanol Treatment of Table Grapes on Gray Mold Incidence, Quality, and Ethanol Content," Plant Disease, Mar. 2005, vol. 89, No. 3, pp. 309-316.
Gil, M. et al. "Fresh-cut product sanitation and wash water disinfection: Problems and solutions", International Journal of Food Microbiology, 2009, vol. 134, pp. 37-45.
Hardenburg, R., et al., "The Commercial Storage of Fruits, Vegetables, and Florist and Nursery Stocks," United States Department of Agriculture, Agriculture Handbook No. 66, Sep. 1986, pp. 6-7, 30, 50-51.
Hauff, S. et al. "Determination of hydroxylated fatty acids from the biopolymer of tomato cutin and their fate during incubation in soil," Phytochemical Analysis, Aug. 26, 2010, vol. 21, No. 6, pp. 582-589.
He, S., et al. "Stem end blockage in cut Grevillea 'Crimson Yul-lo' inflorescences", Postharvest Biology and Technology, 2006, vol. 41, pp. 78-84.
Hojjati, Y., et al. "Chemical Treatments of Eustoma Cut Flower Cultivars for Enhanced Vase Life", Journal of Agriculture and Social Sciences, 2007, vol. 3, No. 3, pp. 75-78.
Holcroft, D., "Water Relations in Harvested Fresh Produce," PEF White Paper No. 15-01, The Postharvest Education Foundation (PEF), May 2015, 16 Pages.
Javad, N., et al. "Postharvest evaluation of vase life, stem bending and screening of cultivars of cut gerbera (Gerbera jamesonii Bolux ex. Hook f.) flowers", African Journal of Biotechnology, Jan. 24, 2011, vol. 10, No. 4, pp. 560-566.
Javad, N., et al. "Effect of Cultivar on Water Relations and Postharvest Quality ofGerbera (Gerbera jamesonii Bolus ex. Hook f.) Cut Flower", World Applied Sciences Journal, 2012, vol. 18, No. 5, pp. 698-703.
Jones, R., et al. "Pulsing with Triton X-100 Improves Hydration and Vase Life of Cut Sunflowers (Helianthus annuus L.)", HortScience, 1993, vol. 28, No. 12, pp. 1178-1179.
Karabulut, 0. et al. "Postharvest ethanol and hot water treatments of table grapes to control gray mold", Postharvest Biology and Technology, 2004, vol. 34, pp. 169-177.
Krammer, P., et al. "Hydrolysis of esters in subcritical and supercritical water", Journal of Supercritical Fluids, 2000, vol. 16, pp. 189-206.
Loppinet-Serani, A. et al. "Supercritical water for environmental technologies", J Chem Technol Biotechnol, Jan. 12, 2010, vol. 85, pp. 583-589.
Morton, H. "The Relationship of Concentration and Germicidal Efficiency of Ethyl Alcohol", Annals New York Academy of Sciences, 53(1), 1950, pp. 191-196.

Oh, D. et al. "Antimicrobial activity of ethanol, glycerol monolaurate or lactic acid against Listeria monocytogenes", International Journal of Food Microbiology, 1993, vol. 20, pp. 239-246.
Olmez, H. et al. "Potential alternative disinfection methods for organic fresh-cut industry for minimizing water consumption and environmental impact", LWT—Food Science and Technology, 2009, vol. 42, pp. 686-693.
Roy, S., et al. "Modified atmosphere and modified humidity packaging of fresh mushrooms" J Food Sci., 1996, vol. 61, pp. 391-7.
Rutala, W. et al. "Guideline for Disinfection and Sterilization in Healthcare Facilities, 2008" CDC, 2008, 158 Pages.
Sasaki, M., et al. "Cellulose hydrolysis in subcritical and supercritical water", Journal of Supercritical Fluids, 1998, vol. 13, pp. 261-268.
Sasaki, M., et al. "Dissolution and Hydrolysis of Cellulose in Subcritical and Supercritical Water", Ind. Eng. Chem. Res., 2000, vol. 39, pp. 2883-2890.
Savage, P., "Organic Chemical Reactions in Supercritical Water", Chem. Rev., 1999, vol. 99, pp. 603-621.
Schreiber, L., "Transport barriers made of cutin, suberin and associated waxes", Trends in Plant Science, 2010, vol. 15, No. 10, pp. 546-553.
Schweizer, P., et al. "Perception of free cutin monomers by plant cells", The Plant Journal, 1996, vol. 10, No. 2, pp. 331-341.
Schweizer, P., et al. "Plant Protection by Free Cutin Monomers in Two Cereal Pathosystems", Advances in Molecular Genetics of Plant-Microbe Interactions, 1994, pp. 371-374.
Shirazi, A., et al. "Controlling relative humidity in modified atmosphere packages of tomato fruit", HortScience, 1992, vol. 27, pp. 336-9.
Steuter, A., et al. "Water Potential of Aqueous Polyethylene Glycol", Plant Physiol., 1981, vol. 67, pp. 64-67.
Van Doorn, W.G., et al. "Effects of surfactants on the longevity of dry-stored cut towering stems of rose, Bouvardia, and Astilbe", Postharvest Biology and Technology, 1993, vol. 3, pp. 69-76.
Van Doorn, W.G., et al. "Alkylethoxylate surfactants for rehydration of roses and Bouvardia flowers", Postharvest Biology and Technology, 2002, vol. 24, pp. 327-333.
Van Meeteren, U., "Water Relations and Keeping-Quality of Cut Gerbera Flowers. I. The Cause of Stem Break", Scientia Horticulturae, 1978, vol. 8, pp. 65-74.
Weingartner, H., et al. "Supercritical water as a solvent", Angewandte Chemie, 2005, vol. 44, Issue 18, pp. 2672-2692.
Yeats, T., et al. "The identification of cutin synthase: formation of the plant polyester cutin," Nat Chem Biol. Jul. 2012, vol. 8, No. 7, pp. 609-611.
PCT International Search Report and Written Opinion for PCT/US2016/065917, dated Mar. 9, 2017, 10 Pages.
PCT International Search Report and Written Opinion for PCT/US2017/014978, dated Apr. 10, 2017, 13 Pages.
Jerome, F., et al. ""One pot" and selective synthesis of monoglycerides over homogeneous and heterogeneous guanidine catalysts" Green Chem., 2004, vol. 6, pp. 72-74.
Mattson, F.H., et al., "Synthesis and properties of glycerides," J Lipid Research, Jul. 1962, vol. 3, No. 3, pp. 281-296.
Tanaka, M., et al., "Quantitative determination of isomeric glycerides, free fatty acids and triglycerides by thin layer chromatography-flame ionization detector system." Lipids, 1980, vol. 15, No. 10, pp. 872-875.
PCT International Search Report and Written Opinion for PCT/US2016/051936, dated Jan. 31, 2017, 18 Pages.

\* cited by examiner

| Temperature (K) | Time (hours) | Heptane Precipitate Products | Heptane Supernatant Products | Ethyl Acetate Supernatant Products |
|---|---|---|---|---|
| 498 | 1 | -- | -- | -- |
| | 2 | Sat | -- | -- |
| | 4 | ↓ | -- | Sat |
| | 8 | ↓ | Unsat | ↓ |
| 523 | 1 | ↓ | ↑ | ↓ |
| | 2 | Sat+Unsat | ↑ | ↓ |
| | 4 | ↓ | ↑ | ↓ |
| 548 | 1 | ↓ | ↑ | ↓ |
| | 2 | ↓ | ↑ | ↓ |
| | 4 | Unsat | ↓ | -- |

FIG. 13

| Temperature (K) | Time (hours) | Heptane Precipitate Products | Heptane Supernatant Products |
|---|---|---|---|
| 498 | 1 | -- | -- |
| | 2 | Sat | -- |
| | 4 | | -- |
| 523 | 1 | | -- |
| | 2 | | -- |
| | 4 | | Unsat |
| 548 | 1 | | |
| | 2 | | |
| | 4 | | |
| 573 | 1 | | |
| | 2 | | |
| | 4 | ↓ | ↓ |

FIG. 15

Chemical Formula: $C_{18}H_{36}NaO_4^+$
m/z: 339.2506 (100.0%), 340.2539 (19.5%), 341.2573 (1.8%)

Chemical Formula: $C_{18}H_{34}NaO_3^+$
m/z: 321.2400 (100.0%), 322.2434 (19.5%), 323.2467 (1.8%)

PLANT EXTRACT COMPOSITIONS FOR FORMING PROTECTIVE COATINGS

CROSS REFERENCE TO RELATED APPLICATIONS

This application is a continuation of PCT/US2016/065917, filed Dec. 9, 2016, which claims the benefit of priority to U.S. Provisional Patent Application Ser. No. 62/265,726, filed Dec. 10, 2015, the contents of each of which are incorporated by reference in their entirety.

TECHNICAL FIELD

The present disclosure relates to plant extract compositions and methods of isolating plant-derived monomers, oligomers, and mixtures thereof for applications in agricultural coating formulations.

BACKGROUND

Common agricultural products are susceptible to degradation and decomposition (i.e., spoilage) when exposed to the environment. Such agricultural products can include, for example, eggs, fruits, vegetables, produce, seeds, nuts, flowers, and/or whole plants (including their processed and semi-processed forms). Non-agricultural products (e.g., vitamins, candy, etc.) are also vulnerable to degradation when exposed to the ambient environment. The degradation of the agricultural products can occur via abiotic means as a result of evaporative moisture loss from an external surface of the agricultural products to the atmosphere and/or oxidation by oxygen that diffuses into the agricultural products from the environment and/or mechanical damage to the surface and/or light-induced degradation (i.e., photodegradation). Furthermore, biotic stressors such as, for example, bacteria, fungi, viruses, and/or pests can also infest and decompose the agricultural products.

Conventional approaches to preventing degradation, maintaining quality, and increasing the life of agricultural products include refrigeration and/or special packaging. Refrigeration requires capital-intensive equipment, demands constant energy expenditure, can cause damage or quality loss to the product if not carefully controlled, must be actively managed, and its benefits are lost upon interruption of a temperature-controlled supply chain. Special packaging can also require expensive equipment, consume packaging material, increase transportation costs, and require active management. Despite the benefits that can be afforded by refrigeration and special packaging, the handling and transportation of the agricultural products can cause surface abrasion or bruising that is aesthetically displeasing to the consumer and serves as points of ingress for bacteria and fungi. Moreover, the expenses associated with such approaches can add to the cost of the agricultural product.

The cells that form the aerial surface of most plants (such as higher plants) include an outer envelope or cuticle, which provides varying degrees of protection against water loss, oxidation, mechanical damage, photodegradation, and/or biotic stressors, depending upon the plant species and the plant organ (e.g., fruit, seeds, bark, flowers, leaves, stems, etc.). Cutin, which is a biopolyester derived from cellular lipids, forms the major structural component of the cuticle and serves to provide protection to the plant against environmental stressors (both abiotic and biotic). The thickness, density, as well as the composition of the cutin (i.e., the different types of monomers that form the cutin and their relative proportions) can vary by plant species, by plant organ within the same or different plant species, and by stage of plant maturity. The cutin-containing portion of the plant can also contain additional compounds (e.g., epicuticular waxes, phenolics, antioxidants, colored compounds, proteins, polysaccharides, etc.). This variation in the cutin composition as well as the thickness and density of the cutin layer between plant species and/or plant organs and/or a given plant at different stages of maturation can lead to varying degrees of resistance between plant species or plant organs to attack by environmental stressors (i.e., water loss, oxidation, mechanical injury, and light) and/or biotic stressors (e.g., fungi, bacteria, viruses, insects, etc.).

SUMMARY

Described herein are methods of preparing cutin-derived monomers, oligomers, or combinations thereof from cutin-containing plant matter. The method can comprise heating the cutin-containing plant matter in a solvent at elevated temperature and pressure.

Accordingly, in one aspect, the present disclosure provides a method of preparing cutin-derived monomers, oligomers, or combinations thereof from cutin-containing plant matter, comprising:
obtaining cutin from the cutin-containing plant matter;
adding the cutin to a solvent to form a first mixture, the solvent having a boiling point at a first temperature at a pressure of one atmosphere; and
heating the first mixture to a second temperature and second pressure, the second temperature being higher than the first temperature and the second pressure being higher than one atmosphere, to form a second mixture comprising the cutin-derived monomers, oligomers, or combinations thereof.

In another aspect, the present disclosure provides a method of forming a plant extract composition, comprising:
obtaining cutin from cutin-containing plant matter;
adding the cutin to a first solvent to form a first mixture, the first solvent having a first boiling point at a first temperature at a pressure of one atmosphere;
heating the first mixture to a second temperature and second pressure, the second temperature being higher than the first temperature and the second pressure being higher than one atmosphere, to form a second mixture comprising cutin-derived monomers, oligomers, or combinations thereof;
separating the first solvent from the cutin-derived monomers, oligomers, or combinations thereof in the second mixture; and
dissolving the cutin-derived monomers, oligomers, or combinations thereof in a second solvent.

In another aspect, the present disclosure provides a method of forming a plant extract composition, comprising:
obtaining cutin from cutin-containing plant matter;
adding the cutin to a first solvent to form a first mixture, the first solvent having a boiling point at a first temperature and first pressure; and
heating the first mixture to a second temperature, the second temperature being higher than the first temperature, to form a second mixture comprising cutin-derived monomers, oligomers, or combinations thereof, wherein at least a portion of the cutin-derived monomers or oligomers in the second mixture are unsaturated.

In another aspect, the present disclosure provides a method of preparing cutin-derived monomers, oligomers, or combinations thereof from cutin-containing plant matter, comprising:

obtaining cutin from the cutin-containing plant matter;

adding the cutin to a solvent to form a first mixture, the solvent having a boiling point at a first temperature at a pressure of one atmosphere;

heating the first mixture to a second temperature and second pressure, the second temperature being higher than the first temperature and the second pressure being higher than one atmosphere, to form a second mixture comprising a first group of compounds of the Formula I:

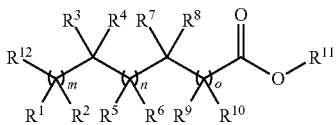

(Formula I)

wherein:

$R^1$, $R^2$, $R^3$, $R^4$, $R^5$, $R^6$, $R^7$, $R^8$, $R^9$, and $R^{10}$ are each independently —H, —$OR^{13}$, —$NR^{13}R^{14}$, —$SR^{13}$, halogen, —$C_1$-$C_6$ alkyl, —$C_1$-$C_6$ alkenyl, —$C_1$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{13}$, —$NR^{13}R^{14}$, —$SR^{13}$, or halogen;

$R^{13}$ and $R^{14}$ are each independently —H, —$C_1$-$C_6$ alkyl, —$C_1$-$C_6$ alkenyl, or —$C_1$-$C_6$ alkynyl;

$R^{11}$ is —H, -glyceryl, —$C_1$-$C_6$ alkyl, —$C_1$-$C_6$ alkenyl, —$C_1$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{13}$, —$NR^{13}R^{14}$, —$SR^{13}$, or halogen;

$R^{12}$ is —OH, —H, —$C_1$-$C_6$ alkyl, —$C_1$-$C_6$ alkenyl, —$C_1$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{13}$, —$NR^{13}R^{14}$, —$SR^{13}$, halogen, —COOH, or —$COOR^{11}$; and m, n, and o are each independently an integer in the range of 0 to 30, and $0 \leq m+n+o \leq 30$.

In another aspect, the present disclosure provides a method of preparing a composition comprising esters of cutin-derived fatty acids. The method includes obtaining cutin from cutin-containing plant matter, and adding the cutin to a solvent to form a mixture, the solvent having a boiling point at a first temperature at a pressure of one atmosphere. The method further includes heating the mixture to a second temperature and second pressure, the second temperature being higher than the first temperature and the second pressure being higher than one atmosphere, thereby forming the composition comprising the esters.

In another aspect, the present disclosure provides a method of preparing a composition comprising cutin-derived free fatty acid monomers, oligomers, or combinations thereof. The method includes obtaining cutin from cutin-containing plant matter, adding the cutin to water to form a mixture. The method further includes heating the mixture from a first temperature and first pressure to a second temperature and second pressure, the second temperature being higher than the boiling point of water at one atmosphere and the second pressure being higher than one atmosphere, thereby forming the composition comprising the cutin-derived free fatty acid monomers, oligomers, or combinations thereof.

In another aspect, the present disclosure provides a method of forming a protective coating. The method includes extracting a composition from a cuticle layer of a first plant species, the composition including a plurality of cutin-derived monomers, oligomers, or combinations thereof, and disposing the composition on a second plant species which is either the same or different from the first plant species to form the protective coating over the second plant species.

In another aspect, the present disclosure provides a method of forming a protective coating. The method includes extracting a composition from a cuticle layer of plant matter of a first plant, the composition including a plurality of cutin-derived free fatty acid monomers or oligomers, fatty acid esters, or combinations thereof, and disposing the composition on plant matter of a second plant different from the first plant, thereby forming the protective coating over the plant matter of the second plant.

In another aspect, the present disclosure provides a method of preparing cutin-derived monomers, oligomers, or combinations thereof from cutin-containing plant matter, comprising:

obtaining cutin from the cutin-containing plant matter;

adding the cutin to a solvent to form a first mixture, the solvent having a boiling point at a first temperature at a pressure of one atmosphere;

heating the first mixture to a second temperature and second pressure, the second temperature being higher than the first temperature and the second pressure being higher than one atmosphere, to form a second mixture comprising a first group of compounds of the Formula II:

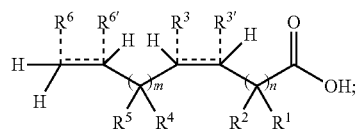

(Formula II)

wherein:

$R^1$, $R^2$, $R^4$ and $R^5$ are each independently —H, —$OR^{11}$, —$NR^{11}R^{12}$, —$SR^{11}$, halogen, —$C_1$-$C_6$ alkyl, —$C_1$-$C_6$ alkenyl, —$C_1$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{11}$, —$NR^{11}R^{12}$, —$SR^{11}$, or halogen;

$R^{11}$ and $R^{12}$ are each independently —H, —$C_1$-$C_6$ alkyl, —$C_1$-$C_6$ alkenyl, or —$C_1$-$C_6$ alkynyl;

the symbol ===== represents an optionally single or cis or trans double bond;

$R^3$ is —OH and $R^{3'}$ is selected from the group consisting of —H, —$C_1$-$C_6$ alkyl, —$C_1$-$C_6$ alkenyl, —$C_1$-$C_6$ alkynyl, —$C_3$-$C_7$ cycloalkyl, and aryl when ===== between $R^3$ and $R^{3'}$ is a single bond, and $R^3$ and $R^{3'}$ are absent when ===== between $R^3$ and $R^{3'}$ represents a double bond;

$R^6$ is —OH and $R^{6'}$ is selected from the group consisting of —H, —$C_1$-$C_6$ alkyl, —$C_1$-$C_6$ alkenyl, —$C_1$-$C_6$ alkynyl, —$C_3$-$C_7$ cycloalkyl, and aryl when ===== between $R^6$ and $R^{6'}$ is a single bond, and $R^6$ and $R^{6'}$ are absent when ===== between $R^6$ and $R^{6'}$ represents a double bond;

n is an integer in the range of 0 to 11;
m is an integer in the range of 0 to 25; and
0≤m+n≤25.

In another aspect, the present disclosure provides a method of preparing cutin-derived monomers, oligomers, or combinations thereof from cutin-containing plant matter, comprising:

obtaining cutin from the cutin-containing plant matter;
adding the cutin to a solvent to form a first mixture, the solvent having a boiling point at a first temperature at a pressure of one atmosphere;
heating the first mixture to a second temperature and second pressure, the second temperature being higher than the first temperature and the second pressure being higher than one atmosphere, to form a second mixture comprising a first group of compounds of the Formula III:

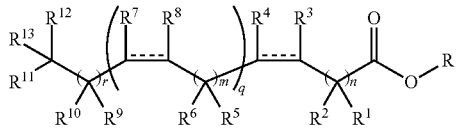

(Formula III)

wherein:
$R^1$, $R^2$, $R^5$, $R^6$, $R^9$, $R^{10}$, $R^{11}$, $R^{12}$ and $R^{13}$ are each independently, at each occurrence, —H, —OR$^{14}$, —NR$^{14}$R$^{15}$, —SR$^{14}$, halogen, —C$_1$-C$_6$ alkyl, —C$_2$-C$_6$ alkenyl, —C$_2$-C$_6$ alkynyl, —C$_3$-C$_7$ cycloalkyl, aryl, or heteroaryl, wherein each alkyl, alkenyl, alkynyl, cycloalkyl, aryl, or heteroaryl is optionally substituted with one or more —OR$^{14}$, —NR$^{14}$R$^{15}$, —SR$^{14}$, or halogen;

$R^3$, $R^4$, $R^7$, and $R^8$ are each independently, at each occurrence, —H, —OR$^{14}$, —NR$^{14}$R$^{15}$, —SR$^{14}$, halogen, —C$_1$-C$_6$ alkyl, —C$_2$-C$_6$ alkenyl, —C$_2$-C$_6$ alkenyl, —C$_2$-C$_6$ alkynyl, —C$_3$-C$_7$ cycloalkyl, aryl, or heteroaryl wherein each alkyl, alkynyl, cycloalkyl, aryl, or heteroaryl is optionally substituted with one or more —OR$^{14}$, —NR$^{14}$R$^{15}$, —SR$^{14}$, or halogen; or $R^3$ and $R^4$ can combine with the carbon atoms to which they are attached to form a C$_3$-C$_6$ cycloalkyl, a C$_4$-C$_6$ cycloalkenyl, or 3- to 6-membered ring heterocycle; and/or $R^7$ and $R^8$ can combine with the carbon atoms to which they are attached to form a C$_3$-C$_6$ cycloalkyl, a C$_4$-C$_6$ cycloalkenyl, or 3- to 6-membered ring heterocycle;

$R^{14}$ and $R^{15}$ are each independently, at each occurrence, —H, —C$_1$-C$_6$ alkyl, —C$_2$-C$_6$ alkenyl, or —C$_2$-C$_6$ alkynyl;
the symbol ===== represents a single bond or a cis or trans double bond;
n is 0, 1, 2, 3, 4, 5, 6, 7 or 8;
m is 0, 1, 2 or 3;
q is 0, 1, 2, 3, 4 or 5; and
r is 0, 1, 2, 3, 4, 5, 6, 7 or 8; and
R is selected from —H, —C$_1$-C$_6$ alkyl, —C$_2$-C$_6$ alkenyl, —C$_2$-C$_6$ alkynyl, —C$_3$-C$_7$ cycloalkyl, aryl, 1-glycerol, 2-glycerol, or heteroaryl.

Methods and formulations described herein can each include one or more of the following steps or features, either alone or in combination with one another. The second mixture can be cooled to a third temperature, the third temperature being lower than the second temperature. The step of cooling the second mixture can further comprise reducing the second pressure to a third pressure, the third pressure being below the second pressure. The third temperature can be lower than the first temperature. The third pressure can be substantially the same as the first pressure. The third pressure can be about one atmosphere. The method can further comprise separating the solvent from the second mixture to isolate the cutin-derived monomers, oligomers, or combinations thereof. The second temperature can be at least 5% higher than the first temperature. The second pressure can be sufficiently high to maintain at least a portion of the solvent in a liquid phase at the second temperature. The second pressure can be higher than the first pressure. The cutin can be at least partially separated from a non-cutin containing portion of the plant matter prior to adding the cutin to the solvent.

The process of forming the second mixture can further result in the production of unsaturated fatty acids. The process of forming the second mixture can result in the production of both saturated and unsaturated fatty acids. The production of unsaturated fatty acids can be the result of elimination of a hydroxy group bound to the fatty acid chain. A concentration of saturated fatty acids can be substantially higher than a concentration of unsaturated fatty acids in the second mixture. The process of forming the second mixture can further result in the production of unsaturated fatty acids. The process of forming the second mixture can result in the production of both saturated and unsaturated fatty acid esters. The production of unsaturated fatty acid esters can be the result of elimination of a hydroxy group bound to the fatty acid chain. A concentration of saturated fatty acid esters can be substantially higher than a concentration of unsaturated fatty acid esters in the second mixture.

The heating of the first mixture can be performed while the first mixture is in a vessel, and the method can further comprise injecting a gas or liquid into the vessel during the heating of the first mixture. A depolymerization reaction at the second temperature can result in uncharged cutin-derived monomers, oligomers, or combinations thereof. The solvent can be selected such that concentrations of reactive anions and reactive cations dispersed therein while the solvent is held at the second temperature are sufficient to at least partially depolymerize the cutin and to result in uncharged cutin-derived monomers, oligomers, or combinations thereof. A rate of depolymerization of the cutin in the solvent can be at least 100 times greater at the second temperature and the second pressure than at the first temperature at a pressure of one atmosphere. The cutin-derived monomers, oligomers, or combinations thereof in the second mixture can be substantially soluble in the solvent at about 298 K. The second temperature can be greater than about 393 K. The second temperature can be at least about 498 K. The solvent can be selected from the group consisting of water, glycerol, methanol, ethanol, liquid CO$_2$, and supercritical CO$_2$, or a combination thereof. The solvent can be a nucleophilic solvent. The solvent can be water. The first mixture can further include a co-solvent. The co-solvent can comprise CO$_2$. The solvent can be substantially free of added acid or base.

The second temperature can be at least about 498K and the second pressure can be at least about 360 psi, and the first mixture can be held at the second temperature and second pressure for at least about eight hours. The second temperature can be at least about 523K and the second pressure can be at least about 575 psi, and the first mixture can be held at the second temperature and second pressure for at least about two hours. The first mixture can further include a reactive additive. The reactive additive can be an enzyme, NaOH, Na$_2$CO$_3$, acetic acid, a pH modifier, or a combination thereof.

The cutin can be at least partially separated from a non-cutin containing portion of the plant matter prior to adding the cutin to the first solvent. The cutin-derived monomers, oligomers, or combinations thereof in the second mixture can be filtered from non-depolymerized residue and separated from the first solvent. At least a portion of the cutin-derived monomers, oligomers or combinations thereof can be unsaturated fatty acids. The method can further comprise hydrogenating the unsaturated fatty acids before adding them to the second solvent. The unsaturated fatty acids can be dissolved in the second solvent without hydrogenation. At least a portion of the cutin-derived monomers, oligomers or combinations thereof can be unsaturated fatty acid esters. The method can further comprise hydrogenating the unsaturated fatty acid esters before adding them to the second solvent. The unsaturated fatty acid esters can be dissolved in the second solvent without hydrogenation.

The method can further comprise separating the first solvent from the cutin-derived monomers, oligomers, or combinations thereof in the second mixture, and hydrogenating the unsaturated cutin-derived monomers and oligomers to form a third mixture comprising cutin-derived monomers, oligomers, or combinations thereof, wherein substantially all of the cutin-derived monomers or oligomers in the third mixture are saturated. The unsaturated cutin-derived monomers and oligomers in the second mixture can be separated from saturated cutin-derived monomers and oligomers in the second mixture prior to hydrogenation. In some embodiments, the unsaturated cutin-derived monomers and oligomers in the second mixture are not separated from saturated cutin-derived monomers and oligomers in the second mixture prior to hydrogenation. Between about 10% and 98% of the cutin-derived monomers and oligomers in the second mixture can be unsaturated. Between 0.5% and 30%, greater than 0% but less than 40%, less than 10%, between about 1% and 98%, between 1% and 99%, or substantially all of the cutin-derived monomers and oligomers in the second mixture can be unsaturated. The method can further comprise dissolving the third mixture in a second solvent.

The method can further produce compounds of the Formula II:

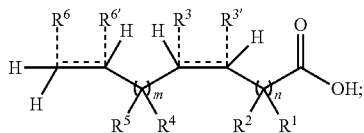

(Formula II)

wherein:

$R^1$, $R^2$, $R^4$ and $R^5$ are each independently —H, —$OR^{11}$, —$NR^{11}R^{12}$, —$SR^{11}$, halogen, —$C_1$-$C_6$ alkyl, —$C_1$-$C_6$ alkenyl, —$C_1$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{11}$, —$NR^{11}R^{12}$, —$SR^{11}$, or halogen;

$R^{11}$ and $R^{12}$ are each independently —H, —$C_1$-$C_6$ alkyl, —$C_1$-$C_6$ alkenyl, or —$C_1$-$C_6$ alkynyl;

the symbol ===== represents an optionally single or cis or trans double bond;

$R^3$ is —OH and $R^{3'}$ is selected from the group consisting of —H, —$C_1$-$C_6$ alkyl, —$C_1$-$C_6$ alkenyl, —$C_1$-$C_6$ alkynyl, —$C_3$-$C_7$ cycloalkyl, and aryl when ===== between $R^3$ and $R^{3'}$ is a single bond, and $R^3$ and $R^{3'}$ are absent when ===== between $R^3$ and $R^{3'}$ represents a double bond;

$R^6$ is —OH and $R^{6'}$ is selected from the group consisting of —H, —$C_1$-$C_6$ alkyl, —$C_1$-$C_6$ alkenyl, —$C_1$-$C_6$ alkynyl, —$C_3$-$C_7$ cycloalkyl, and aryl when ===== between $R^6$ and $R^{6'}$ is a single bond, and $R^6$ and $R^{6'}$ are absent when ===== between $R^6$ and $R^{6'}$ represents a double bond;

n is an integer in the range of 0 to 11;

m is an integer in the range of 0 to 25; and

0≤m+n≤25.

The method can further produce a second group of compounds of the Formula I, the second group of compounds of Formula I being different from the first group of compounds of the Formula I. The method can produce compounds of Formula II that can then be transformed into compounds of Formula I, for example through conventional synthetic transformation, wherein the compounds of Formula I that are thereby formed may differ from compounds of Formula I produced directly by thermal depolymerization. For instance, an acid formed by a hydrothermal depolymerization method as set forth herein can be subsequently converted to an ester. The forming of the protective coating can comprise causing at least some of the cutin-derived monomers, oligomers, or combinations thereof to cross-link on the second plant species. The method can further include chemically modifying the cutin-derived monomers, oligomers, or combinations thereof prior to disposing the composition on the second plant species. Chemically modifying the cutin-derived monomers, oligomers, or combinations thereof can comprise glycerating the cutin-derived monomers, oligomers, or combinations thereof (e.g., forming a glycerol ester of the corresponding fatty acid or ester). A chemical composition of the protective coating can be different from a chemical composition of a cuticle layer of the second plant species. The extracting of the composition from the cuticle layer of the first plant species can comprise obtaining cutin from the cuticle layer of the first plant species, adding the cutin to a solvent to form a first mixture, the solvent having a boiling point at a first temperature at a pressure of one atmosphere, and heating the first mixture to a second temperature and second pressure, the second temperature being higher than the first temperature and the second pressure being higher than one atmosphere, to form a second mixture comprising the cutin-derived monomers, oligomers, or combinations thereof. The method can further comprise modifying the compounds of Formula II to form compounds of Formula I, where Formula II and Formula I are as previously described. The method can further comprise modifying the compounds of Formula III to form compounds of Formula I, where Formula III and Formula I are as previously described.

The solvent in which the cutin is added can comprise ethanol, and the esters of the resulting composition can comprise ethyl esters. The solvent in which the cutin is added can comprise methanol, and the esters of the resulting composition can comprise methyl esters. The solvent in which the cutin is added can comprise glycerol, and the esters of the resulting composition can comprise glyceryl esters.

As used herein, the term "substrate" refers to any object or material over which a coating is formed or material is deposited. In particular implementations, the substrate is edible to humans, and the coating is an edible coating. Examples of edible substrates include agricultural products and foods such as fruits, vegetables, produce, seeds, nuts, beef, poultry, and seafood. Although the coatings can be formed over the entire outer surface of the substrate, in some implementations the coatings can cover a portion of the outer surface of the substrate. The coatings can also include apertures or porous regions which expose a portion of the outer surface of the substrate.

As used herein, "plant matter" refers to any portion of a plant, for example, fruits (in the botanical sense, including fruit peels and juice sacs), leaves, stems, barks, seeds, flowers, or any other portion of the plant.

BRIEF DESCRIPTION OF THE DRAWINGS

FIG. 13 is a table indicating the nature of products isolated after soxhlet extraction using heptane and ethyl acetate after thermal hydrolysis in water at various temperatures and reaction durations.

FIG. 15 is a table indicating which products were recovered from the heptane precipitate and from the heptane supernatant at various depolymerization temperatures and residence times for thermal depolymerization of cutin in ethanol.

Like reference symbols in the various figures indicate like elements.

DETAILED DESCRIPTION

Figure 1:
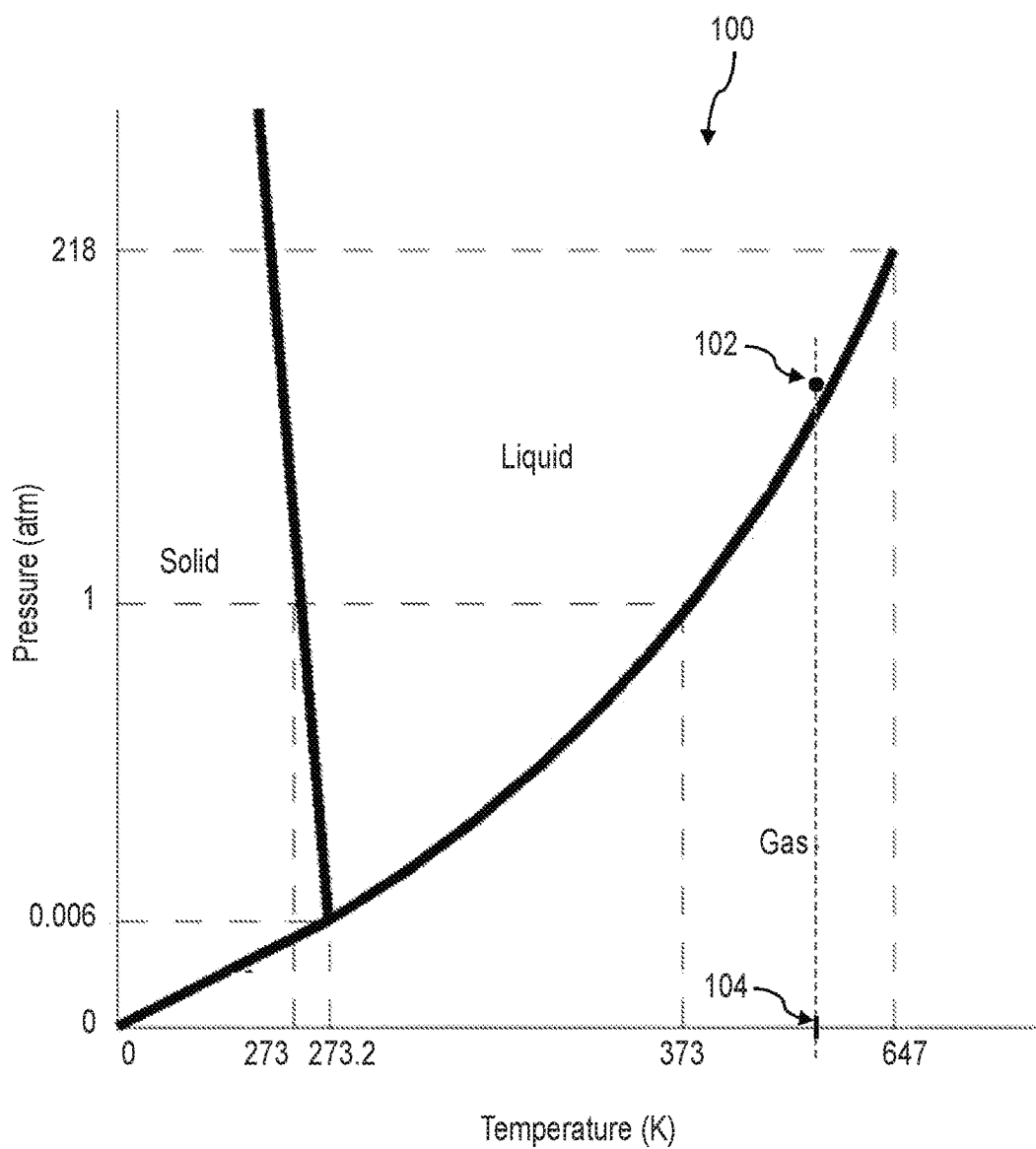
FIG. 1 is a phase diagram of $H_2O$.

The biopolyester cutin forms the main structural component of the cuticle that composes the aerial surface of most land plants and plays a significant role in providing plants a protective barrier against both abiotic and biotic stressors. The thickness, density, as well as the composition of the cutin (i.e., the different types of monomers that form the cutin and their relative proportions) can vary by plant species, by plant organ within the same or different plant species, and by stage of plant maturity. These variations can define the amount, degree, or quality of protection (and degree of plasticity) offered by the cutin layer to the plant or plant organ against environmental and/or biotic stressors. Cutin is formed from a mixture of polymerized mono- and/or polyhydroxy fatty acids and embedded cuticular waxes. The hydroxy fatty acids of the cuticle layer form tightly bound networks with high crosslink density, thereby acting as a barrier to moisture loss and oxidation, as well as providing protection against other environmental stressors.

Described herein are methods of preparing and forming plant extract compositions from plant matter. The plant extract compositions are formed from decomposition (e.g., depolymerization) of cutin or other crosslinked polymers (e.g., polyesters), and include hydroxy fatty acids and hydroxy fatty esters (as well as their oligomers and mixtures thereof) found in the cuticle layer or other crosslinked polymer network. The plant extract compositions can subsequently be applied to other plant or agricultural products in order to form a protective coating over the products, or to enhance or modify existing coatings (either naturally occurring or deposited coatings) which are on the outer surface of the products. The applied coatings can, for example, serve to protect the products from biotic stressors such as bacteria, fungi, viruses, and/or pests. The applied coatings can also (or alternatively) serve to increase the shelf life of produce without refrigeration, and/or to control the rate of ripening of produce. The methods of forming the plant extract compositions can result in the compositions being substantially free of other accompanying plant-derived compounds (e.g., proteins, polysaccharides, phenols, lignans, aromatic acids, terpenoids, flavonoids, carotenoids, alkaloids, alcohols, alkanes, and aldehydes), thereby improving the efficacy of the subsequently formed protective coatings.

As described above, the monomer and/or oligomer units of the plant extract compositions can be obtained from cutin found in plant matter. Plant matter typically includes some portions that contain cutin and/or have a high density of cutin (e.g., fruit peels, leaves, shoots, etc.), as well as other portions that do not contain cutin or have a low density of cutin (e.g., fruit flesh, seeds, etc.). The cutin-containing portions can be used to produce plant extract compositions comprising cutin-derived monomers and/or oligomers, and can also include other constituents such as proteins, polysaccharides, phenols, lignans, aromatic acids, terpenoids, flavonoids, carotenoids, alkaloids, alcohols, alkanes, and aldehydes. The low cutin density or non-cutin-containing portions can often lack the monomer and/or oligomer units, or otherwise include a much lower ratio of monomer and/or oligomer units to the other constituents as compared to the higher density cutin-containing portions.

Methods described herein for forming plant extract compositions can include first separating (or at least partially separating) cutin-containing portions of plant matter from non-cutin-containing portions, and obtaining cutin from the cutin-containing portions (e.g., when the cutin-containing portion is a fruit peel, the peel is separate from the fruit body, and/or the cutin is separated from the peel). The cutin, or peel containing cutin, is then depolymerized (or at least partially depolymerized) using a thermal process, described in detail below, in order to obtain a mixture including a plurality of fatty acid or esterified cutin-derived monomers, oligomers, or combinations thereof. The thermal process for depolymerization causes most of or substantially all of (e.g., at least 95% of) the resulting monomers and/or oligomers of the mixture to be protonated or rendered neutral (i.e., uncharged) without requiring any additional processes (e.g., acidification). In other words, the depolymerization processes described herein can be carried out in the absence of added base or acid. This results in the monomers and/or oligomers being in a state such that they can subsequently be chemically modified to provide compounds whose properties can be tailored for specific applications. For example, oxygen and water barrier properties of subsequently formed coatings can be controlled by chemically modifying the monomers and/or oligomers, and such modifications may require that the monomers and/or oligomers first be protonated or rendered neutral. Furthermore, the chemical modification of the monomers and/or oligomers can be tailored to change the solubility of the extract composition in order to allow for expanded options for coating deposition. Finally, the mixture including the free fatty acid and/or free fatty ester monomer and/or oligomer units is dissolved in another solvent to form a solution, thereby resulting in a plant extract composition suitable for coating applications (e.g., agricultural coating applications). Optionally, prior to forming the plant extract composition, the free fatty acid and/or free fatty ester monomer and/or oligomer units of the mixture are activated or modified (e.g., glycerated), for example to form a mixture of 1-monoacylglycerides and/or 2-monoacylglycerides, and the mixture of modified monomer and/or oligomer units (e.g., 1-monoacylglycerides and/or 2-monoacylglycerides) is dissolved in a solvent to form a solution, thereby resulting in the plant extract composition.

As described above, to form a cutin-derived plant extract composition suitable for coating applications, cutin-containing portions of plant matter are first separated (or at least partially separated) from non-cutin-containing portions. This can be achieved by a number of methods, either alone or in combination with one another. For example, the plant matter can be thermally and/or mechanically and/or enzymatically and/or chemically treated to at least partially separate the cutin-containing portion from the non-cutin-containing portion. Or, the plant matter can be subjected to elevated temperature and/or pressure in an aqueous medium (e.g., as in pressure cooking) to partially separate the cutin-containing portion from the non-cutin-containing portion of the plant matter. Alternatively, the plant matter may be subjected to lower temperatures (e.g., as in freezing) to partially separate the cutin-containing portion from the non-cutin-containing portion of the plant matter. The plant matter may also be subjected to sonication in an aqueous medium to partially separate the cutin-containing portion from the non-cutin-containing portion of the plant matter. Optionally, the cutin-containing portion can be heated in a mixture of ammonium oxalate and oxalic acid to aid separation of the cutin from the non-cutin-containing portion (i.e., the remainder of the cuticle and unwanted plant matter). Optionally, this separation can be achieved (or assisted) enzymatically using enzymes capable of hydrolyzing ester bonds and/or alternatively using enzymes capable of breaking down polysaccharides that comprise the non-cutin-containing portion of the plant. The cutin-containing portion can optionally be refluxed in at least one organic solvent (such as chloroform and/or methanol) to remove residual waxes and/or any remaining soluble components from the cutin. Alternatively, removal of residual waxes and remaining soluble components can be achieved using liquid or supercritical $CO_2$.

After separating (or at least partially separating) the cutin-containing portions of the plant matter from non-cutin-containing portions, the cutin (or cutin-containing component) obtained from the plant matter is then added to a solvent to form a first mixture. The solvent can, for example, be a nucleophilic solvent such as water, methanol, ethanol, glycerol, or combinations thereof. The first mixture may optionally include a co-solvent such as water, methanol, ethanol, glycerol, liquid $CO_2$, or supercritical $CO_2$. The co-solvent can also be nucleophilic (e.g., when the co-solvent is water, methanol, glycerol, or ethanol), or alternatively the co-solvent may not be nucleophilic (e.g., when the co-solvent is liquid $CO_2$ or supercritical $CO_2$). Optionally, the solvent can serve as a reactive modifier. Optionally, the co-solvent can serve as a catalyst to depolymerize the cutin containing portion, and the solvent can serve to transesterify the intermediate depolymerized product. Optionally, the solvent can also include a reactive additive or processing aid such as an enzyme, NaOH, $Na_2CO_3$, acetic acid, another pH modifier, or combinations thereof. If a reactive additive or processing aid is included, the concentration of the reactive additive or processing aid can be sufficiently low such that substantial depolymerization of the cutin does not occur in the absence of the thermal conditions described below. Alternatively, the reactive additive or processing aid can be included in sufficiently high concentration to catalyze the depolymerization process, and the thermal process can be performed to further enhance or increase the reaction rate of the depolymerization process.

The first mixture including the cutin-containing component in the solvent (and optionally the co-solvent and/or the reactive additive or processing aid) is then subjected to elevated temperature and pressure (i.e., a thermal process) for a sufficiently long time to allow the cutin (or cutin-containing component) to at least partially depolymerize into cutin-derived monomers, oligomers, esters thereof, or a combination thereof, thereby forming a second mixture comprising the cutin-derived monomers, oligomers, esters thereof, or a combination thereof. For example, the first mixture can be placed in a vessel such that approximately 50-100% of the vessel volume is filled with the first mixture, and the vessel and enclosed first mixture can then be sealed and heated to a temperature greater than the boiling point of the solvent at atmospheric pressure (i.e., the temperature at which the solvent would have boiled at if it had been maintained at 1 atm). For example, the vessel and enclosed first mixture can be heated above a temperature which is at least 5%, at least 10%, at least 15%, at least 20% at least 25% at least 30%, at least 40%, at least 45%, at least 50%, at least 55%, at least 60%, at least 65%, at least 70%, at least 75%, at least 80%, at least 85%, at least 90%, or at least 100% greater than the boiling point of the solvent at atmospheric pressure (i.e., at 1 atm). In some implementations, the solvent is water, and the mixture is heated to a temperature of at least 393 K, at least 423 K, at least 453 K, at least 473 K, at least 498K, or at least 523 K. In some implementations, the mixture is maintained below a temperature of 1000 K.

Due to thermal expansion of the mixture (and any air or other gas or fluid in the sealed vessel), as well as vaporization of the solvent, the pressure within the vessel increases at the elevated temperature, and can, for example, be greater than 1 atm, greater than 5 atm, greater than 10 atm, or greater than 100 atm. In some implementations, the pressure self-adjusts to a value at or near that of the liquid-gas transition point of the solvent at the elevated temperature, as further described below. The pressure can optionally be further increased within the vessel, for example by pumping nitrogen gas into the vessel, or by pumping solvent into the vessel with pressure maintained by a backflow or pressure regulator. The first mixture can be held at the elevated temperature and pressure for a predetermined amount of time sufficient to cause depolymerization of the cutin-containing component in the first mixture into cutin-derived monomers, oligomers, esters, or combinations thereof, thereby forming the second mixture. After the first mixture is held at the elevated temperature and pressure for the predetermined amount of time to form the second mixture, the second mixture is cooled and the pressure released.

Abbreviations used herein include DHPA [10,16-dihydroxyhexadecanoic acid acid], MEHPA [(E/Z)-16-hydroxyhexadec-9-enoic acid], EtDHPA [ethyl 10.16-dihydroxyhexadecanoate], and EtMEHPA [ethyl (E/Z)-16-hydroxyhexadec-9-enoate].

As used herein, the term "temperature" refers to absolute temperature, as measured in units of Kelvin (K). Accordingly, if a first temperature is X % greater than a second temperature, the first temperature (measured in K) is at least $(1+X/100)$ times the second temperature (measured in K). For example, in the case of water, which has a boiling point of 373.15 K at 1 atm, a temperature which is at least 5% greater than the boiling point of water at 1 atm corresponds to a temperature greater than 391.81 K (i.e., greater than 1.05×373.15 K).

In some implementations, the cutin-derived monomers, oligomers, esters or combinations thereof resulting from the thermal depolymerization process are soluble in the solvent at the elevated temperature at which the thermal process is carried out, and also at the temperature at which the second mixture is subsequently cooled to (typically room temperature). This can be the case when the solvent is ethanol or methanol, for example. In other implementations, the cutin-derived monomers, oligomers, esters, or combinations thereof resulting from the thermal depolymerization process are insoluble in the solvent at the elevated temperature at which the thermal process is carried out, and also at the temperature at which the second mixture is subsequently cooled to. In still other implementations, the cutin-derived monomers, oligomers, esters, or combinations thereof resulting from the thermal depolymerization process are soluble in the solvent at the elevated temperature at which the thermal process is carried out, but are insoluble at the temperature at which the second mixture is subsequently cooled to (e.g., room temperature or about 300 K). In this case, the monomers, oligomers, esters, or combinations thereof which are dissolved at the elevated temperature precipitate as the second mixture is cooled to room temperature, resulting in the monomers, oligomers, esters, or combinations thereof being suspended in the solvent, and for example being intermixed with other non-cutin plant matter as a solid char. When water is used as the solvent, for example, the cutin-derived monomers, oligomers, esters, or combinations thereof typically may be insoluble at room temperature, but may or may not be soluble at the elevated temperature and pressure, depending on the specific plant from which the cutin is sourced.

As previously described, while heating the first mixture to and holding it at the elevated temperature, the pressure within the vessel can be increased to ensure that at least 50% of the solvent is maintained in the liquid phase. For example, consider the phase diagram 100 of water ($H_2O$) shown in FIG. 1. When water, which has a boiling point of about 373 K at 1 atm, is used as the solvent in the first mixture, the first mixture can be heated to a second temperature greater than 373 K (e.g., temperature 104 in FIG. 1) and maintained substantially in the liquid phase if the pressure is also increased to a second pressure which is greater than or about equal to that at the liquid-gas phase boundary for the particular temperature. For example, when the first mixture is heated to temperature 104, the pressure can increase such that the water in the mixture is at point 102 in the phase diagram 100 of FIG. 1.

As previously described, the increased pressure required to maintain at least 50% of the solvent in the liquid phase at the elevated temperature can be achieved, for example, by sealing the vessel such that the pressure in the vessel increases as the temperature is increased due to thermal expansion of the mixture, vaporization of some portion of the solvent, and/or thermal expansion of any air or other gas or fluid in the sealed vessel. The resulting pressure in the vessel can self-adjust so that it is approximately at the liquid-gas transition point. For example, the pressure can adjust to a value that is within 1%, within 2% or within 5% of the liquid-gas transition point at the elevated temperature. The exact value of the resulting pressure depends at least partially on the percent volume of the vessel which is filled with the mixture. However, if the fill ratio is too large, e.g., if the fill ratio approaches 1, the pressure may become too high for the vessel to support mechanically. Accordingly, in some implementations, more than 50% but less than 99% of the vessel volume is filled with the mixture. For example, between 60% and 95% or between 70% and 95% of the vessel volume may be filled with the mixture. Furthermore, in some implementations the pressure in the vessel at the elevated temperature is sufficient to maintain at least 60%, at least 70%, at least 80%, at least 90%, or substantially all of the solvent in the liquid phase.

Additionally, the pressure within the vessel can be further increased by pumping additional gas or liquid, for example nitrogen, into the vessel. This can allow the pressure within the vessel to be directly controlled by means of a pressure regulator or backflow preventer in order to better optimize the depolymerization process, which is further described below. Furthermore, if the liquid contains additional material to be processed, a flow through reaction may be implemented.

The solvent in which the cutin-containing portion is depolymerized can be selected such that the cutin-containing portion is not substantially depolymerized at room temperature (e.g., at 300 K) and/or is not substantially depolymerized or has a very low depolymerization rate at temperatures below the boiling point at 1 atm. Thus, in many cases, the rate of depolymerization is only high enough for substantial depolymerization to occur when the temperature is raised substantially above the atmospheric boiling point of the solvent (e.g., at least 5% or at least 10% above the atmospheric boiling point). As such, in order to maintain the solvent in the liquid phase so that depolymerization can occur, the pressure in the vessel is raised accordingly, as previously described.

Substantial depolymerization of the cutin-containing portion can alternatively be achieved at room temperature or at temperatures below the atmospheric boiling point of the solvent by acidifying or alkalizing the solvent, for example by adding metal hydroxides to the solvent. However, the thermal depolymerization process described above can provide certain advantages over such a process. For example, the thermal depolymerization process can self generate both reactive anions and cations in the solvent, thereby depolymerizing the cutin into monomer/oligomer units. The depolymerization products are inherently uncharged, which may be necessary or desirable for subsequently modifying (e.g., esterifying or glycerating) the monomer/oligomer units and/or for forming protective coatings from the monomer/oligomer units. Conversely, depolymerization in a strong base typically does not result in the monomer and/or oligomer products of the depolymerization process being uncharged. As such, additional steps in which the monomer/oligomer products are neutralized may be required in order to form protective coatings having desirable properties from the monomer/oligomer units. Additionally, omitting the use of strong acids and/or bases from the depolymerization process can result in the process being recognized as fully organic.

The specific temperature(s) at which the thermal depolymerization process is carried out, as well as the composition of the solvent, can be selected such that concentrations of reactive anions and reactive cations in the solvent while the solvent is held at the elevated temperature (and corresponding elevated pressure) are sufficient to depolymerize the cutin. The temperature may further be selected such that the rate of depolymerization of the cutin in the solvent is at least 100 times greater at the elevated temperature (and corresponding elevated pressure) than at standard temperature and pressure. For example, when $H_2O$ is used as the solvent for the thermal depolymerization process, the temperature can be greater than 393 K, for example at least 413 K, at least 433 K, at least 453 K, at least 473K, greater than 483 K, greater than 498 K, greater than 513 K, greater than 523 K, between 473 K and 523 K, or between 493 K and 533 K. In some implementations, the thermal depolymerization process is carried out using supercritical $H_2O$ as the solvent and optionally using supercritical $CO_2$ as a co-solvent, in which case the elevated temperature is greater than 647 K and the pressure is greater than 218 atm (e.g., between 218 and 1000 atm). In some implementations, the thermal depolymerization process is carried out using supercritical ethanol as the solvent and optionally using supercritical $CO_2$ as a co-solvent, in which case the elevated temperature can be greater than 514 K and the pressure can be greater than 60.6 atm (e.g., between 60.6 and 1000 atm).

Figure 2A:
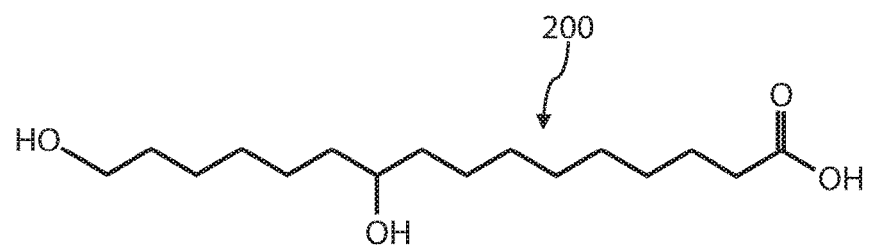
FIGS. 2A, 2B, 2C, 2D, 2E, and 2F show the chemical structure of 10,16-dihydroxyhexadecanoic acid, 10,18-dihydroxyoctadecanoic acid, 9,16-dihydroxyhexadecanoic acid, 9,18-dihydroxyoctadecanoic acid, 9,10,16-trihydroxyhexadecanoic acid, 9,10,18-trihydroxyoctadecanoic acid, respectively.
Figure 2B:
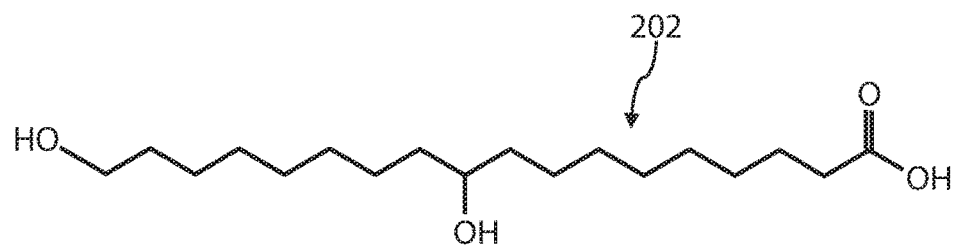
Figure 2C:
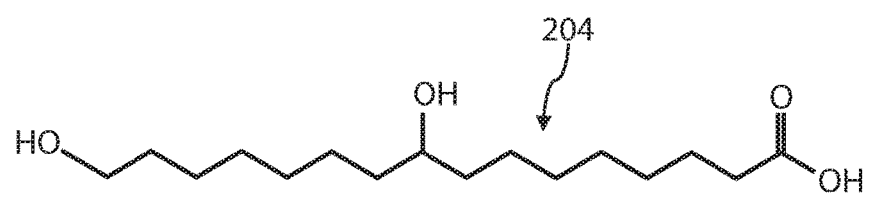
Figure 2D:
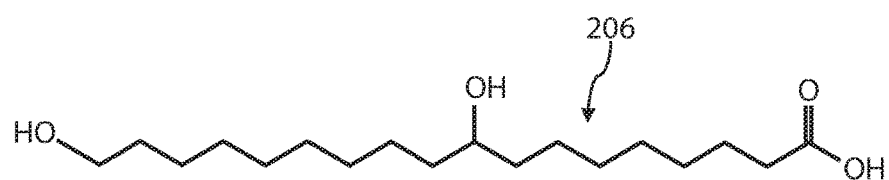
Figure 2E:
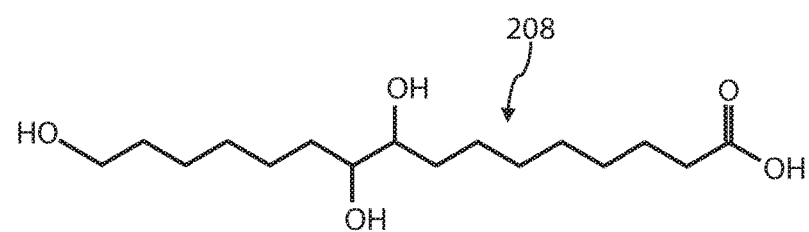
Figure 2F:
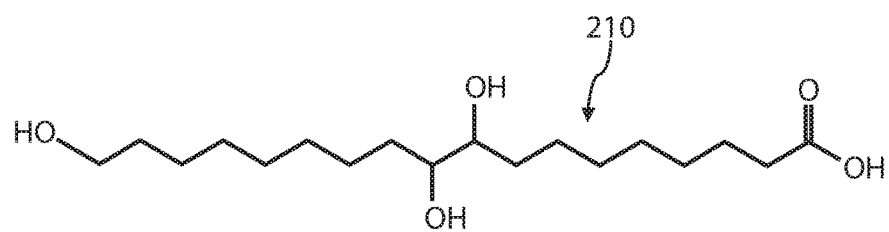

FIG. 2A shows the chemical composition of 10,16-dihydroxyhexadecanoic acid (200 in FIG. 2A), and FIG. 2B shows the chemical composition of 10,18-dihydroxyoctadecanoic acid (202 in FIG. 2B), both of which are typical direct monomer products of the cutin thermal depolymerization process carried out with water as a solvent, and form the majority building block of cutin. Other direct monomer products that can result from the cutin thermal depolymerization process carried out with water as a solvent are shown in FIGS. 2C, 2D, 2E, and 2F, where FIG. 2C shows the chemical composition of 9,16-dihydroxyhexadecanoic acid (204 in FIG. 2C), FIG. 2D shows the chemical composition of 9,18-dihydroxyoctadecanoic acid (206 in FIG. 2D), FIG. 2E shows the chemical composition of 9,10,16-trihydroxyhexadecanoic acid (208 in FIG. 2E), and FIG. 2F shows the chemical composition of 9,10,18-trihydroxyoctadecanoic acid (210 in FIG. 2F). The exact products that result directly from the thermal depolymerization process depend on the particular plant source of the cutin and the solvent in which the thermal depolymerization process is carried out. For example, cutin from tomatoes tends to have a high proportion of $C_{16}$ acids (e.g., fatty acids having a carbon chain length of 16) such as that of FIGS. 2A, 2C, 2E, and 2G, whereas cutin from cranberries tends to have a high proportion of $C_{18}$ acids such as that of FIGS. 2B, 2D, and 2F. In some implementations, the thermal depolymerization process produces compounds of Formula I:

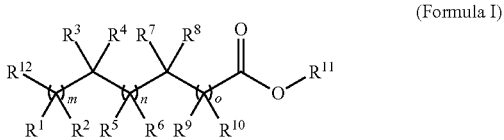

(Formula I)

where $R^1$, $R^2$, $R^3$, $R^4$, $R^5$, $R^6$, $R^7$, $R^8$, $R^9$, $R^{10}$, $R^{11}$, $R^{12}$, m, n, and o are as previously defined for Formula I. In some embodiments, $R^1$, $R^2$, $R^3$, $R^4$, $R^5$, $R^6$, $R^7$, $R^8$, $R^9$, $R^{10}$, $R^{11}$, $R^{12}$ in Formula I are H.

Figure 3A:
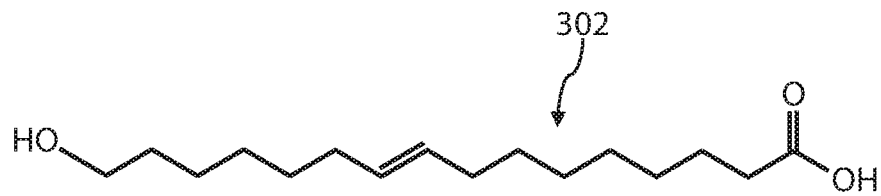
FIGS. 3A, 3B, 3C, 3D, 3E, 3F, 3G, 3H and 3I are byproducts that can result from the decomposition of 10,16-dihydroxyhexadecanoic acid monomers and/or oligomers during a thermal depolymerization process.
Figure 3B:
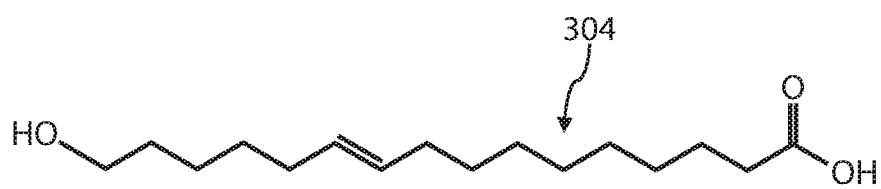
Figure 3C:
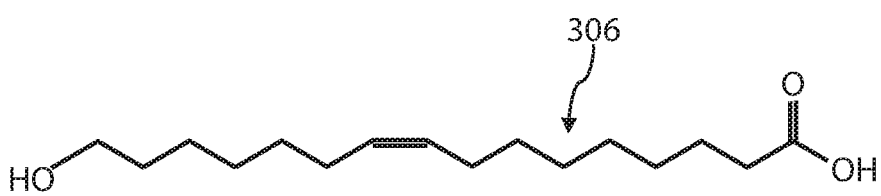
Figure 3D:
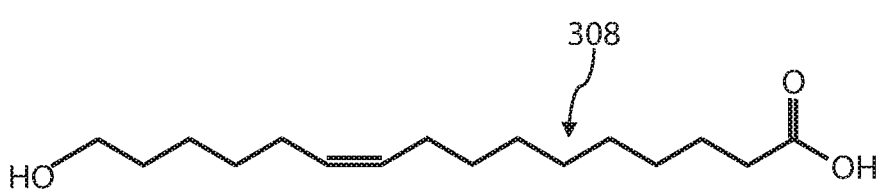
Figure 3E:
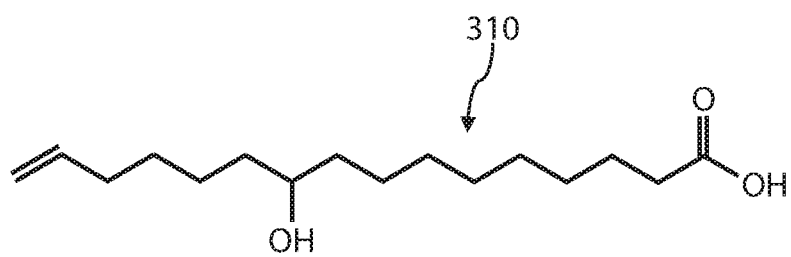
Figure 3F:
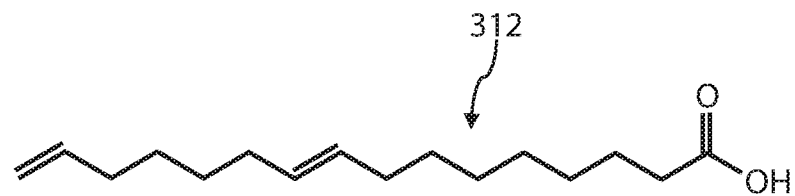
Figure 3G:
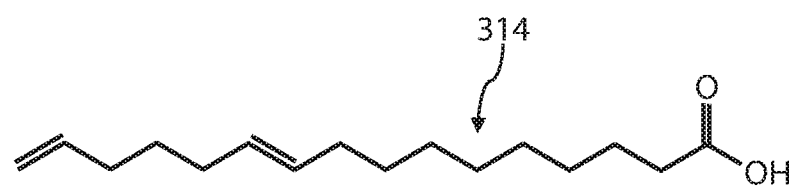
Figure 3H:
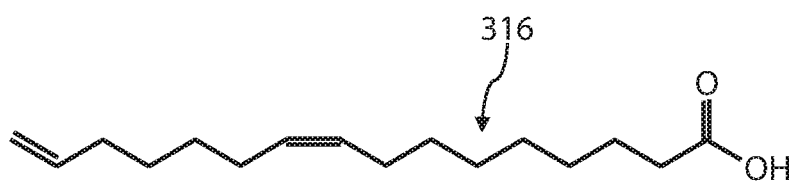
Figure 3I:
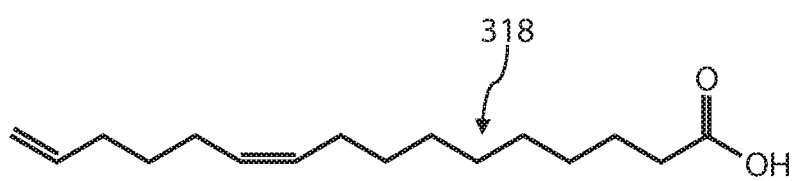

In addition to the compounds of Formula I, as well as monomers and/or oligomers of the molecules 200, 202, 204, 206, 208, and 210 in FIGS. 2A-2F, respectively, other products may also be formed during the thermal depolymerization process carried out in water that are not formed by depolymerization of cutin by other methods. For example, unsaturated products 302, 304, 306, 308, 310, 312, 314, 316, and/or 318 in FIGS. 3A-3I, respectively, can be formed during the thermal depolymerization process carried out in water. Here FIG. 3A illustrates (E)-16-hydroxyhexadec-9-enoic acid (302), FIG. 3B illustrates (E)-16-hydroxyhexadec-10-enoic acid (304), FIG. 3C illustrates (Z)-16-hydroxyhexadec-9-enoic acid (306), FIG. 3D illustrates (Z)-16-hydroxyhexadec-10-enoic acid (308), FIG. 3E illustrates 10-hydroxyhexadec-15-enoic acid (310), FIG. 3F illustrates (E)-hexadeca-9,15-dienoic acid (312), FIG. 3G illustrates (E)-hexadeca-10,15-dienoic acid (314), FIG. 3H illustrates (Z)-hexadeca-9,15-dienoic acid (316), and FIG. 3I illustrates (Z)-hexadeca-10,15-dienoic acid (318). In general, the thermal depolymerization methods described herein can produce compounds of Formula II:

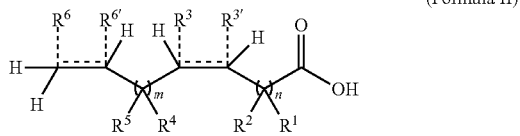

(Formula II)

where $R^1$, $R^2$, $R^3$, $R^{3'}$, $R^4$, $R^5$, $R^6$, $R^{6'}$, m, and n are as previously defined for Formula II. In some embodiments, $R^1$, $R^2$, $R^3$, $R^{3'}$, $R^4$, $R^5$, $R^6$, $R^{6'}$ in Formula II are H.

In some embodiments, the thermal depolymerization methods described herein can produce compounds of the Formula III:

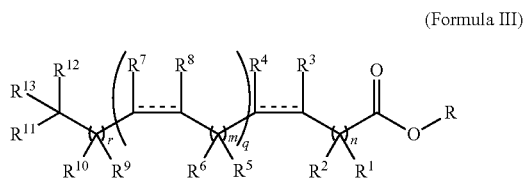

(Formula III)

wherein:

$R^1$, $R^2$, $R^5$, $R^6$, $R^9$, $R^{10}$, $R^{11}$, $R^{12}$ and $R^{13}$ are each independently, at each occurrence, —H, —OR$^{14}$, —NR$^{14}$R$^{15}$, —SR$^{14}$, halogen, —C$_1$-C$_6$ alkyl, —C$_2$-C$_6$ alkenyl, —C$_2$-C$_6$ alkynyl, —C$_3$-C$_7$ cycloalkyl, aryl, or heteroaryl, wherein each alkyl, alkenyl, alkynyl, cycloalkyl, aryl, or heteroaryl is optionally substituted with one or more —OR$^{14}$, —NR$^{14}$R$^{15}$, —SR$^{14}$, or halogen;

$R^3$, $R^4$, $R^7$, and $R^8$ are each independently, at each occurrence, —H, —OR$^{14}$, —NR$^{14}$R$^{15}$, —SR$^{14}$, halogen, —C$_1$-C$_6$ alkyl, —C$_2$-C$_6$ alkenyl, —C$_2$-C$_6$ alkenyl, —C$_2$-C$_6$ alkynyl, —C$_3$-C$_7$ cycloalkyl, aryl, or heteroaryl wherein each alkyl, alkynyl, cycloalkyl, aryl, or heteroaryl is optionally substituted with one or more —OR$^{14}$, —NR$^{14}$R$^{15}$, —SR$^{14}$, or halogen; or $R^3$ and $R^4$ can combine with the carbon atoms to which they are attached to form a $C_3$-$C_6$ cycloalkyl, a $C_4$-$C_6$ cycloalkenyl, or 3- to 6-membered ring heterocycle; and/or $R^7$ and $R^8$ can combine with the carbon atoms to which they are attached to form a $C_3$-$C_6$ cycloalkyl, a $C_4$-$C_6$ cycloalkenyl, or 3- to 6-membered ring heterocycle;

$R^{14}$ and $R^{15}$ are each independently, at each occurrence, —H, —C$_1$-C$_6$ alkyl, —C$_2$-C$_6$ alkenyl, or —C$_2$-C$_6$ alkynyl;

the symbol ==== represents a single bond or a cis or trans double bond;

n is 0, 1, 2, 3, 4, 5, 6, 7 or 8;

m is 0, 1, 2 or 3;

q is 0, 1, 2, 3, 4 or 5; and r is 0, 1, 2, 3, 4, 5, 6, 7 or 8; and

R is selected from —H, —C$_1$-C$_6$ alkyl, —C$_2$-C$_6$ alkenyl, —C$_2$-C$_6$ alkynyl, —C$_3$-C$_7$ cycloalkyl, aryl, 1-glycerol, 2-glycerol, or heteroaryl.

In some embodiments, R can be —H, —CH$_3$, or —CH$_2$CH$_3$.

In some embodiments, the thermal depolymerization methods described herein can produce compounds of the Formula III-A:

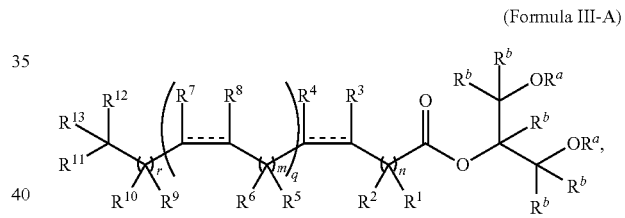

(Formula III-A)

wherein:

each $R^a$ is independently —H or —C$_1$-C$_6$ alkyl;

each $R^b$ is independently selected from —H, —C$_1$-C$_6$ alkyl, or —OH;

$R^1$, $R^2$, $R^5$, $R^6$, $R^9$, $R^{10}$, $R^{11}$, $R^{12}$ and $R^{13}$ are each independently, at each occurrence, —H, —OR$^{14}$, —NR$^{14}$R$^{15}$, —SR$^{14}$, halogen, —C$_1$-C$_6$ alkyl, —C$_2$-C$_6$ alkenyl, —C$_2$-C$_6$ alkynyl, —C$_3$-C$_7$ cycloalkyl, aryl, or heteroaryl, wherein each alkyl, alkenyl, alkynyl, cycloalkyl, aryl, or heteroaryl is optionally substituted with one or more —OR$^{14}$, —NR$^{14}$R$^{15}$, —SR$^{14}$, or halogen;

$R^3$, $R^4$, $R^7$, and $R^8$ are each independently, at each occurrence, —H, —OR$^{14}$, —NR$^{14}$R$^{15}$, —SR$^{14}$, halogen, —C$_1$-C$_6$ alkyl, —C$_2$-C$_6$ alkenyl, —C$_2$-C$_6$ alkynyl, —C$_3$-C$_7$ cycloalkyl, aryl, or heteroaryl wherein each alkyl, alkynyl, cycloalkyl, aryl, or heteroaryl is optionally substituted with one or more —OR$^{14}$, —NR$^{14}$R$^{15}$, —SR$^{14}$, or halogen; or $R^3$ and $R^4$ can combine with the carbon atoms to which they are attached to form a $C_3$-$C_6$ cycloalkyl, a $C_4$-$C_6$ cycloalkenyl, or 3- to 6-membered ring heterocycle; and/or $R^7$ and $R^8$ can combine with the carbon atoms to which they are attached to form a $C_3$-$C_6$ cycloalkyl, a $C_4$-$C_6$ cycloalkenyl, or 3- to 6-membered ring heterocycle;

$R^{14}$ and $R^{15}$ are each independently, at each occurrence, —H, —C$_1$-C$_6$ alkyl, —C$_2$-C$_6$ alkenyl, or —C$_2$-C$_6$ alkynyl;

the symbol ===== represents a single bond or a cis or trans double bond;
n is 0, 1, 2, 3, 4, 5, 6, 7 or 8;
m is 0, 1, 2 or 3;
q is 0, 1, 2, 3, 4 or 5; and
r is 0, 1, 2, 3, 4, 5, 6, 7 or 8.

In some embodiments, the thermal depolymerization methods described herein can produce compounds of the Formula III-B:

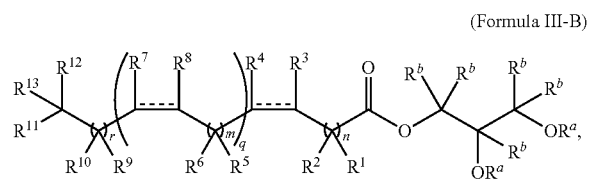

(Formula III-B)

wherein:
each $R^a$ is independently —H or —$C_1$-$C_6$ alkyl;
each $R^b$ is independently selected from —H, —$C_1$-$C_6$ alkyl, or —OH;
$R^1$, $R^2$, $R^5$, $R^6$, $R^9$, $R^{10}$, $R^{11}$, $R^{12}$ and $R^{13}$ are each independently, at each occurrence, —H, —$OR^{14}$, —$NR^{14}R^{15}$, —$SR^{14}$, halogen, —$C_1$-$C_6$ alkyl, —$C_2$-$C_6$ alkenyl, —$C_2$-$C_6$ alkynyl, —$C_3$-$C_7$ cycloalkyl, aryl, or heteroaryl, wherein each alkyl, alkenyl, alkynyl, cycloalkyl, aryl, or heteroaryl is optionally substituted with one or more —$OR^{14}$, —$NR^{14}R^{15}$, —$SR^{14}$, or halogen;
$R^3$, $R^4$, $R^7$, and $R^8$ are each independently, at each occurrence, —H, —$OR^{14}$, —$NR^{14}R^{15}$, —$SR^{14}$, halogen, —$C_1$-$C_6$ alkyl, —$C_2$-$C_6$ alkenyl, —$C_2$-$C_6$ alkynyl, —$C_3$-$C_7$ cycloalkyl, aryl, or heteroaryl wherein each alkyl, alkenyl, alkynyl, cycloalkyl, aryl, or heteroaryl is optionally substituted with one or more —$OR^{14}$, —$NR^{14}R^{15}$, —$SR^{14}$, or halogen; or
$R^3$ and $R^4$ can combine with the carbon atoms to which they are attached to form a $C_3$-$C_6$ cycloalkyl, a $C_4$-$C_6$ cycloalkenyl, or 3- to 6-membered ring heterocycle; and/or
$R^7$ and $R^8$ can combine with the carbon atoms to which they are attached to form a $C_3$-$C_6$ cycloalkyl, a $C_4$-$C_6$ cycloalkenyl, or 3- to 6-membered ring heterocycle;
$R^{14}$ and $R^{15}$ are each independently, at each occurrence, —H, —$C_1$-$C_6$ alkyl, —$C_2$-$C_6$ alkenyl, or —$C_2$-$C_6$ alkynyl;
the symbol ===== represents a single bond or a cis or trans double bond;
n is 0, 1, 2, 3, 4, 5, 6, 7 or 8;
m is 0, 1, 2 or 3;
q is 0, 1, 2, 3, 4 or 5; and
r is 0, 1, 2, 3, 4, 5, 6, 7 or 8.

In some embodiments, the thermal depolymerization methods described herein can produce one or more of the following fatty acid compounds:

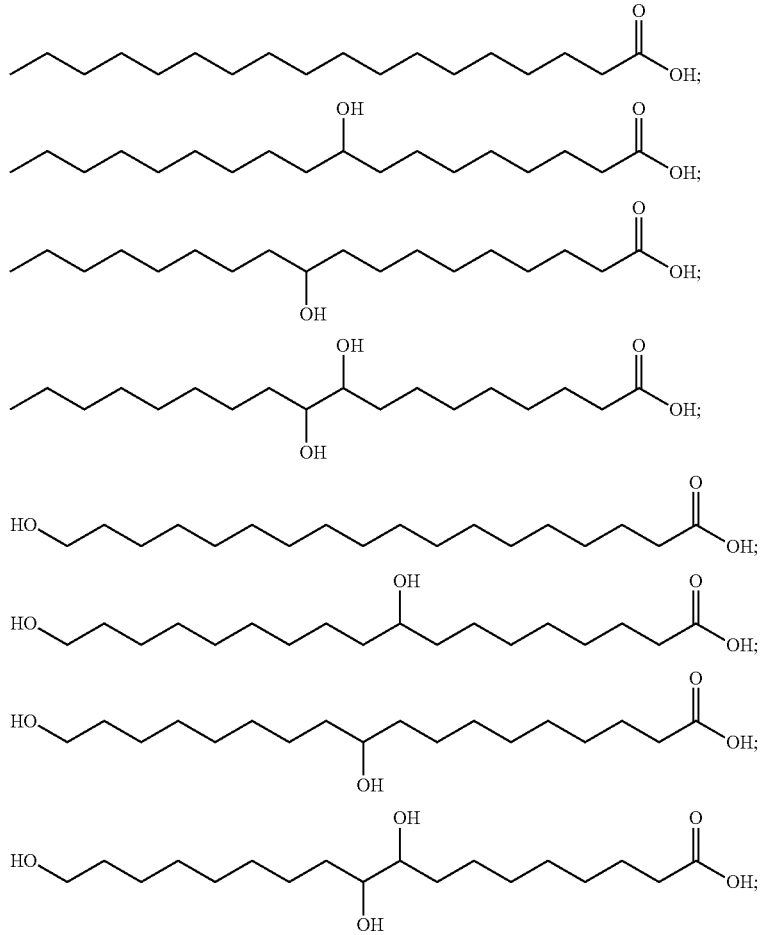

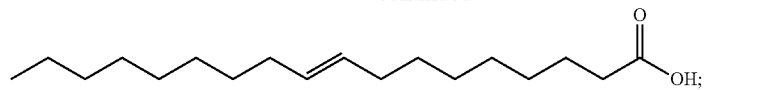
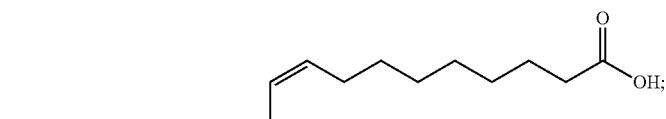
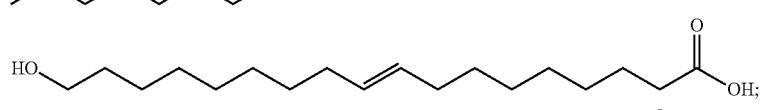
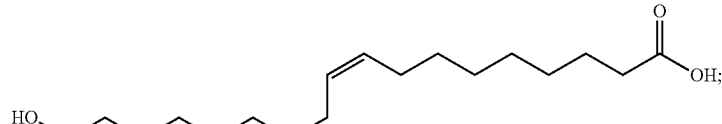
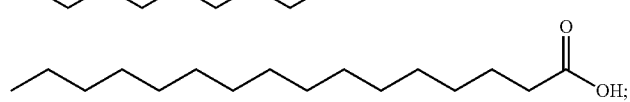
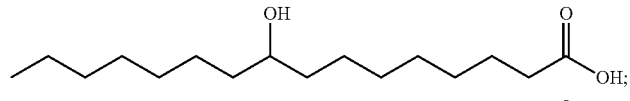
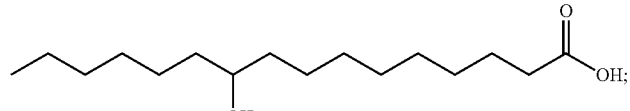
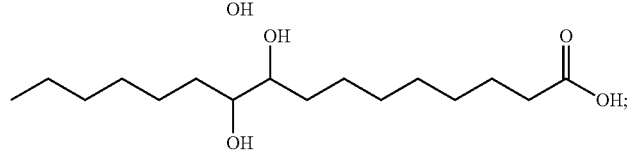
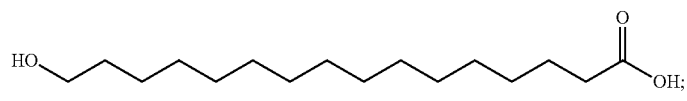
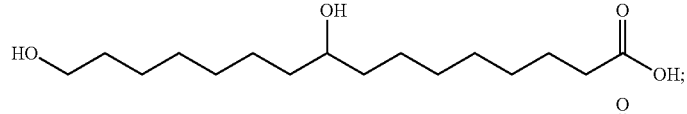
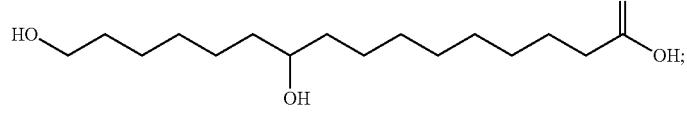
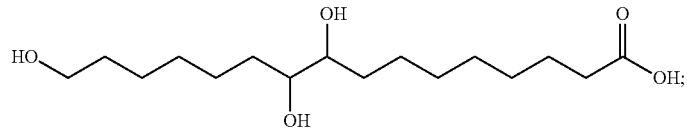
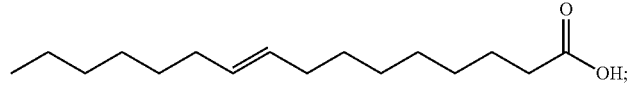
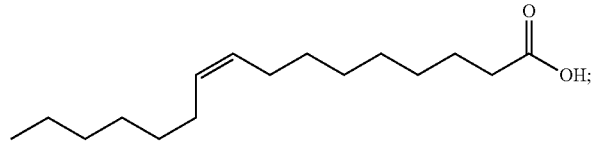

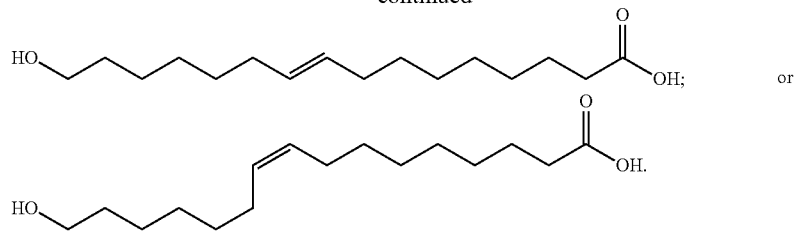
In some embodiments, the thermal depolymerization methods described herein can produce one or more of the following methyl ester compounds:
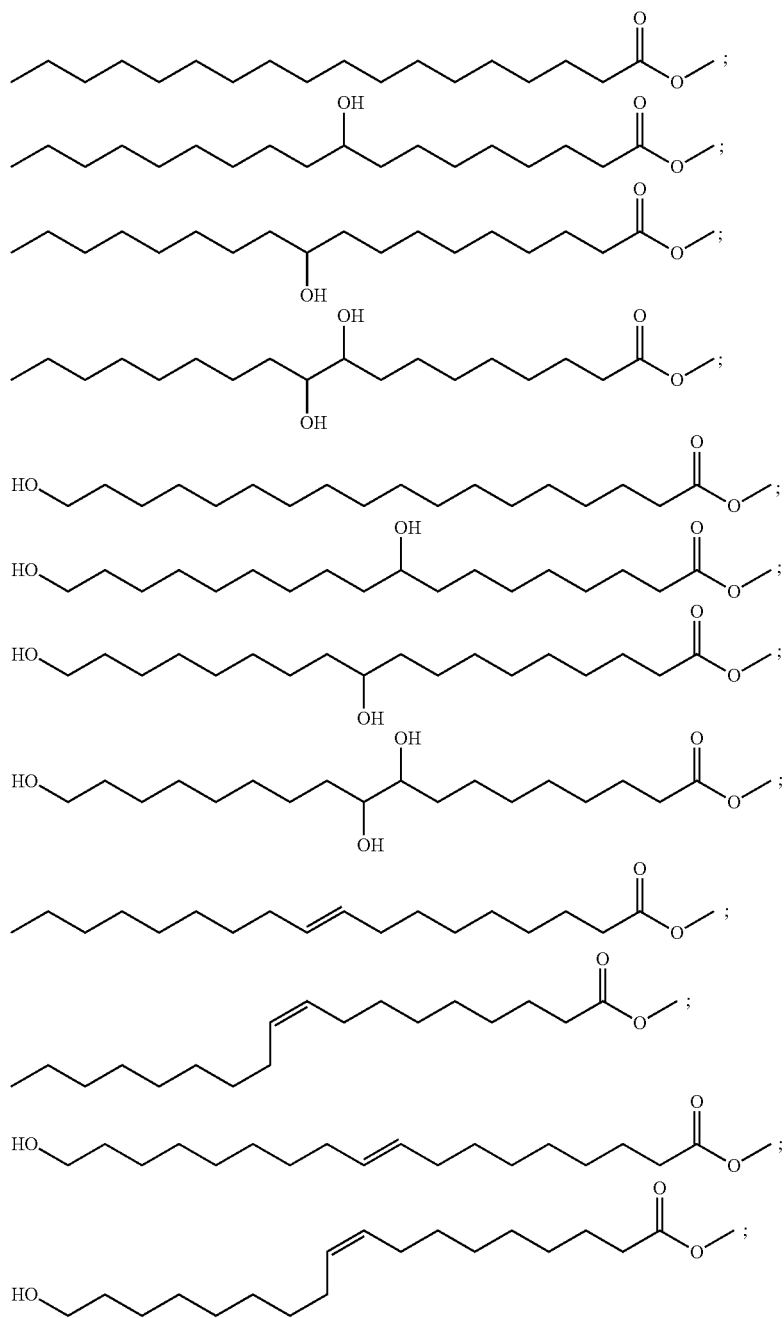

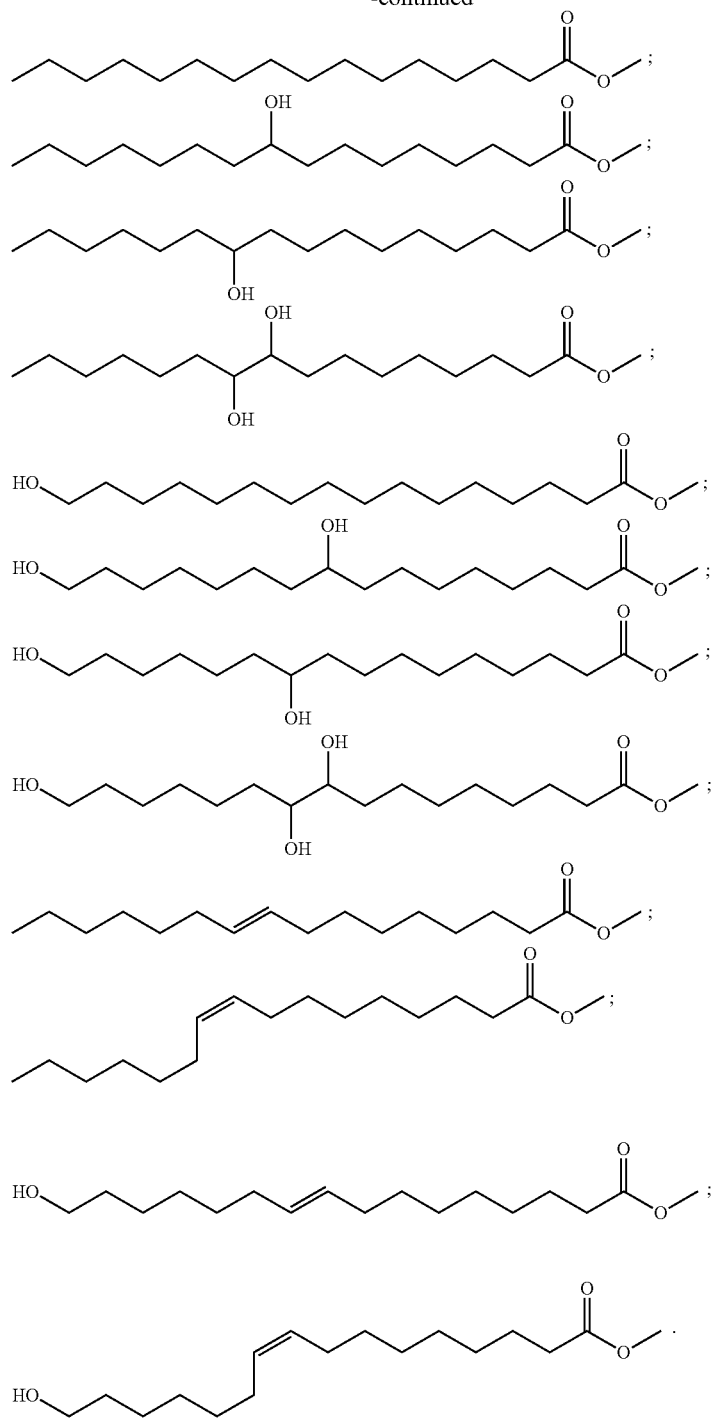
In some embodiments, the thermal depolymerization methods described herein can produce one or more of the following ethyl ester compounds:
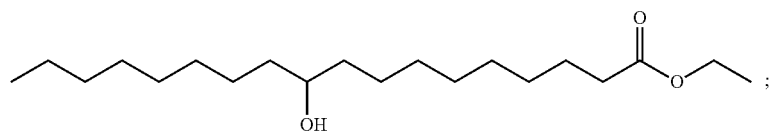

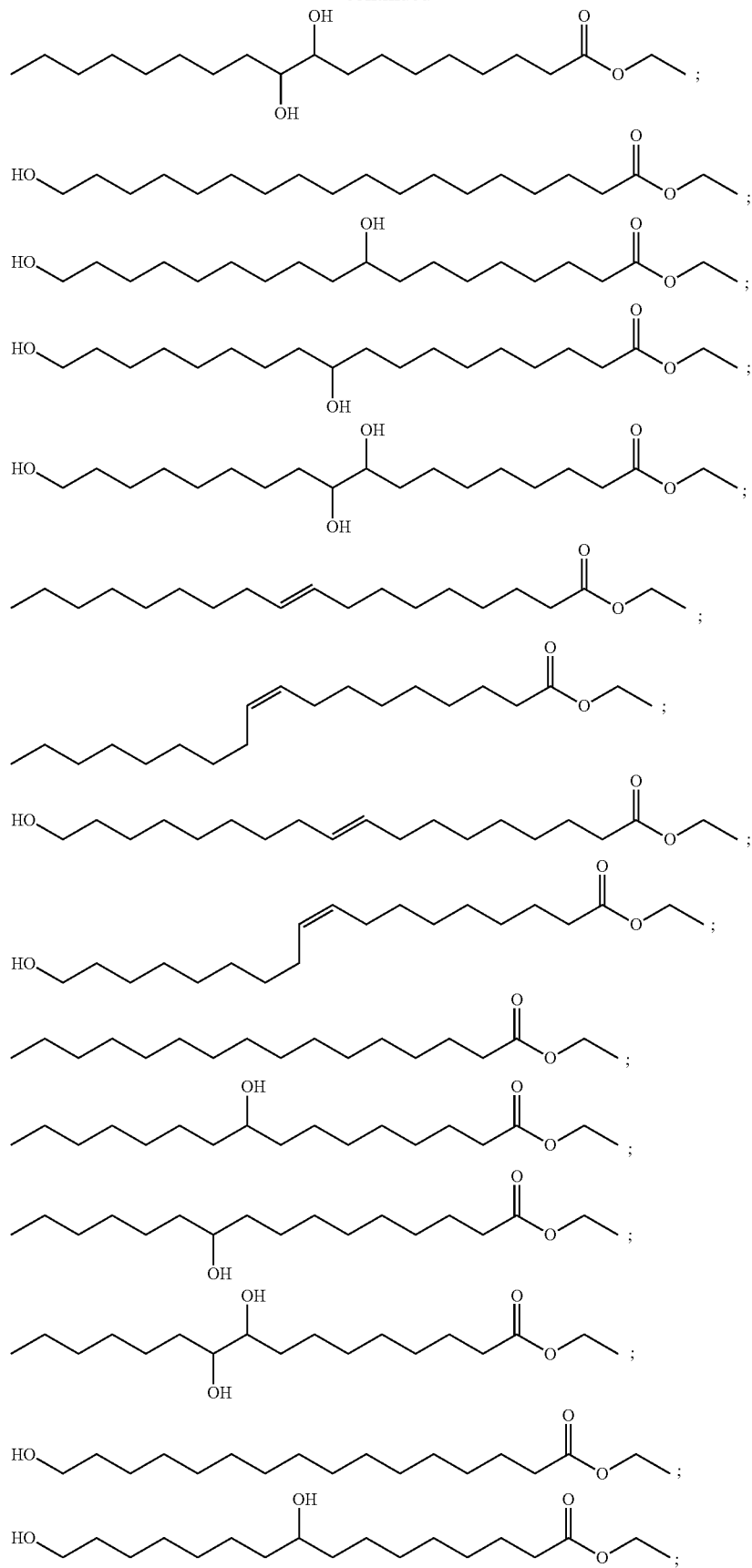

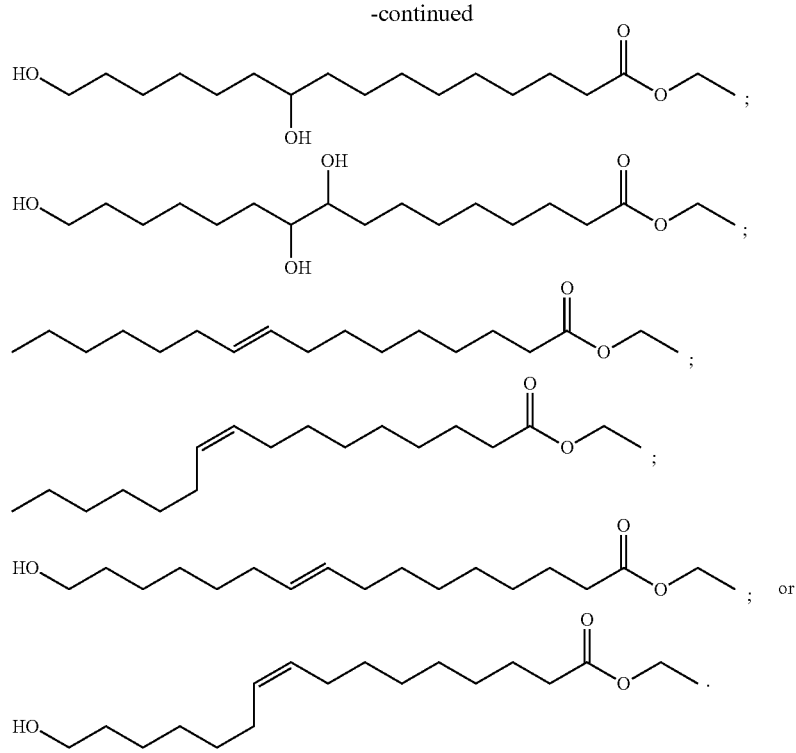
In some embodiments, the thermal depolymerization methods described herein can produce one or more of the following 2-glycerol ester compounds:
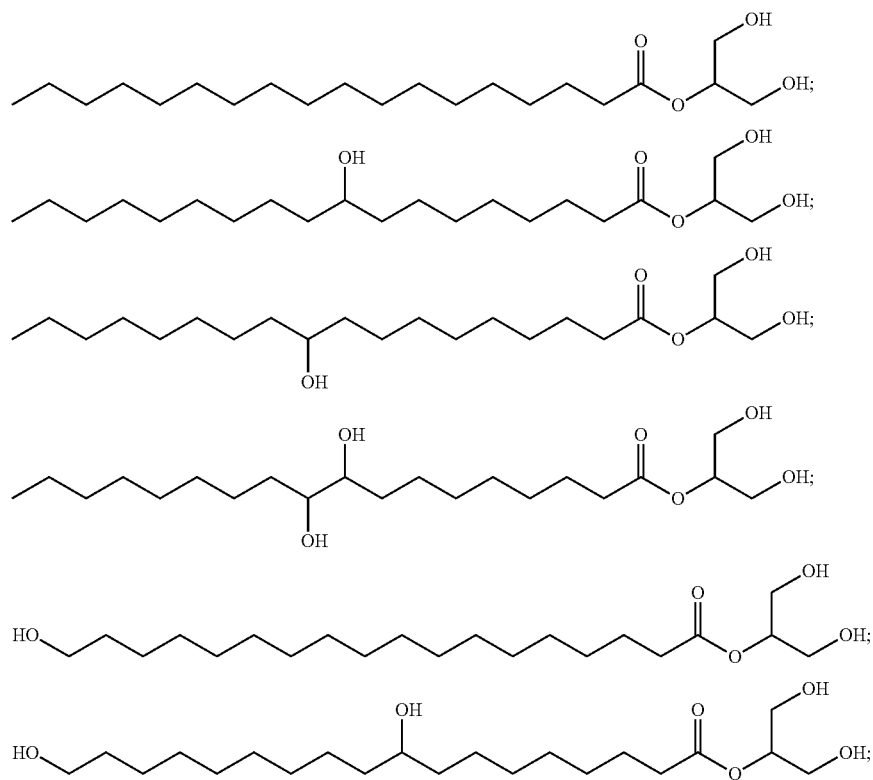

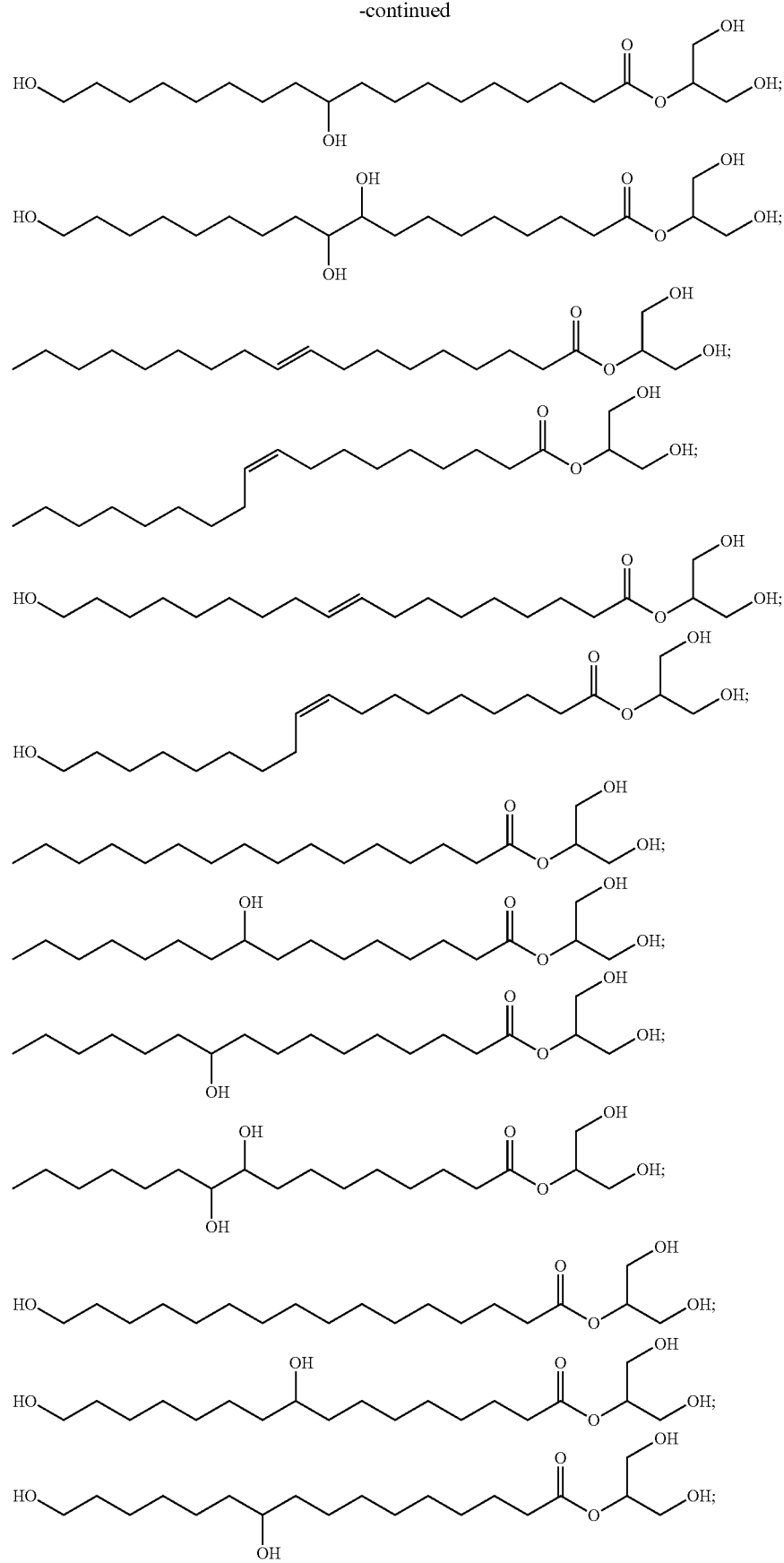

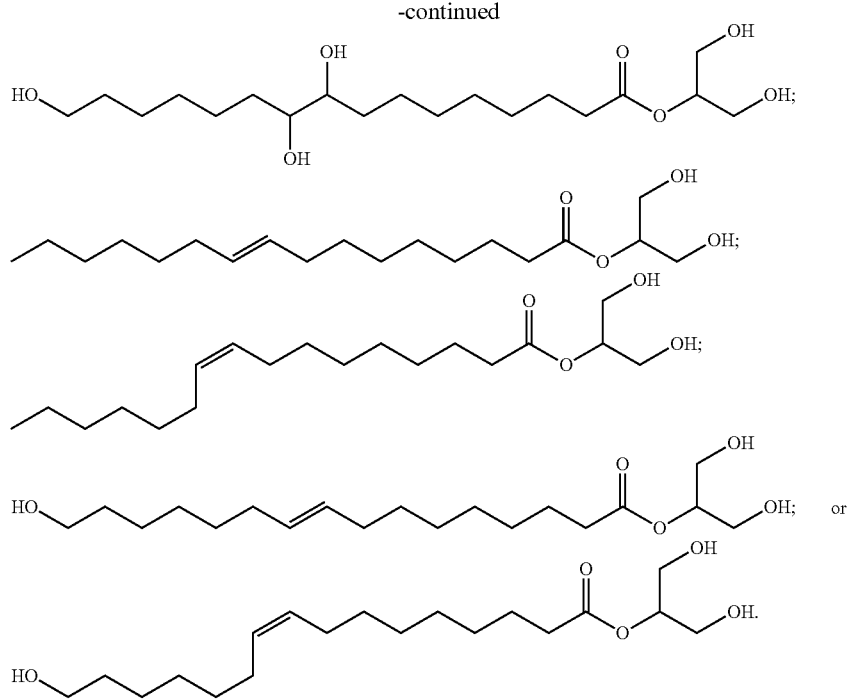
In some embodiments, the thermal depolymerization methods described herein can produce one or more of the following 1-glycerol ester compounds:
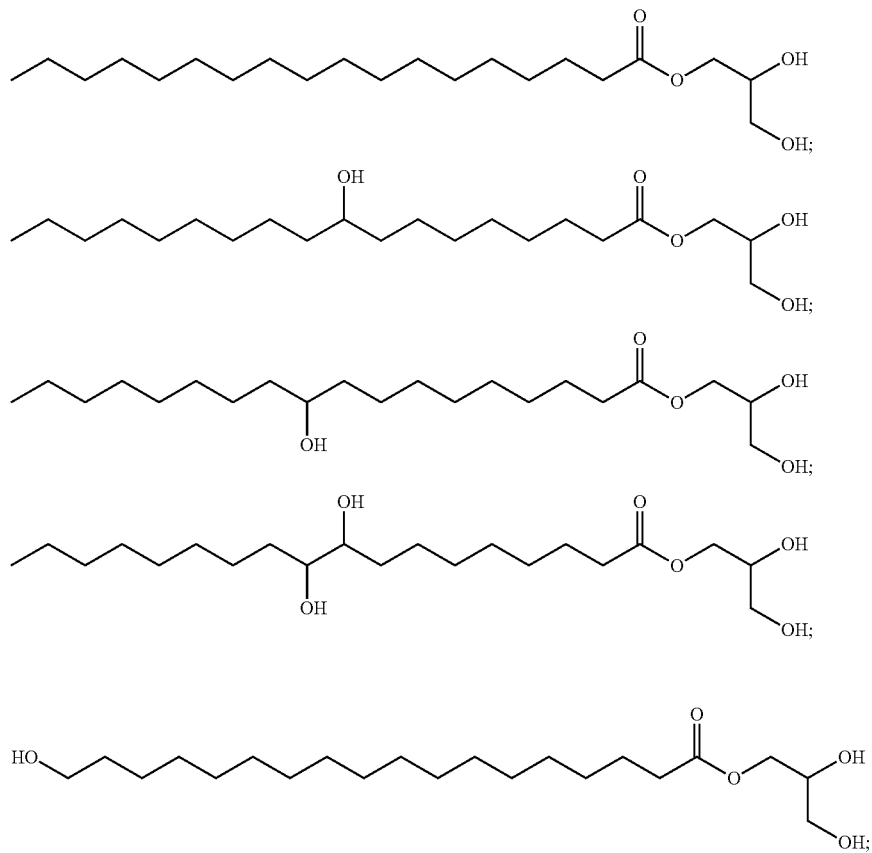

-continued
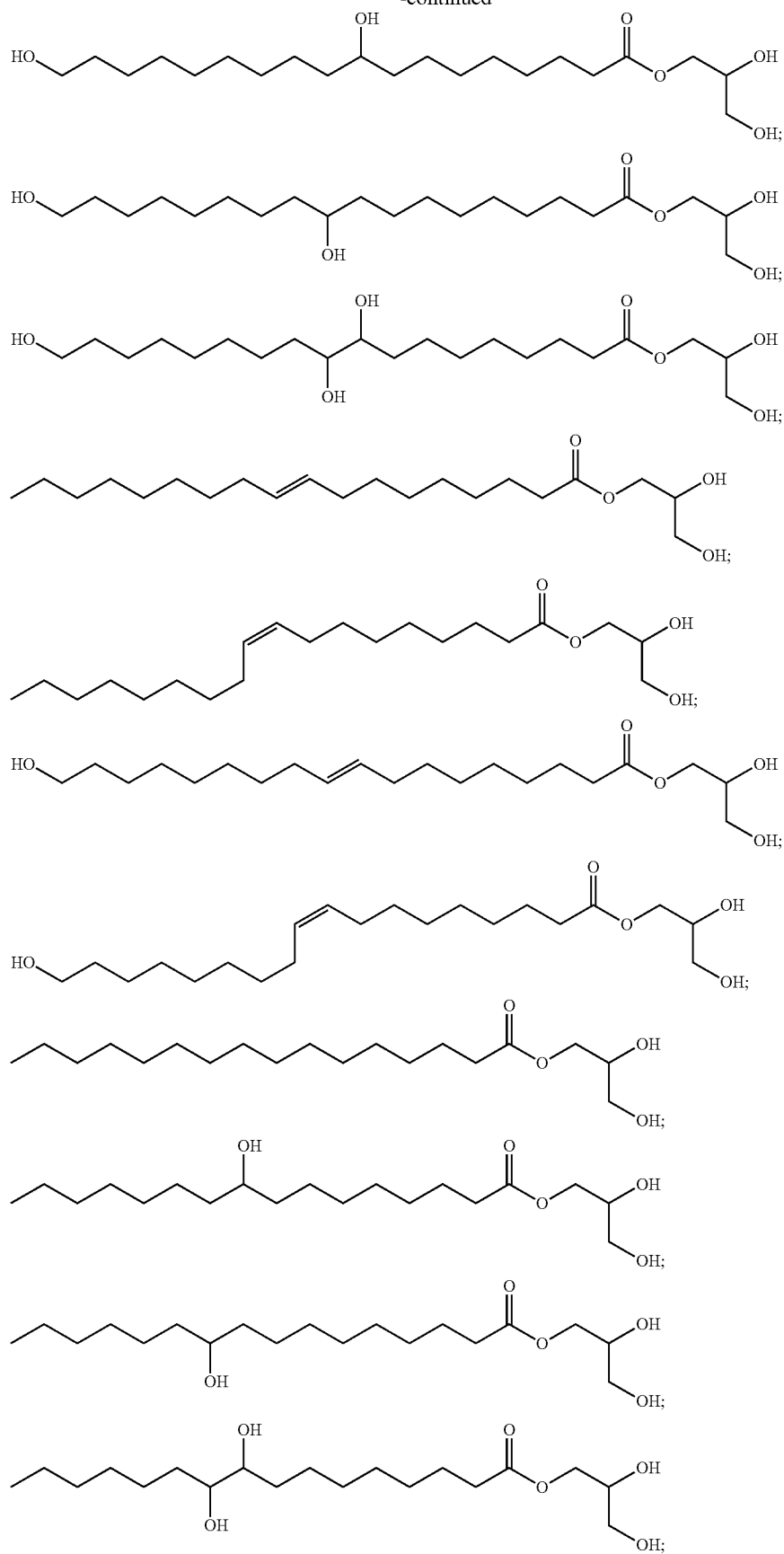

-continued
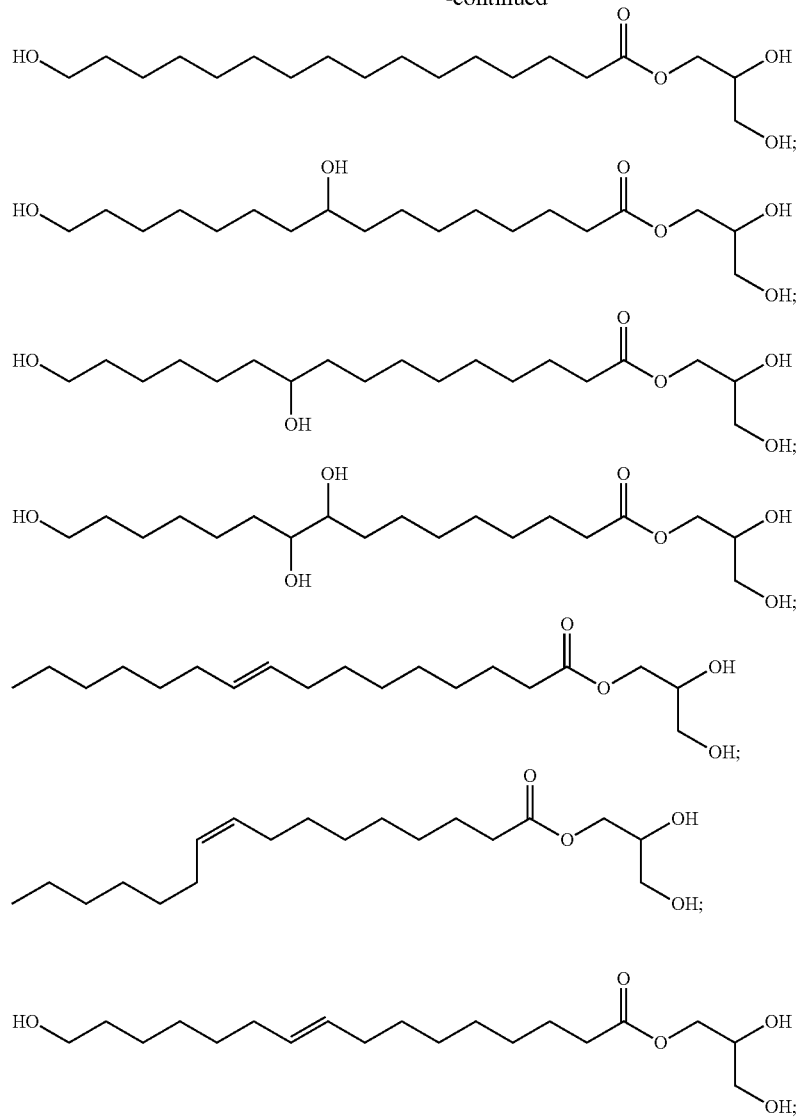
In some embodiments, any of the compounds described herein (e.g., compounds of Formula I, II, or III) can be crosslinked to create a dimer, trimer, or oligomer. For instance, a dimer can have the structure set forth below:
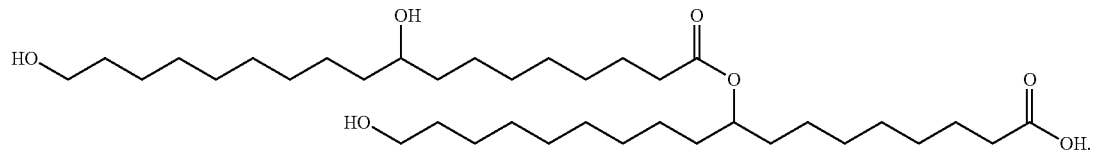 [SMILES: O=C(O)CCCCCCCC(CCCCCCCCCO)OC(=O)CCCCCCCC(O)CCCCCCCCCO]

One of skill in the art will understand that other crosslinked dimers, trimers, or oligomers can be created in accordance with the present disclosure. Additionally, one of skill in the art will understand that at the temperatures and pressures used to depolymerize cutin described herein, oxidation of primary or secondary alcohols can occur. For example, when carried out in the present of oxygen (e.g., air), it is possible that an alcohol moiety can be oxidized to a corresponding ketone.

Without wishing to be bound by theory, it is believed that the saturated products (e.g., 200, 202, 204, 206, 208, and/or 210) are cross-linked within the cutin layer and are thereby isolated into monomer and/or oligomer units directly via depolymerization reactions, whereas the unsaturated products (e.g., 302, 304, 306, 308, 310, 312, 314, 316, 318, and/or products of Formula II) are indirect byproducts that are formed by decomposition of the direct products (e.g., 200, 202, 204, 206, 208, and/or 210). The decomposition can occur, for example, if high temperature and/or high pressure conditions are maintained for too long a period of time during the thermal depolymerization process, where the length of time necessary to produce the unsaturated byproducts decreases with increasing temperature. However, it may be possible that the unsaturated products (e.g., 302, 304, 306, 308, 310, 312, 314, 316, 318, and/or products of Formula II) are present in the cutin layer and thereby become constituents of the extract composition when the composition is formed by the thermal depolymerization methods described herein, but that the production of these products is suppressed or inhibited when cutin depolymerization is carried out using other methods (e.g., acidic or basic depolymerization). Or, the unsaturated products may be generated as part of the thermal depolymerization process.

In some implementations, it is preferable that the direct products (e.g., 200, 202, 204, 206, 208, and/or 210) of the cutin depolymerization be present in the second mixture but not the indirect unsaturated byproducts (e.g., 302, 304, 306, 308, 310, 312, 314, 316, 318, and/or products of Formula II) resulting from the decomposition (e.g., elimination) of the direct products. For example, when the resulting second mixture is subsequently used to form a protective coating, in many cases the coating can have desirable qualities (e.g., higher cross-link density, lower permeability to water and/or oxygen) when the second mixture includes a large fraction of saturated depolymerization products (e.g., 200, 202, 204, 206, 208, and/or 210) while having as small a concentration as possible of the unsaturated indirect byproducts (e.g., 302, 304, 306, 308, 310, 312, 314, 316, 318, and/or products of Formula II). As such, the conditions of the thermal depolymerization process (e.g., solvent composition, temperature, pressure, residence time of the mixture at high temperature and pressure, and time to heat and cool the mixture) can be adjusted such that the mixture after depolymerization includes a large fraction of the direct products, such as monomers 200, 202, 204, 206, 208, and/or 210 (and optionally oligomers formed thereof).

In some implementations, the conversion (by mass) of cutin to cutin-derived monomer and/or oligomer units or esters (both direct products and indirect byproducts) using depolymerization processes described herein can be at least 5%, at least 10%, at least 20%, at least 30%, at least 40%, at least 50%, at least 60%, at least 70%, at least 80%, at least 90%, or at least 95%. Furthermore, of the resulting monomer and/or oligomer and/or ester depolymerization products (both direct products and indirect byproducts), at least 50%, at least 60%, at least 70%, at least 80%, at least 90%, or at least 95% can be direct products such as monomers 200 and/or 202 (and/or oligomers formed thereof). The depolymerization products can be further purified, for example by selective filtering, to form a plant extract composition suitable for coating applications that is a substantially pure composition of direct depolymerization products such as monomers 200, 202, 204, 206, 208, and/or 210 (and/or oligomers formed thereof), or of esterified or glycerated compounds formed of the direct depolymerization products.

The duration of time for which the mixture is held at elevated temperature and pressure during the thermal depolymerization process can be at least partially determined by the specific values of the elevated temperature and pressure, as well as the time required to heat and cool the mixture. Typically, lower temperatures and/or pressures require longer residence times to achieve a high conversion rate of cutin into monomer and/or oligomer units. Thus it may be preferable to use higher temperatures and/or pressures in order to reduce processing times. However, too high a temperature can cause decomposition of the direct monomers/oligomers (e.g., the monomers 200, 202, 204, 206, 208, or 210 of FIGS. 2A-2F, respectively) into other byproducts, as previously described (e.g., in FIG. 3), which in many cases can adversely affect the quality of the coatings that are subsequently formed from the plant extract compositions. For example, residence times longer than one hour at 520 K can result in significant quantities of unsaturated product, and the decomposition is further accelerated at even higher temperatures.

Figure 4A:
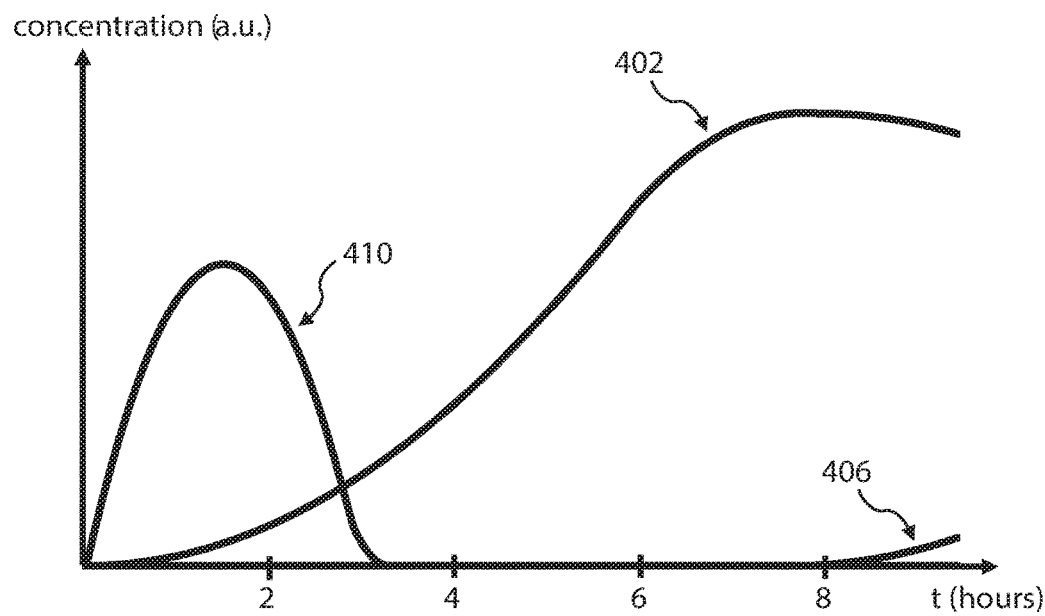
FIGS. 4A and 4B are qualitative plots of the relative concentrations of direct depolymerization products and unsaturated indirect byproducts as a function of time that result from thermal depolymerization of cutin when water is used as the solvent.
Figure 4B:
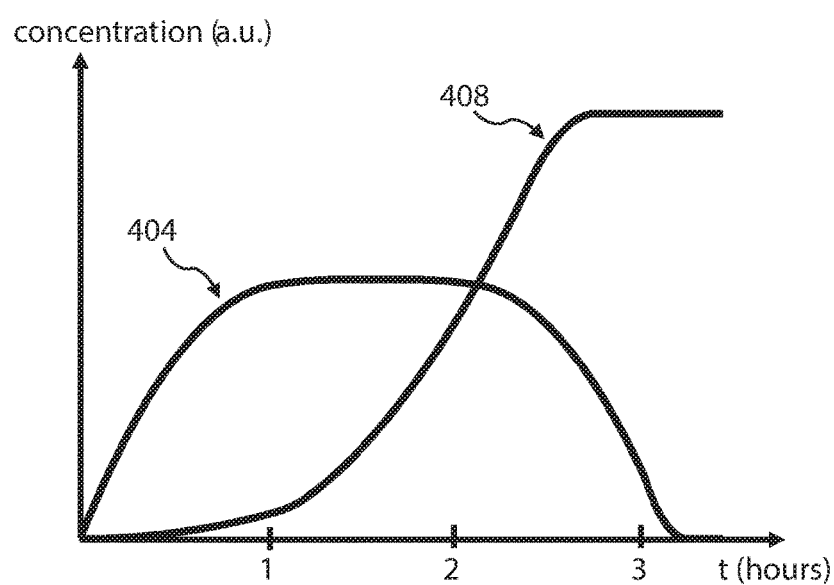

FIGS. 4A and 4B are qualitative plots of the relative concentrations of direct depolymerization products (e.g., 200, 202, 204, 206, 208, and/or 210) and unsaturated indirect byproducts (e.g., 302, 304, 306, 308, 310, 312, 314, 316, and/or 318) in the mixture as a function of time for different thermal depolymerization conditions when water is used as the solvent. FIG. 4A corresponds to a temperature of 498 K and a pressure of about 22.1 atm (about 325 psi), while FIG. 4B corresponds to a temperature of 523 K and a pressure of about 37.4 atm (about 550 psi). In both cases, the cutin was obtained from tomato skins. 402 and 404 represent the relative concentrations of direct depolymerization monomer products (e.g., monomers of 200, 202, 204, 206, 208, and/or 210) in the mixtures at different times during the thermal depolymerization process, while 406 and 408 represent the relative concentrations of indirect unsaturated byproducts (e.g., 302, 304, 306, 308, 310, 312, 314, 316, and/or 318) in the mixtures at different times during the thermal depolymerization process.

As seen in FIGS. 4A and 4B, under both conditions there is no substantial concentration of direct or indirect depolymerization products in the mixture at time t=0 (at the onset of the thermal depolymerization process). Referring now to FIG. 4A, at 498 K there is a steady rise in the concentration of direct depolymerization monomer products with time until the concentration saturates after nearly 8 hours (see 402). However, if the elevated temperature is maintained beyond about 8 hours, the concentration of direct depolymerization monomer products begins to decrease, corresponding to decomposition of the direct depolymerization monomer products into the unsaturated byproducts. Accordingly, at 498 K the concentration of unsaturated byproducts remains low until about 8 hours, at which point it begins to rise as the direct depolymerization monomer products begin to decompose (see 406).

Referring now to FIG. 4B, at 523 K the concentration of direct depolymerization monomer products rises steadily and then saturates after about 1 hour (see 404). Soon after, the concentration of direct depolymerization monomer products begins to decrease, as the direct depolymerization monomer products begin to decompose into the unsaturated byproducts. Correspondingly, at 523 K the concentration of unsaturated byproducts remains low until close to about 1 hour, at which point it begins to rise as the direct depolymerization monomer products begin to decompose (see 408). For times greater than about 2 hours at 523 K, the concentration of unsaturated byproducts increases to a value greater than that of the direct depolymerization monomer products. As such, at 498 K and 22.1 atm in water, substantial conversion of cutin derived from tomato skins to monomers occurs over the course of about 8 hours, but at 523 K and 37.4 atm, the conversion takes less than 1 hour.

Also illustrated qualitatively in FIG. 4A is the concentration of oligomers (n-mers) with 1<n<10 as a function of time (410). As seen, initially the oligomer concentration rises at a much faster rate than the monomer concentration. However, after a time much less than 8 hours, the oligomer concentration saturates and then decreases to a value much less than the monomer concentration. Without wishing to be bound by theory, it is believed that at 498 K and 22.1 atm in water, the cutin is initially being broken down primarily into oligomer units (n-mers with 1<n<10), and the oligomer units are subsequently broken down into monomer units.

The rate of decomposition of the direct monomer/oligomer products (e.g., 200, 202, 204, 206, 208, or 210 in FIGS. 2A-2F, respectively) into unsaturated byproducts such as those of FIGS. 3A-3I at higher temperatures and/or pressures is further affected by the rate of heating and/or cooling to and from the elevated temperature. In some embodiments, longer heating and/or cooling times can result in a higher rate of monomer/oligomer decomposition into unsaturated byproducts for a given residence time at a specific elevated temperature and pressure. As such, in order to prevent or suppress this decomposition, it can be preferable to heat and cool the mixture as quickly as possible. For instance, in some implementations heating and cooling rates greater than 10° C./min, greater than 20° C./min, or greater than 40° C./min are preferred, with faster rates being more preferable.

Other methods for subjecting the mixtures to elevated temperature and/or pressure can be used as well. In particular, methods which minimize the temperature rise and fall times can be preferable, since they can reduce the rate of decomposition of the monomers/oligomers at higher temperatures and/or pressures and allow for better process control. For example, a slurry feed or continuous flow process can be used, in which the mixture is continuously flowed into and then out of the vessel through a series of valves through which the mixture can flow, while at the same time allowing for control of the temperature and pressure within the vessel. Or, dielectric heating could also be used to heat the mixtures.

Figure 5A:
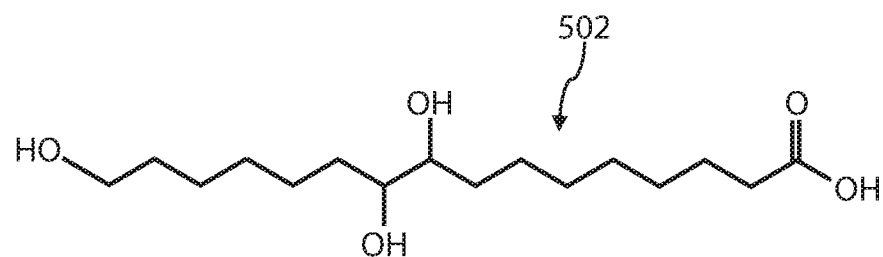
FIGS. 5A, 5B and 5C are chemical compositions of molecules that can be formed from unsaturated indirect byproducts of thermal depolymerization of cutin.
Figure 5B:
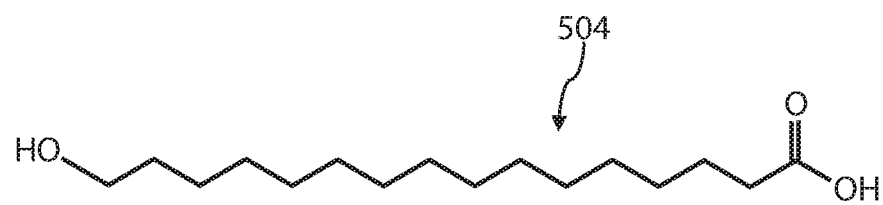
Figure 5C:
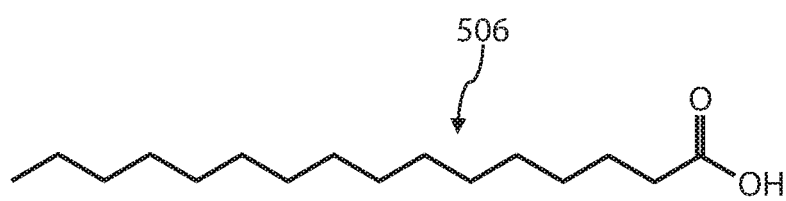

In some implementations, it may be preferable for some percentage (e.g., greater than 20%, greater than 40%, greater than 60%, greater than 70%, greater than 80%, or greater than 90%) of the direct depolymerization products (e.g., monomers 200, 202, 204, 206, 208, and/or 210 of FIGS. 2A-2F, respectively) to decompose into other monomer/oligomer byproducts (e.g., unsaturated byproducts 302, 304, 306, 308, 310, 312, 314, 316, and 318 of FIGS. 3A-3I, respectively) that do not typically result from the depolymerization of cutin (or cutin-containing components). Specifically, the unsaturated byproducts 302, 304, 306, 308, 310, 312, 314, 316, and 318 of FIGS. 3A-3I, respectively, as well as the compounds of Formula II, can each be isolated and further processed to form other saturated molecules such as those shown in FIGS. 5A, 5B, and 5C, where FIG. 5A illustrates 9,10,16-trihydroxyhexadecanoic acid (502), FIG. 5B illustrates 16-hydroxyhexadecanoic acid (504), and FIG. 5C illustrates palmitic acid (506). Similarly, unsaturated ester byproducts, such as those shown in FIGS. 7A-7I, 8A-8I, 9A-9I, and 10A-10I and described in further detail below, can each be isolated and further processed to form other saturated molecules such as those shown in FIGS. 6A-6H (which are also described in further detail below). For example, referring to FIG. 4B, the reaction to convert the saturated monomers to unsaturated byproducts can be driven to completion, for example by carrying out the thermal depolymerization process at 523 K and 37.4 atm in water for times greater than 2 hours. The unsaturated byproducts can then be hydrogenated with a catalyst, for example Ni or Pd, to form palmitic acid 506 or 16-hydroxyhexadecanoic acid 504. Accordingly, in such a process, palmitic acid can be formed from non-palm sources. The production of palm oil from oil palms has a large environmental impact, including deforestation and habitat loss, as well as sociological impacts, since indigenous people are often displaced to make room for large plantations in the developing world. For these reasons, it can be desirable to obtain palmitic acid from non-palm sources.

Alternatively, after the reaction to convert the saturated monomers to unsaturated byproducts is driven to completion, the unsaturated byproducts can be hydroxylated with a catalyst (e.g., osmium tetraoxide or another hydroxylation reagent) to form, for instance, 9,10,16-trihydroxyhexadecanoic acid (502) or other compounds of Formula I, where Formula I is as previously defined.

Plant extract compositions for forming protective coatings can subsequently be formed from any of the molecules 200, 202, 204, 206, 208, 210, 502, 504, or 506 in FIGS. 2A, 2B, 2C, 2D, 2E, 2F, 5A, 5B, and 5C, respectively, as well as any other direct depolymerization products (e.g., compounds of Formula I). The coatings can each be formed primarily from one of these types of molecules, or alternatively from a combination of these molecules. Alternatively, the molecules can first be esterified (e.g., glycerated to form 1-monoacyglycerides and/or 2-monoacylglycerides), the plant extract compositions can be formed from the esters or glycerated molecules, and the coatings can be formed from the esters or glycerated molecules in the plant extract compositions. Forming coatings from plant extract compositions formed from molecules 502 or from molecules 504, or from a combination of molecules 200, 202, 204, 206, 208, 210, 502, 504, and 506, or from esters or glycerated molecules formed thereof, can allow for further control over the properties of both the extract compositions and the coatings. For example, the solubility of molecules 502, 504, and 506 (and esters or glycerated molecules formed thereof) in various solvents is different than that for molecules 200, 202, 204, 206, 208, and 210, (and esters or glycerated molecules formed thereof). As such, a wider variety of solvents may be available for use in forming plant extract compositions from molecules 502, 504, or 506 (or esters or glycerated molecules formed thereof), or from combinations of molecules 200, 202, 204, 206, 208, 210, 502, 504, and 506 (or esters or glycerated molecules formed thereof), than can be used for plant extract compositions which only include substantial quantities of direct byproducts of cutin depolymerization (e.g., molecules 200, 202, 204, 206, 208, and/or 210, or esters or glycerated molecules formed thereof). Furthermore, properties of the coatings formed from the plant extract can further be tailored for specific applications using molecules 502, 504, and 506 (and/or esters or glycerated molecules formed thereof), either alone or in combination with molecules 200, 202, 204, 206, 208, 210, and/or one another. For example, the crosslink density of the resulting protective films can vary depending on the percent mass of each of molecules 200, 202, 204, 206, 208, 210, 502, 504, and 506 (and/or esters or glycerated molecules formed thereof) in the plant extract compositions, that can allow for film properties such as density and permeability to be specifically tailored for the specific application in which the film is used. Furthermore, these molecules can be chemically modified in order to tailor their properties, e.g., solubility, stability, and film forming properties.

As previously described, in some implementations, the molecules/compounds obtained directly from depolymerization (e.g., compounds 200, 202, 204, 206, 208, or 210,) or indirectly through subsequent processing steps (e.g., compounds 502, 504, or 506) are glycerated to form 1-monoacylclyceride and/or 2-monoacylglyceride monomers, oligomers formed thereof, or combinations. In this case, the plant extract compositions from which protective coatings are subsequently formed include the 1-monoacylclycerides and/or 2-monoacylglycerides optionally dissolved in a solvent. The difference between a 1-monoacylclyceride and a 2-monoacylglyceride is the point of connection of the glyceride group. Protective coatings formed over substrates such as fruits from formulations that include combinations of 2-monoacylglycerides and 1-monoacylclycerides (or optionally a different additive in place of the 1-monoacylclycerides) have in many cases been found by the inventors of the disclosure to exhibit superior performance in preventing water loss and oxidation without altering the physical appearance of the substrate.

While esters (e.g., glyceryl esters) of direct depolymerization products 200 or 202 can be formed via esterification (e.g., Fischer esterification) following the thermal depolymerization processes described herein, esters can alternatively be directly formed during the thermal depolymerization processes through suitable solvent selection. For example, when the thermal depolymerization of cutin is carried out in water, the resulting direct depolymerization products can be free fatty acids (e.g., compounds 200, 202, 204, 206, 208, or 210 of FIGS. 2A-2F). However, thermal depolymerization of cutin in other solvents (e.g., ethanol, methanol, or glycerol) can directly result in the production of esters.

Figure 6A:
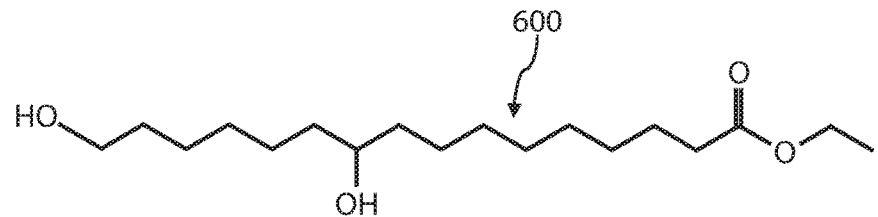
FIGS. 6A and 6B are esters that can be formed by thermal depolymerization of cutin in a solvent that includes ethanol.
Figure 6B:
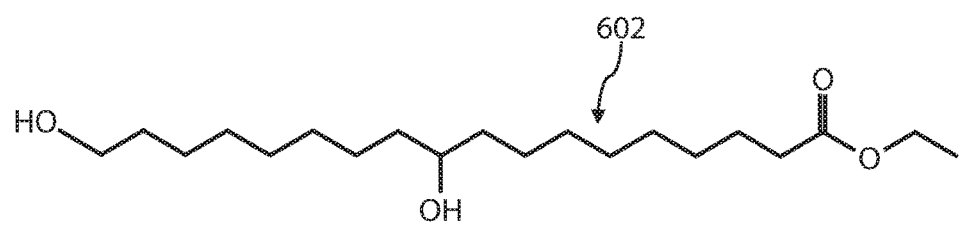

For example, FIGS. 6A and 6B show the chemical structure of ethyl 10,16-dihydroxyhexadecanoate 600 and ethyl 10,18-dihydroxyoctadecanoate 602, respectively, which are ethyl esters of respective compounds 10,16-dihydroxyhexadecanoic acid (200 in FIG. 2A) and 10,18-dihydroxyoctadecanoic acid (202 in FIG. 2B). Compounds 600 and/or 602 can be produced directly by carrying out the thermal depolymerization of cutin in ethanol, or alternatively by carrying out the thermal depolymerization process in a solvent that includes ethanol, for example water with ethanol added as a co-solvent.

Figure 6C:
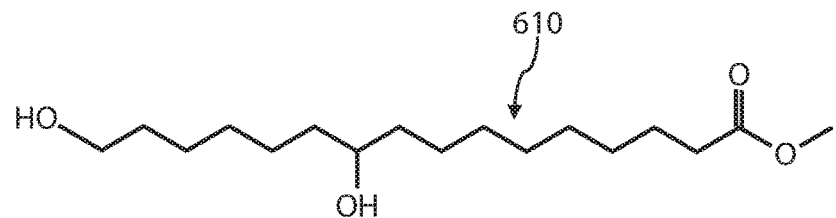
FIGS. 6C and 6D are esters that can be formed by thermal depolymerization of cutin in a solvent that includes methanol.
Figure 6D:
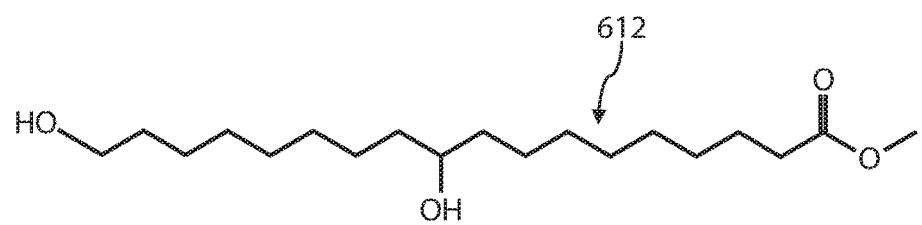
Figure 6E:
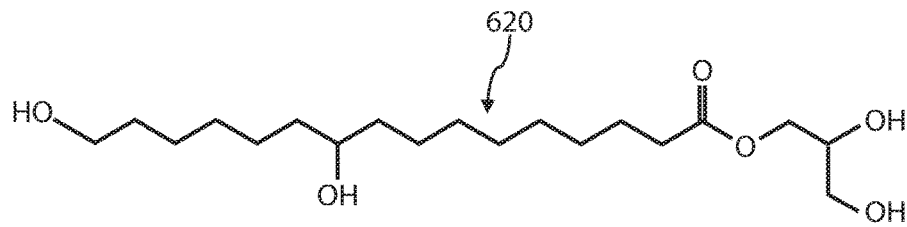
FIGS. 6E, 6F, 6G, and 6H are esters that can be formed by thermal depolymerization of cutin in a solvent that includes glycerol.
Figure 6F:
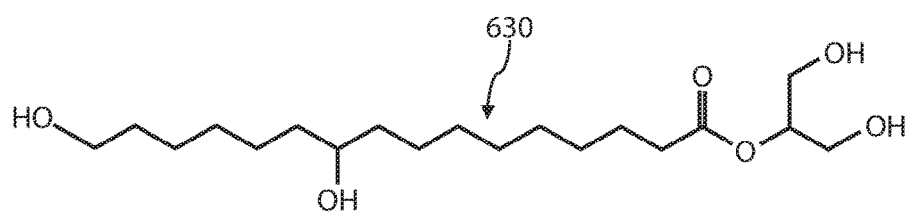
Figure 6G:
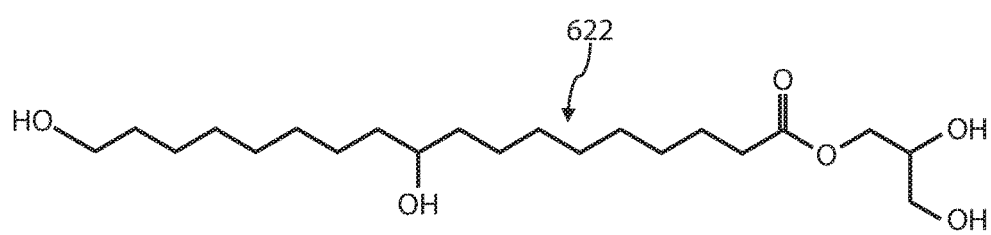
Figure 6H:
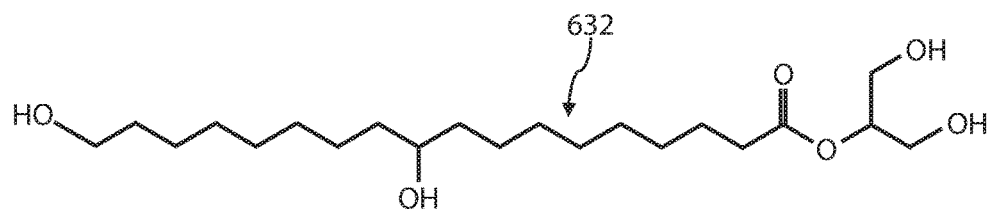

As another example, FIGS. 6C and 6D show the chemical structure of methyl 10,16-dihydroxyhexadecanoate 610 and methyl 10,18-dihydroxyoctadecanoate 612, respectively, which are methyl esters of respective compounds 10,16-dihydroxyhexadecanoic acid (200 in FIG. 2A) and 10,18-dihydroxyoctadecanoic acid (202 in FIG. 2B). Compounds 610 and/or 612 can be produced directly by carrying out the thermal depolymerization of cutin in methanol, or alternatively by carrying out the thermal depolymerization process in a solvent that includes methanol, for example in water with methanol added as a co-solvent.

As yet another example, FIGS. 6E, 6F, 6G and 6H show the chemical structure of 2,3-dihydroxypropyl 10,16-dihydroxyhexadecanoate 620, 1,3-dihydroxypropan-2-yl 10,16-dihydroxyhexadecanoate 630, 2,3-dihydroxypropyl 10,18-dihydroxyoctadecanoate 622, and 1,3-dihydroxypropan-2-yl 10,18-dihydroxyoctadecanoate 632, respectively. Compounds 620 and 630 are glyceryl esters of 10,16-dihydroxyhexadecanoic acid (200 in FIG. 2A), and compounds 622 and 632 are glyceryl esters of 10,18-dihydroxyoctadecanoic acid (202 in FIG. 2B). Compounds 620, 630, 622, and/or 632 can be produced directly by carrying out the thermal depolymerization of cutin in glycerol, or alternatively by carrying out the thermal depolymerization process in a solvent that includes glycerol, for example in water with glycerol added as a co-solvent.

Esters of unsaturated byproducts (e.g., compounds 302, 304, 306, 308, 310, 312, 314, 316, and 318 in FIGS. 3A-3I) can also be formed via esterification (e.g., Fischer esterification) following the thermal depolymerization processes described herein. For example, referring to FIG. 4B, the thermal process to convert saturated monomers to unsaturated byproducts (302, 304, 306, 308, 310, 312, 314, 316, and/or 318) can be driven to completion, for example by carrying out the thermal depolymerization of cutin at 523 K and 37.4 atm in water for times greater than 2 hours, and the unsaturated byproducts can then be esterified. Alternatively, similar to the processes described above for direct formation of esters 600, 602, 610, 612, 620, 622, 630, and 632, esters of unsaturated byproducts can be directly formed during the thermal depolymerization processes through suitable solvent selection. Specifically, when the thermal depolymerization of cutin is carried out in water, the resulting unsaturated byproducts can be unsaturated fatty acids (e.g., compounds 302, 304, 306, 308, 310, 312, 314, 316, and/or 318). However, thermal depolymerization of cutin in other solvents (e.g., ethanol, methanol, or glycerol) can directly result in the production of unsaturated fatty esters.

Figure 7A:
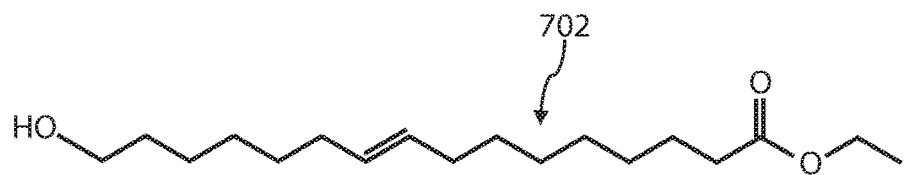
FIGS. 7A, 7B, 7C, 7D, 7E, 7F, 7G, 7H, and 7I are esters that can be formed by thermal depolymerization of cutin in a solvent that includes ethanol.
Figure 7B:
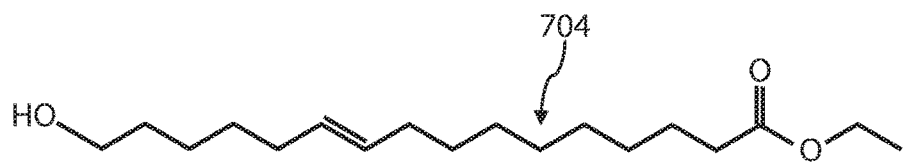
Figure 7C:
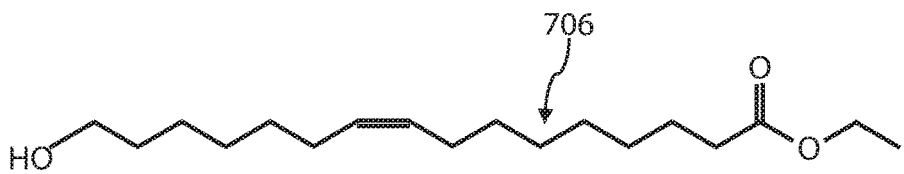
Figure 7D:
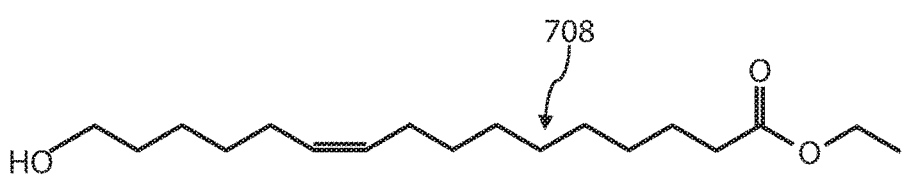
Figure 7E:
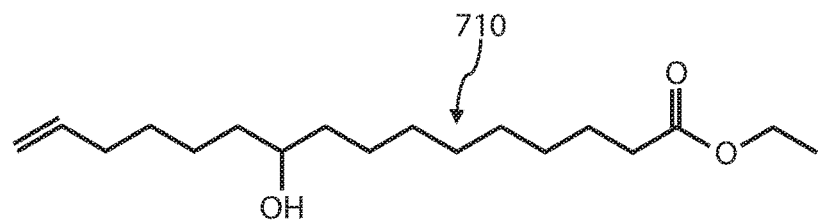
Figure 7F:
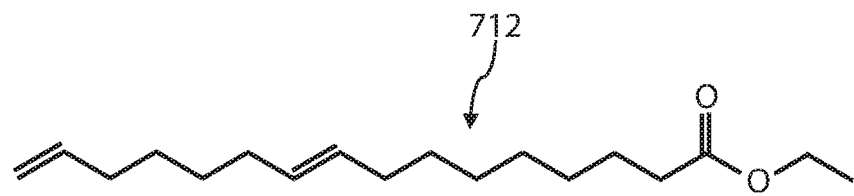
Figure 7G:
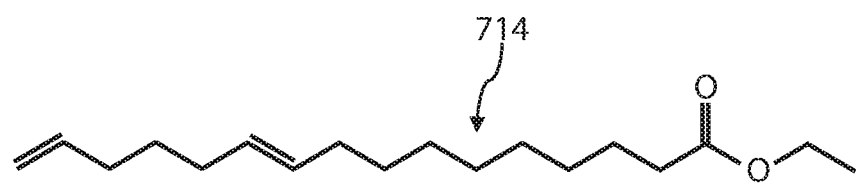
Figure 7H:
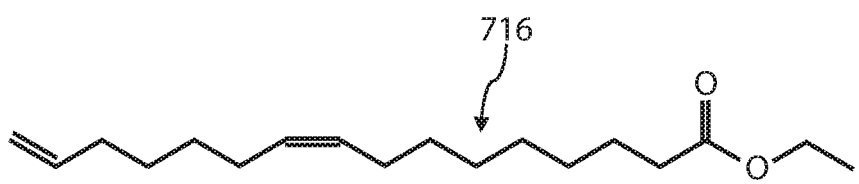
Figure 7I:
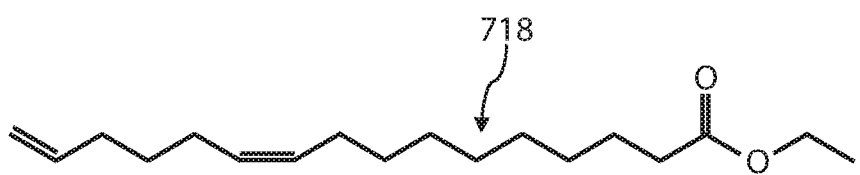

For example, FIG. 7A shows the chemical structure of ethyl (E)-16-hydroxyhexadec-9-enoate 702, FIG. 7B shows the chemical structure of ethyl (E)-16-hydroxyhexadec-10-enoate 704, FIG. 7C shows the chemical structure of ethyl (Z)-16-hydroxyhexadec-9-enoate 706, FIG. 7D shows the chemical structure of ethyl (Z)-16-hydroxyhexadec-10-enoate 708, FIG. 7E shows the chemical structure of ethyl 10-hydroxyhexadec-15-enoate 710, FIG. 7F shows the chemical structure of ethyl (E)-hexadeca-9,15-dienoate 712, FIG. 7G shows the chemical structure of ethyl (E)-hexadeca-10,15-dienoate 714, FIG. 7H shows the chemical structure of ethyl (Z)-hexadeca-9,15-dienoate 716, and FIG. 7I shows the chemical structure of ethyl (Z)-hexadeca-10,15-dienoate 718. Compound 702 is an ethyl ester of compound 302, compound 704 is an ethyl ester of compound 304, compound 706 is an ethyl ester of compound 306, compound 708 is an ethyl ester of compound 308, compound 710 is an ethyl ester of compound 310, compound 712 is an ethyl ester of compound 312, compound 714 is an ethyl ester of compound 314, compound 716 is an ethyl ester of compound 316, and compound 718 is an ethyl ester of compound 318. Compounds 702, 704, 706, 708, 710, 712, 714, 716 and/or 718 can be produced directly by carrying out the thermal depolymerization of cutin in ethanol at a sufficiently high temperature for a sufficiently long time, or alternatively by carrying out the thermal depolymerization process in a solvent that includes ethanol, for example water with ethanol added as a co-solvent.

Figure 8A:
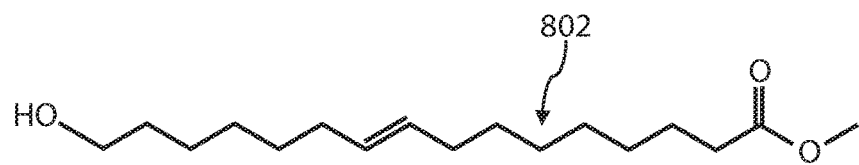
FIGS. 8A, 8B, 8C, 8D, 8E, 8F, 8G, 8H, and 8I are esters that can be formed by thermal depolymerization of cutin in a solvent that includes methanol.
Figure 8B:
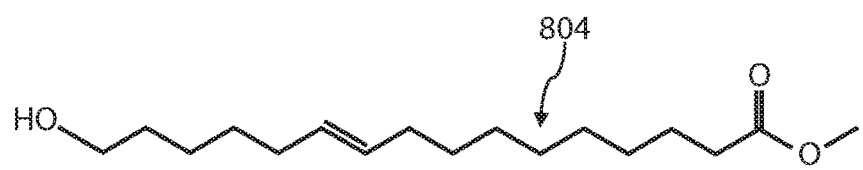
Figure 8C:
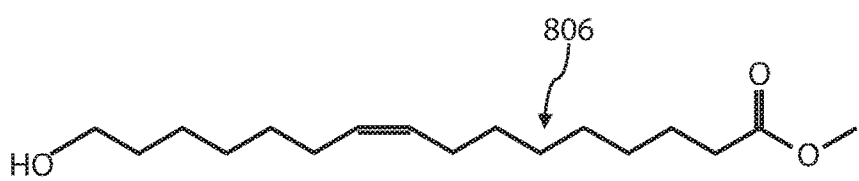
Figure 8D:
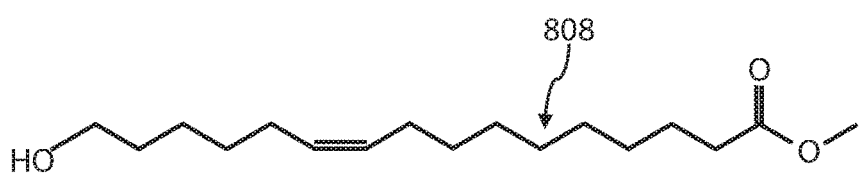
Figure 8E:
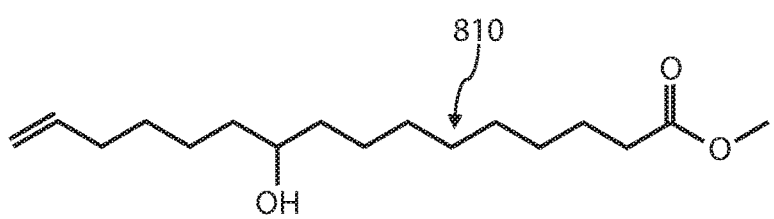
Figure 8F:
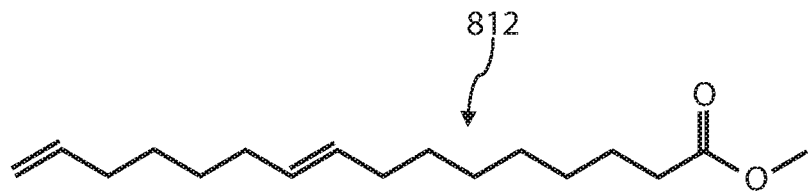
Figure 8G:
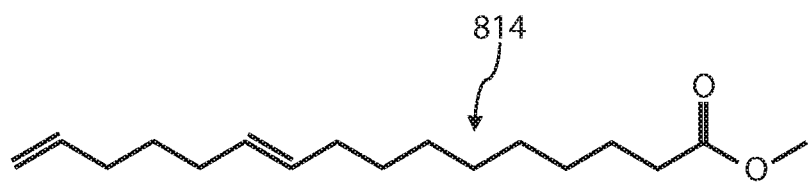
Figure 8H:
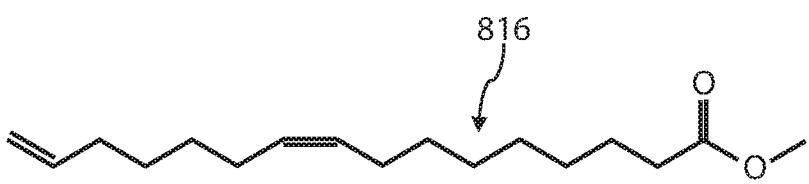
Figure 8I:
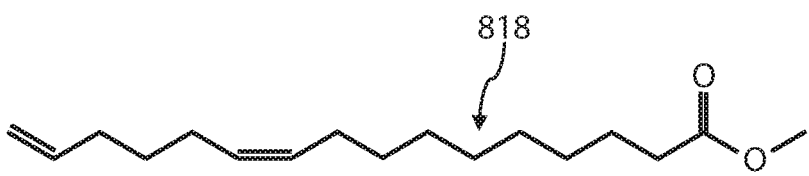

As another example, FIG. 8A shows the chemical structure of methyl (E)-16-hydroxyhexadec-9-enoate 802, FIG. 8B shows the chemical structure of methyl (E)-16-hydroxyhexadec-10-enoate 804, FIG. 8C shows the chemical structure of methyl (Z)-16-hydroxyhexadec-9-enoate 806, FIG. 8D shows the chemical structure of methyl (Z)-16-hydroxyhexadec-10-enoate 808, FIG. 8E shows the chemical structure of methyl 10-hydroxyhexadec-15-enoate 810, FIG. 8F shows the chemical structure of methyl (E)-hexadeca-9,15-dienoate 812, FIG. 8G shows the chemical structure of methyl (E)-hexadeca-10,15-dienoate 814, FIG. 8H shows the chemical structure of methyl (Z)-hexadeca-9,15-dienoate 816, and FIG. 8I shows the chemical structure of methyl (Z)-hexadeca-10,15-dienoate 818. Compound 802 is a methyl ester of compound 302, compound 804 is a methyl ester of compound 304, compound 806 is a methyl ester of compound 306, compound 808 is a methyl ester of compound 308, compound 810 is a methyl ester of compound 310, compound 812 is a methyl ester of compound 312, compound 814 is a methyl ester of compound 314, compound 816 is a methyl ester of compound 316, and compound 818 is a methyl ester of compound 318. Compounds 802, 804, 806, 808, 810, 812, 814, 816 and/or 818 can be produced directly by carrying out the thermal depolymerization of cutin in methanol at a sufficiently high temperature for a sufficiently long time, or alternatively by carrying out the thermal depolymerization process in a solvent that includes methanol, for example water with methanol added as a co-solvent.

Figure 9A:
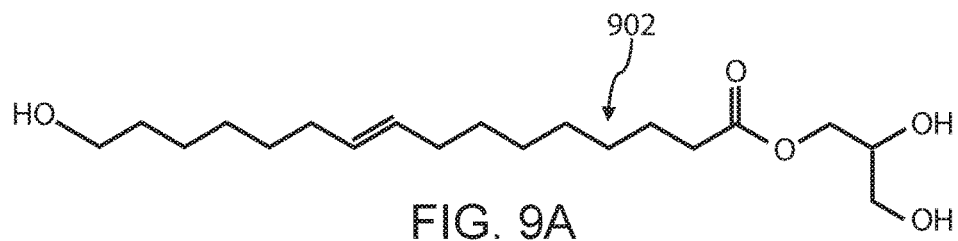
FIGS. 9A, 9B, 9C, 9D, 9E, 9F, 9G, 9H, and 9I are esters that can be formed by thermal depolymerization of cutin in a solvent that includes glycerol.
Figure 9B:
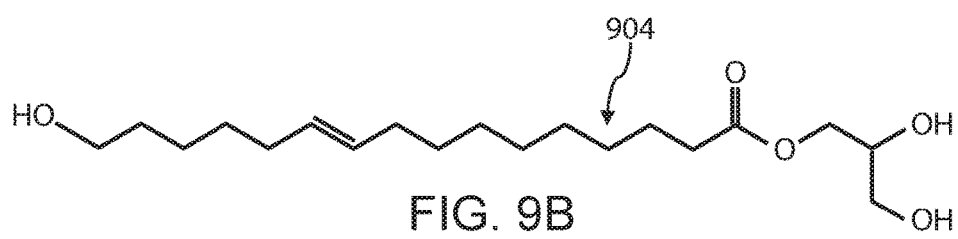
Figure 9C:
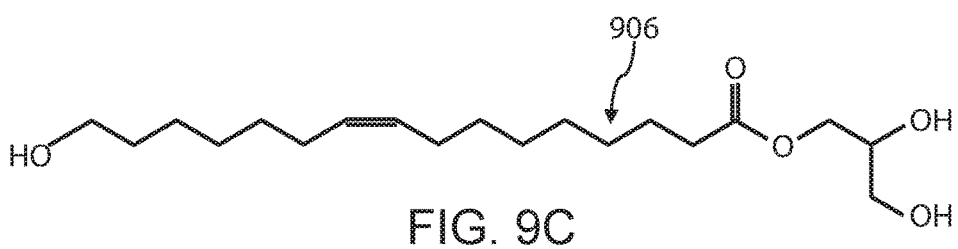
Figure 9D:
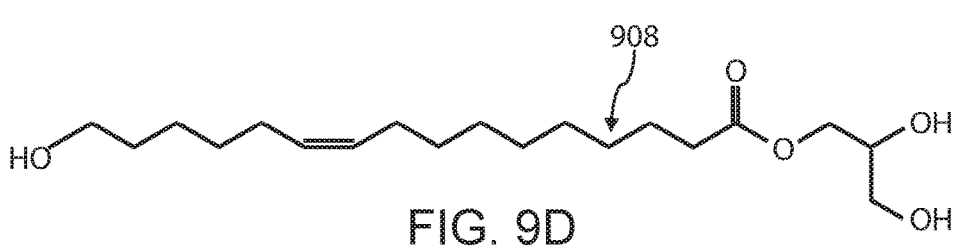
Figure 9E:
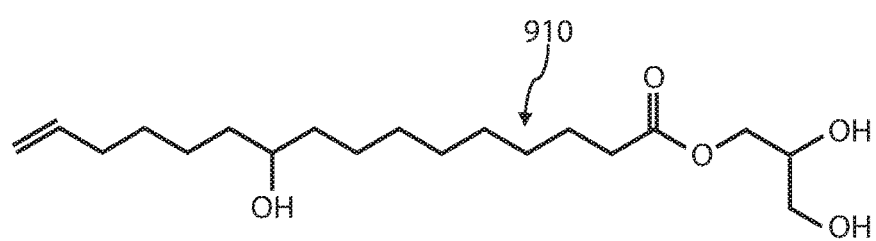
Figure 9F:
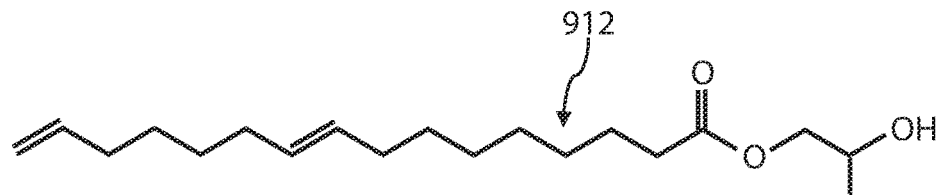
Figure 9G:
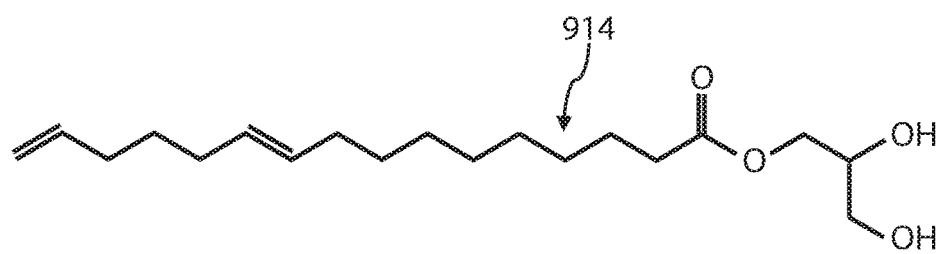
Figure 9H:
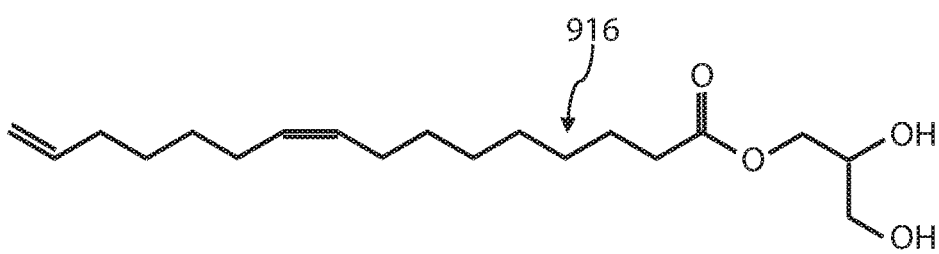
Figure 9I:
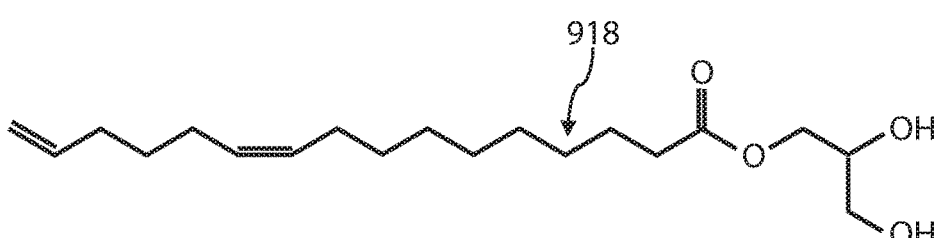

As yet another example, FIG. 9A shows the chemical structure of 2,3-dihydroxypropyl (E)-16-hydroxyhexadec-9-enoate 902, FIG. 9B shows the chemical structure of 2,3-dihydroxypropyl (E)-16-hydroxyhexadec-10-enoate 904, FIG. 9C shows the chemical structure of 2,3-dihydroxypropyl (Z)-16-hydroxyhexadec-9-enoate 906, FIG. 9D shows the chemical structure of 2,3-dihydroxypropyl (Z)-16-hydroxyhexadec-10-enoate 908, FIG. 9E shows the chemical structure of 2,3-dihydroxypropyl 10-hydroxyhexadec-15-enoate 910, FIG. 9F shows the chemical structure of 2,3-dihydroxypropyl (E)-hexadeca-9,15-dienoate 912, FIG. 9G shows the chemical structure of 2,3-dihydroxypropyl (E)-hexadeca-10,15-dienoate 914, FIG. 9H shows the chemical structure of 2,3-dihydroxypropyl (Z)-hexadeca-9,15-dienoate 916, and FIG. 9I shows the chemical structure of 2,3-dihydroxypropyl (Z)-hexadeca-10,15-dienoate 918. Compound 902 is a glyceryl ester of compound 302, compound 904 is a glyceryl ester of compound 304, compound 906 is a glyceryl ester of compound 306, compound 908 is a glyceryl ester of compound 308, compound 910 is a glyceryl ester of compound 310, compound 912 is a glyceryl ester of compound 312, compound 914 is a glyceryl ester of compound 314, compound 916 is a glyceryl ester of compound 316, and compound 918 is a glyceryl ester of compound 318.

Figure 10A:
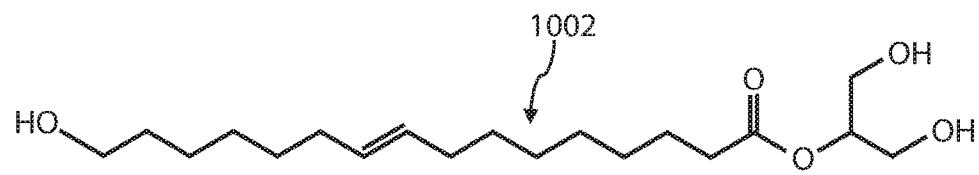
FIGS. 10A, 10B, 10C, 10D, 10E, 10F, 10G, 10H, and 10I are esters that can be formed by thermal depolymerization of cutin in a solvent that includes glycerol.
Figure 10B:
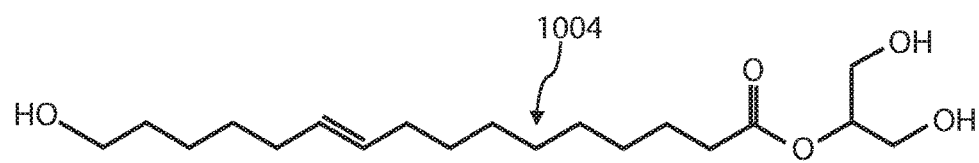
Figure 10C:
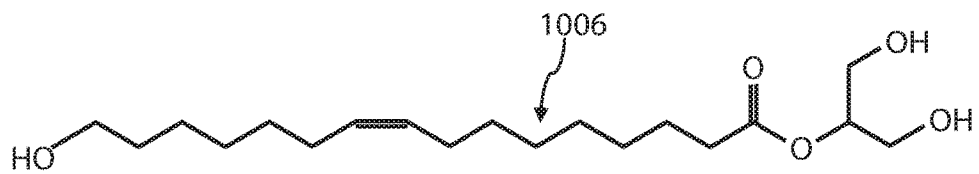
Figure 10D:
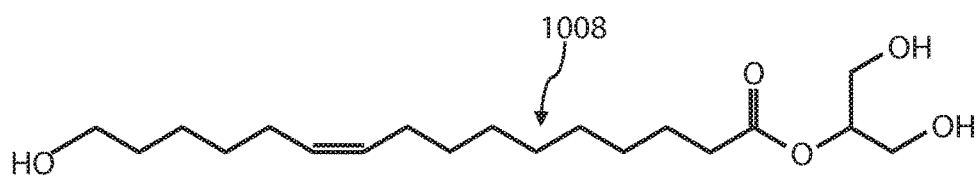
Figure 10E:
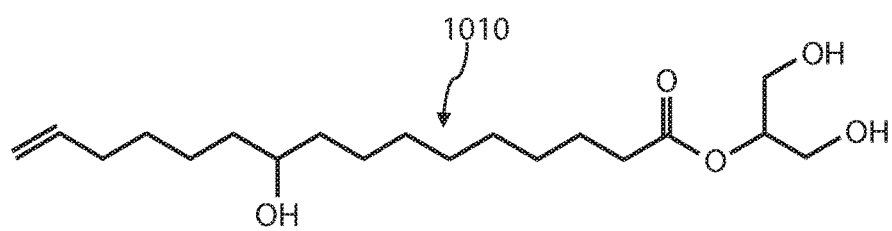
Figure 10F:
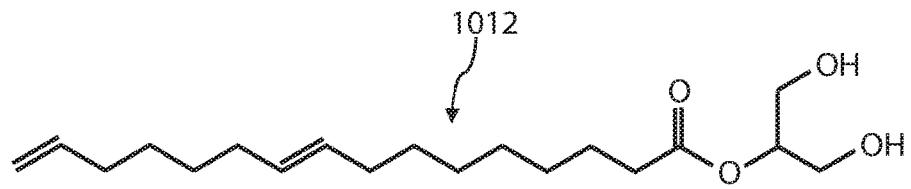
Figure 10G:
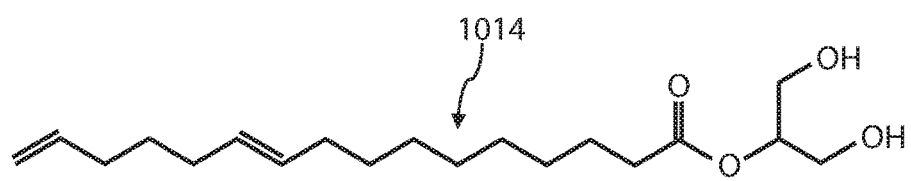
Figure 10H:
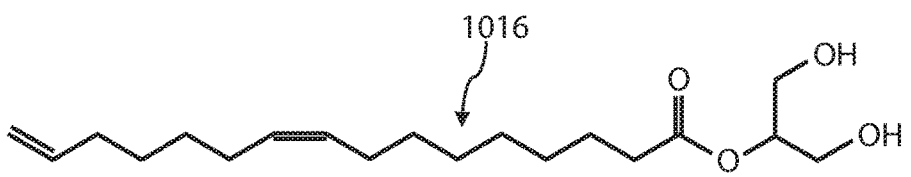
Figure 10I:
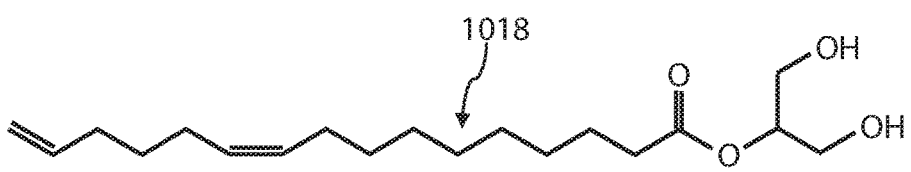

As still another example, FIG. 10A shows the chemical structure of 1,3-dihydroxypropan-2-yl (E)-16-hydroxyhexadec-9-enoate 1002, FIG. 10B shows the chemical structure of 1,3-dihydroxypropan-2-yl (E)-16-hydroxyhexadec-10-enoate 1004, FIG. 10C shows the chemical structure of 1,3-dihydroxypropan-2-yl (Z)-16-hydroxyhexadec-9-enoate 1006, FIG. 10D shows the chemical structure of 1,3-dihydroxypropan-2-yl (Z)-16-hydroxyhexadec-10-enoate 1008, FIG. 10E shows the chemical structure of 1,3-dihydroxypropan-2-yl 10-hydroxyhexadec-15-enoate 1010, FIG. 10F shows the chemical structure of 1,3-dihydroxypropan-2-yl (E)-hexadeca-9,15-dienoate 1012, FIG. 10G shows the chemical structure of 1,3-dihydroxypropan-2-yl (E)-hexadeca-10,15-dienoate 1014, FIG. 10H shows the chemical structure of 1,3-dihydroxypropan-2-yl (Z)-hexadeca-9,15-dienoate 1016, and FIG. 10I shows the chemical structure of 1,3-dihydroxypropan-2-yl (Z)-hexadeca-10,15-dienoate 1018. Compound 1002 is a glyceryl ester of compound 302, compound 1004 is a glyceryl ester of compound 304, compound 1006 is a glyceryl ester of compound 306, compound 1008 is a glyceryl ester of compound 308, compound 1010 is a glyceryl ester of compound 310, compound 1012 is a glyceryl ester of compound 312, compound 1014 is a glyceryl ester of compound 314, compound 1016 is a glyceryl ester of compound 316, and compound 1018 is a glyceryl ester of compound 318. Compounds 902, 904, 906, 908, 910, 912, 914, 916, 918, 1002, 1004, 1006, 1008, 1010, 1012, 1014, 1016, and/or 1018 can be produced directly by carrying out the thermal depolymerization of cutin in glycerol at a sufficiently high temperature for a sufficiently long time, or alternatively by carrying out the thermal depolymerization process in a solvent that includes methanol, for example water with methanol added as a co-solvent.

In some implementations, the solvent of the mixture (i.e., the solvent in which the thermal depolymerization process is carried out) is a liquid at standard temperature and pressure (i.e., about 273K and about 1 atmosphere), but at least partially undergoes a phase change when brought up to the elevated temperature and pressure. For example, in cases where the solvent is water ($H_2O$), if the temperature of the mixture is increased above 647 K and the pressure is increased above 218 atm, the $H_2O$ becomes supercritical and the thermal depolymerization process is carried out in supercritical $H_2O$. Or, in cases where the solvent is ethanol, if the temperature of the mixture is increased above 513.9 K and the pressure is increased above 60.6 atm, the ethanol becomes supercritical and the thermal depolymerization process is carried out in supercritical ethanol.

Because the cutin obtained from the cutin-containing portion is typically intermixed with many of the other constituents previously described, the extract obtained from the thermal depolymerization process may have a higher level of impurity constituents than can be tolerated in agricultural coating applications. As such, the cutin can be purified by selectively removing or filtering out the impurity constituents. Selective filtering can occur either before or after the depolymerization process, or both before and after depolymerization. Selective filtering may include one or more of the following processes:

(a) Prior to depolymerizing or partly depolymerizing the cutin, washing and/or heating the cutin in a selective solvent for which the solubility of impurity constituents in the selective solvent is higher than the solubility of the cutin. In this case, impurities are dissolved into the selective solvent, thereby resulting in fewer impurities in the first intermediate extract immediately after depolymerization. Examples of such a solvent can include chloroform, diethyl ether, dichloromethane, hexane, petroleum ether, ethyl acetate, acetone, isopropanol, ethanol, methanol, supercritical carbon dioxide, supercritical water, water, and mixtures thereof.

(b) After depolymerizing or partly depolymerizing the cutin to obtain the second mixture comprising a first intermediate extract including the depolymerization products in the solvent, washing and/or heating the first intermediate extract in a selective solvent (e.g., heptane, ethyl acetate, acetonitrile, etc.) for which the solubility of impurity constituents in the selective solvent is lower than the solubility of the monomers and/or oligomers. In this case, the monomers and/or oligomers are dissolved into the selective solvent while the impurities are not. The impurities can then be filtered out, resulting in a second intermediate extract dissolved in the selective solvent, whereby the second intermediate extract has a higher purity than the first intermediate extract. The second intermediate extract may subsequently be solidified, e.g., by evaporating the selective solvent.

(c) After depolymerizing or partly depolymerizing the cutin to obtain the second mixture comprising a first intermediate extract including the depolymerization products in the solvent, washing and/or heating the first intermediate extract in a selective solvent (e.g., chloroform or hexane) for which the solubility of impurity constituents in the selective solvent is higher than the solubility of the monomers and/or oligomers. In this case, impurities are dissolved into the selective solvent, thereby removing the impurities from the extract, and a second intermediate extract having a higher purity than the first intermediate extract is obtained.

(d) After obtaining a compound comprising cutin from a cutin-containing portion of plant matter and prior to depolymerizing or partly depolymerizing the cutin, exposing the compound to supercritical carbon dioxide to selectively reduce a concentration of at least one of, for instance, proteins, polysaccharides, phenols, lignans, aromatic acids, terpenoids, flavonoids, carotenoids, alkaloids, alcohols, alkanes, aldehydes, waxes, and uncharacterized colored impurities.

(e) After depolymerizing or partly depolymerizing the cutin to obtain the second mixture comprising a first intermediate extract including the depolymerization products in the solvent, adding a second solvent to the mixture, wherein the first and second solvents are immiscible, the second solvent having the property that either the impurities or the monomers/oligomers (but not both) selectively segregate into the second solvent over the first solvent.

(f) After depolymerizing or partly depolymerizing the cutin to obtain the second mixture comprising a first intermediate extract including the depolymerization products dissolved in the solvent, causing the monomers/oligomers to crystallize and filtering them from the mixture, or alternatively causing the impurities to crystallize and filtering them from the mixture.

Figure 11:
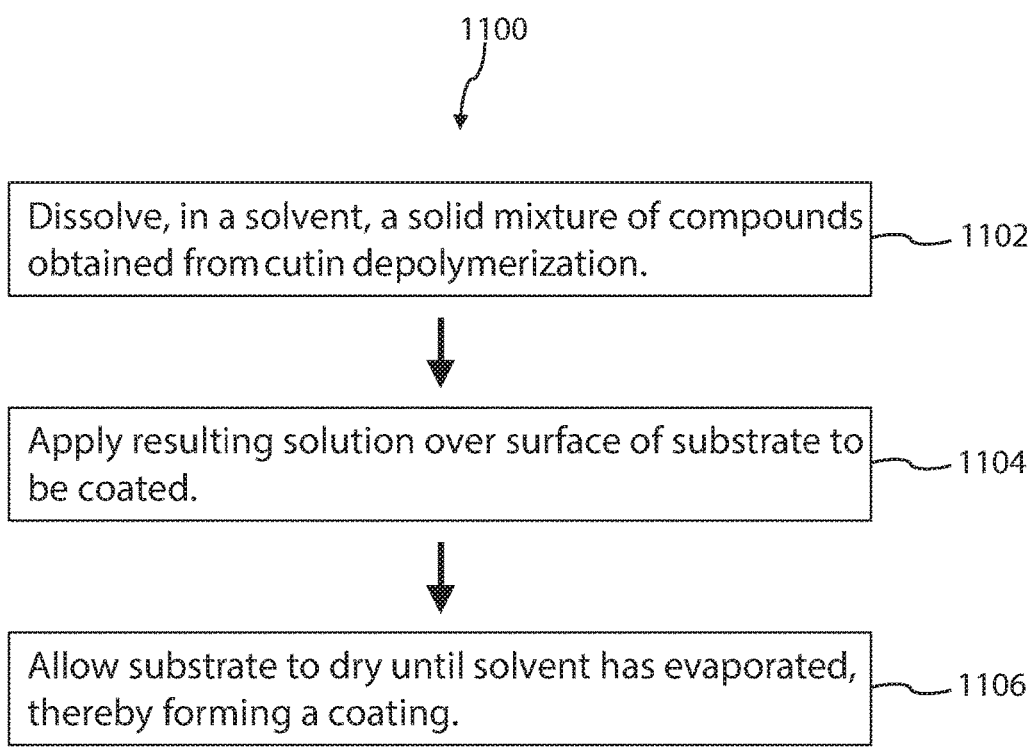
FIG. 11 illustrates a process for forming a protective coating.

A protective coating can be formed from the plant extract compositions described above using the process 1100 illustrated in FIG. 11. First, a solid mixture of the monomer and/or oligomer units is dissolved in a solvent (e.g., water, ethanol, or combinations thereof) to form the plant extract composition (step 1102). The concentration of the solid mixture in the solvent can, for example, be in a range of about 0.1 to 100 mg/mL. Next, the solution which includes the monomer and/or oligomer units is applied over the surface of the substrate to be coated (step 1104), for example by spray coating the substrate or by dipping the substrate in the solution. In the case of spray coating, the solution can, for example, be placed in a spray bottle which generates a fine mist spray. The spray bottle head can then be held approximately six to twelve inches from the substrate, and the substrate then sprayed. In the case of dip coating, the substrate can, for example, be placed in a bag, the solution containing the composition poured into the bag, and the bag then sealed and lightly agitated until the entire surface of the substrate is wet. After applying the solution to the substrate, the substrate is allowed to dry until all of the solvent has evaporated, thereby allowing a coating composed of the monomer and/or oligomer units to form over the surface of the substrate (step 1106).

The coatings and methods described herein offer a number of distinct features and advantages over current methods of maintaining freshness of agricultural products and food. For instance, the coatings can prevent water loss and shield agricultural products from threats such as bacteria, fungi, viruses and the like. The coatings can also protect, for instance, plants and food products from physical damage (e.g., bruising), water loss, oxidation, and photodamage. Accordingly, the compositions, solutions, and coatings can be used to help store agricultural products for extended periods of time without spoiling. In some instances, the compositions and coatings allow for food to be kept fresh in the absence of refrigeration. The compositions and coatings described herein can also be edible (i.e., the coatings can be non-toxic for human consumption). The methods for forming the coatings described herein can be entirely organic. In some implementations, the coatings are tasteless, colorless, and/or odorless. The coatings can be made from the same chemical feedstocks that are naturally found in the plant cuticle, (e.g., hydroxy and/or dihydroxy palmitic acids, and/or hydroxy oleic and stearic acids) and can thus be organic and all-natural.

In some implementations, a plant extract composition is formed from cutin derived monomers and/or oligomers and/or esters thereof extracted from cutin of a first plant species (e.g., utilizing the thermal depolymerization processes previously described), and the composition is then disposed over plant matter of the same plant species, such that the extracted monomers and/or oligomers and/or esters form a protective coating over the plant matter of the first plant species. Such a coating can, for example, reinforce the cuticle layer that naturally exists over the plant matter. In other implementations, a plant extract composition is formed from cutin derived monomers and/or oligomers and/or esters extracted from cutin of a first plant species (e.g., utilizing the thermal depolymerization processes previously described), and the composition is then disposed over plant matter of a second plant species which is different from (although in some cases could be the same as) the first plant species, such that the extracted monomers and/or oligomers and/or esters form a protective coating over the plant matter of the second plant species. For example, the plant extract composition can be formed from monomers and/or oligomers and/or esters extracted from cutin obtained from tomato or cranberry skins and then applied over strawberries, bananas, finger limes, lemons, or other plant species different from the plant species from which the cutin was obtained in order to form a protective coating. As such, the protective coatings that are formed from the monomers and/or oligomers and/or esters of the plant extract composition can provide forms of protection against biotic and abiotic stressors for which the native cuticle layer of the second plant species is inherently incapable of providing. For example, the protective coatings deposited over the substrates can provide superior protection against water loss and oxidation than can be inherently provided by the native cuticle layer. Or, the plant extract compositions can be formulated to inhibit or provide protection against fungal growth, for which the native cuticle layer provides little or no protection. In some implementations, the cutin derived monomers and/or oligomers are glycerated to form monoacylglycerides prior to the composition being disposed over the plant matter to form the coating. This can, for example, increase the reactivity of the monomers and/or oligomers and allow them to cross-link after being disposed over the plant matter.

In some embodiments, saturated products of the depolymerization reactions such as, for instance, free fatty acid compounds 200 and 202 in FIG. 2, can be separated or at least partially separated from the unsaturated products (or byproducts) of the depolymerization reactions described herein (e.g., unsaturated fatty acid compounds in FIGS. 3A-3I). In some embodiments, the ability to separate or at least partially separate the different types of reaction products can be used to purify, for instance, the saturated products (i.e., compounds wherein hydroxy groups have not been eliminated). In other words, extracting the crude products of a hydrothermal depolymerization reaction set forth herein can be used to purify or enrich the percentage of a given product depending on the solvent used.

As set forth in the Examples below (e.g., Examples 2, 3 and 7), in the case of thermal depolymerization of cutin in water to generate free fatty acids, the crude isolate from a depolymerization reaction was first extracted using a soxhlet apparatus and heptane. After overnight extraction and cooling of the resulting heptane, it was found that a portion of extracted product precipitated from the heptane phase. The precipitate was found to contain saturated products, (e.g., compounds 200 and 202), unsaturated products (e.g., compounds 302 and 304), or a mixture of both saturated and unsaturated products. However, it was found that the heptane supernatant contained depolymerization products that were enriched (e.g., more than 90%, more than 95%, more than 96%, more than 97%, more than 98%, or more than 99%) in unsaturated fatty acids (for example, of the type shown in FIG. 3).

Following the soxhlet extraction with heptane, the crude isolate was again extracted using a soxhlet apparatus and ethyl acetate. It was found that the resulting ethyl acetate phase contained products that were enriched (e.g., more than 90%, more than 95%, more than 96%, more than 97%, more than 98%, or more than 99%) in saturated fatty acids, for instance compounds such as 200 and 202.

Figure 12A:
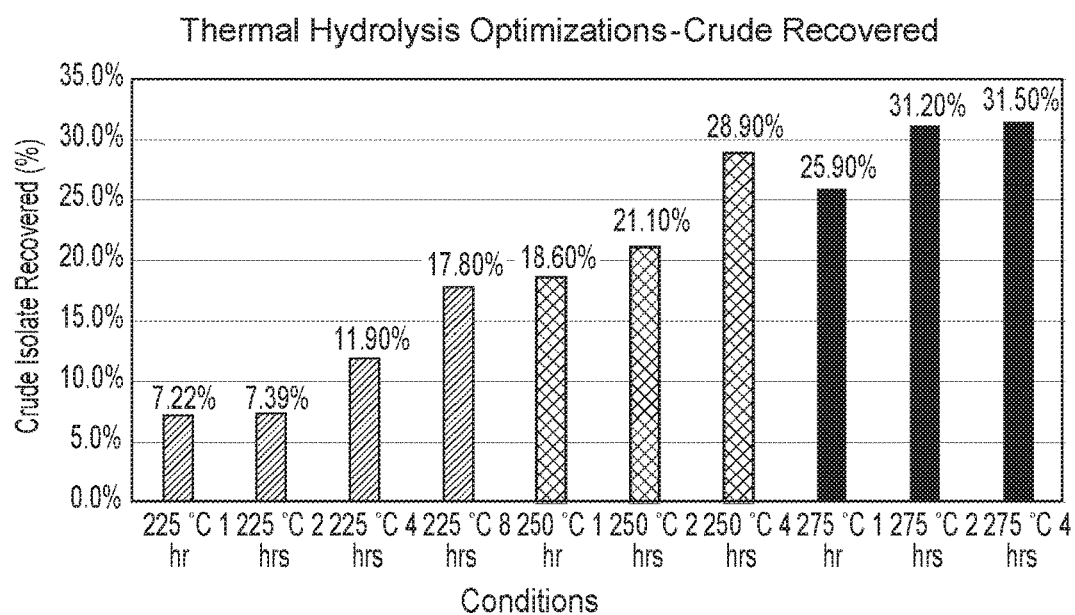
FIG. 12A illustrates a plot of the amount of crude cutin monomers and/or oligomers recovered by thermal depolymerization of cutin in water for various temperatures and reaction durations.

FIG. 12A shows a plot of the crude isolate recovered after thermal depolymerization in water at various temperatures and reaction times using 15 g tomato pomace as a starting material. The recoveries are given as a percentage of the original 15 g input. As shown in FIG. 12A, generally more crude isolate (i.e., cutin-derived monomers and oligomers) is recovered after longer reaction times (e.g., about 4 hours) and at relatively higher temperatures (e.g., about 250° C. or greater).

Figure 12B:
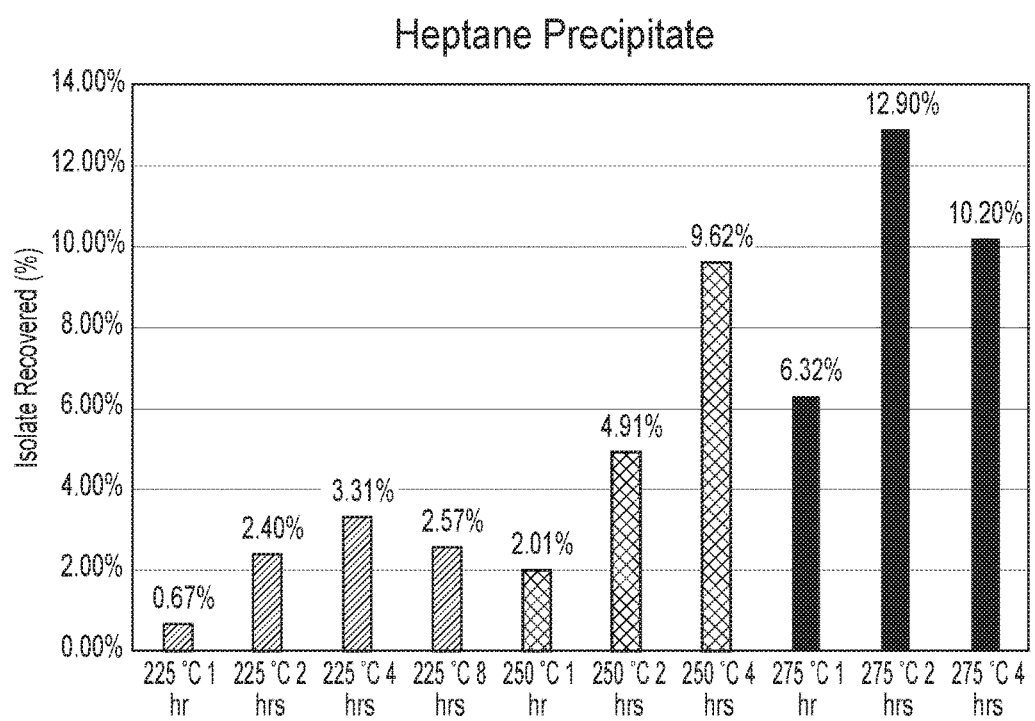
FIG. 12B illustrates a plot of the amount of product (saturated product and/or unsaturated byproduct) isolated from the crude cutin monomers and/or oligomers in the heptane precipitate after soxhlet extraction for various temperatures and residence times.
Figure 12C:
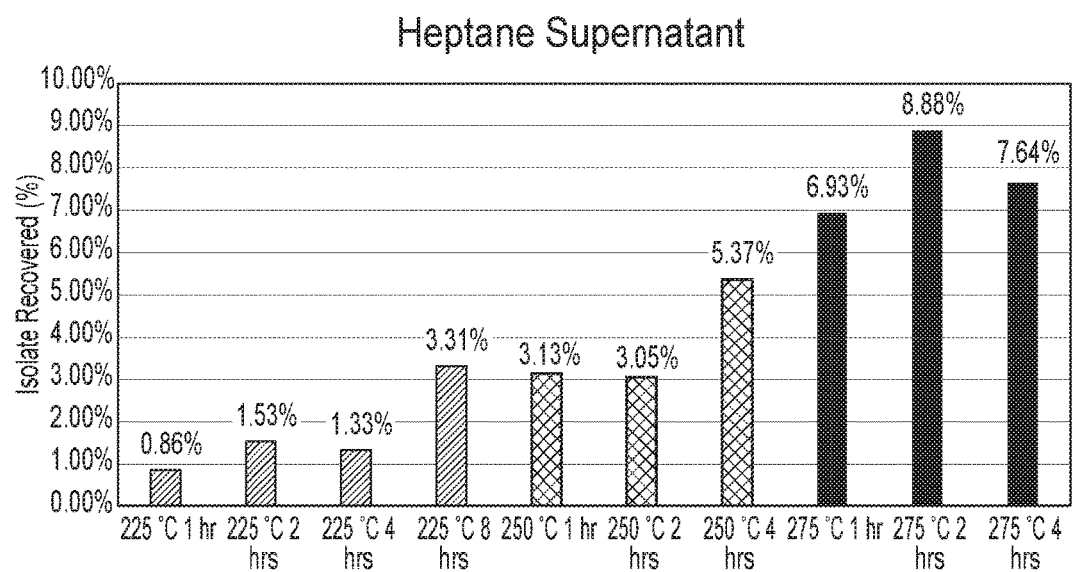
FIG. 12C is a plot of the amount of unsaturated byproduct isolated from the crude cutin monomers and/or oligomers in the heptane supernatant after soxhlet extraction for various temperatures and residence times.

The crude isolate from FIG. 12A was extracted using a soxhlet extractor using both heptane and ethyl acetate. FIG. 12B shows the amount of isolate recovered after a first soxhlet extraction using heptane relative to the initial 15 g of tomato pomace. In particular, FIG. 12B shows the amount of isolate that precipitated from the heptane after soxhlet extraction. In contrast, FIG. 12C shows the amount of isolate that remained dissolved in the heptane supernatant after soxhlet extraction (relative to the 15 g of tomato pomace used as starting material). Without wishing to be bound by theory, the supernatant of a hexane extraction was found to contain primarily (e.g., over 90% or substantially all) unsaturated free fatty acid byproducts (e.g., compounds such as 3A-3I from FIG. 3) of the hydrothermal reactions described herein.

Figure 12D:
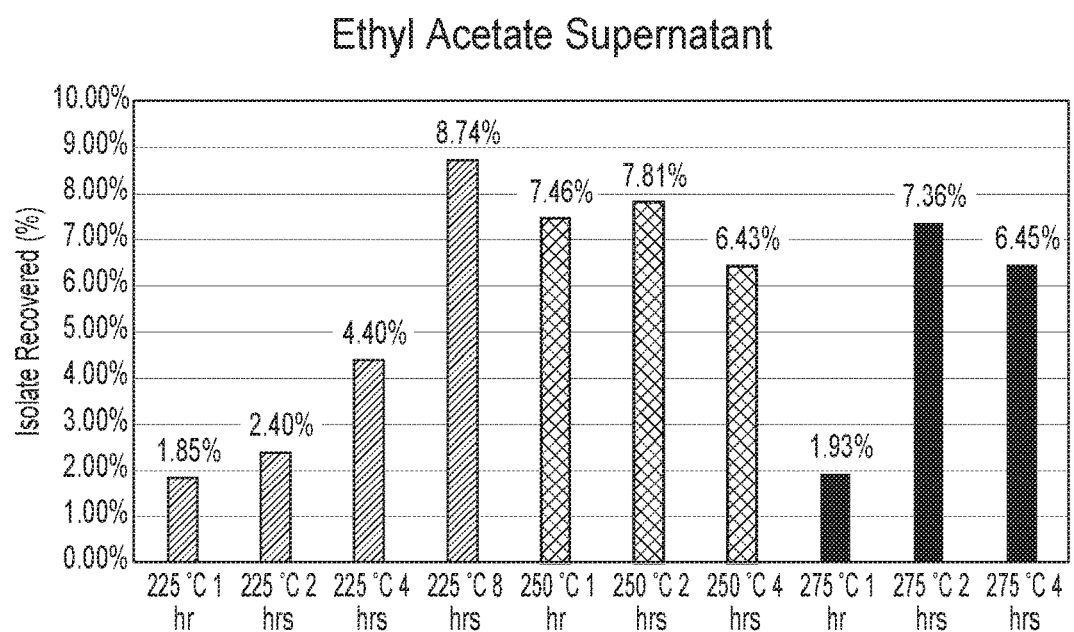
FIG. 12D illustrates a plot of the amount of saturated product isolated from the crude cutin monomers and/or oligomers in the ethyl acetate supernatant after soxhlet extraction for various temperatures and residence times.

FIG. 12D shows the amount of isolate recovered from the heptane-extracted crude isolate after a soxhlet extraction using ethyl acetate as a solvent. The amounts are given relative to the 15 g tomato pomace that was used as a starting material. Without wishing to be bound by theory, the material that was extracted using ethyl acetate was found to contain primarily (e.g., over 90% or substantially all) saturated free fatty acid products (e.g., compounds such as 200 and 202 from FIG. 2) of the hydrothermal reactions described herein.

FIG. 13 gives a table summarizing the products isolated from the heptane precipitate, heptane supernatant, and ethyl acetate supernatant after two soxhlet extractions of crude isolate recovered from hydrothermal depolymerization using heptane and ethyl acetate, respectively. The columns on the left give the hydrothermal reaction conditions that were used to depolymerize the cutin to give crude cutin isolate.

Figure 17:
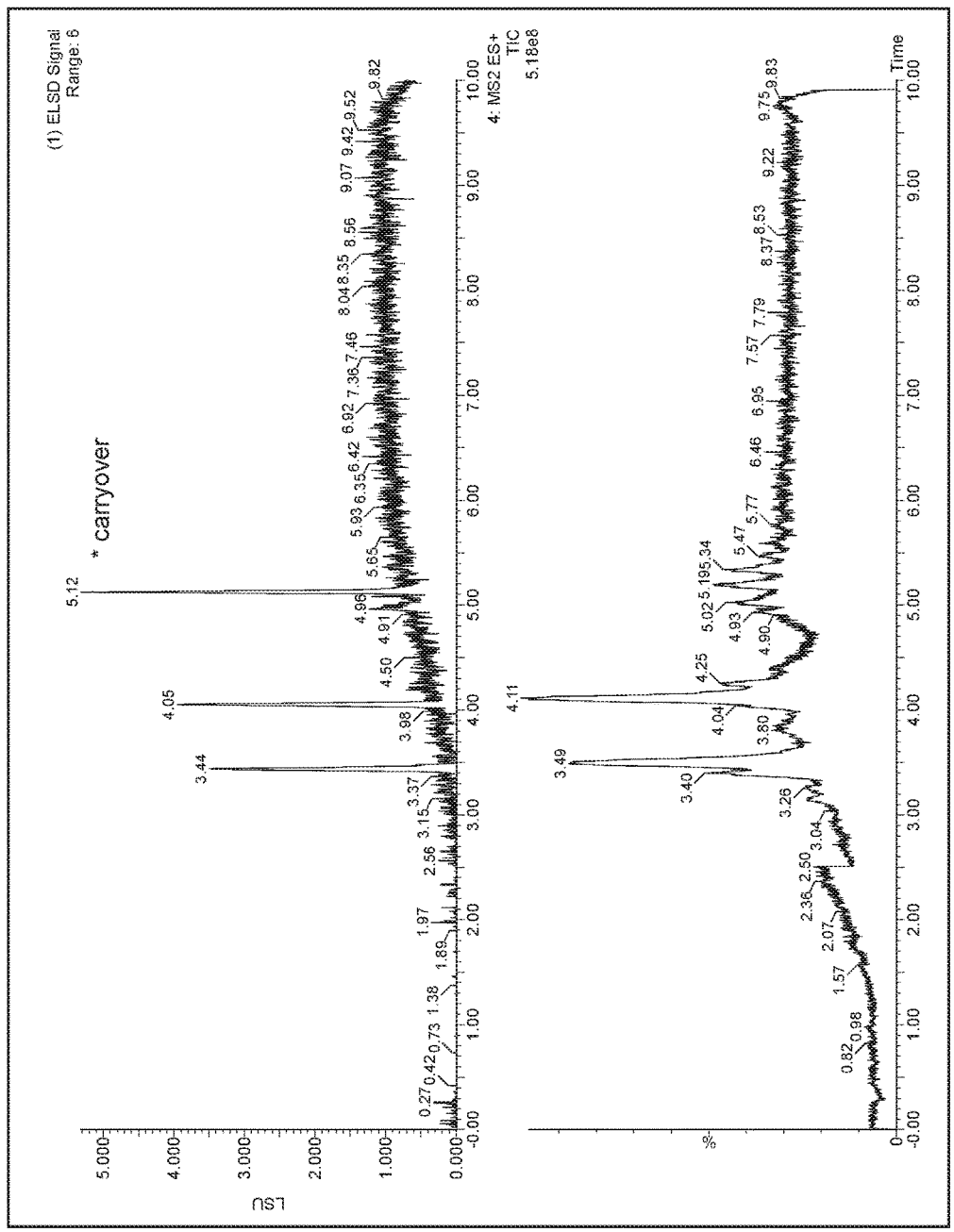
FIG. 17 shows UPLC traces of crude product recovered after hydrothermal depolymerization at 548 K for one hour.
Figure 18:
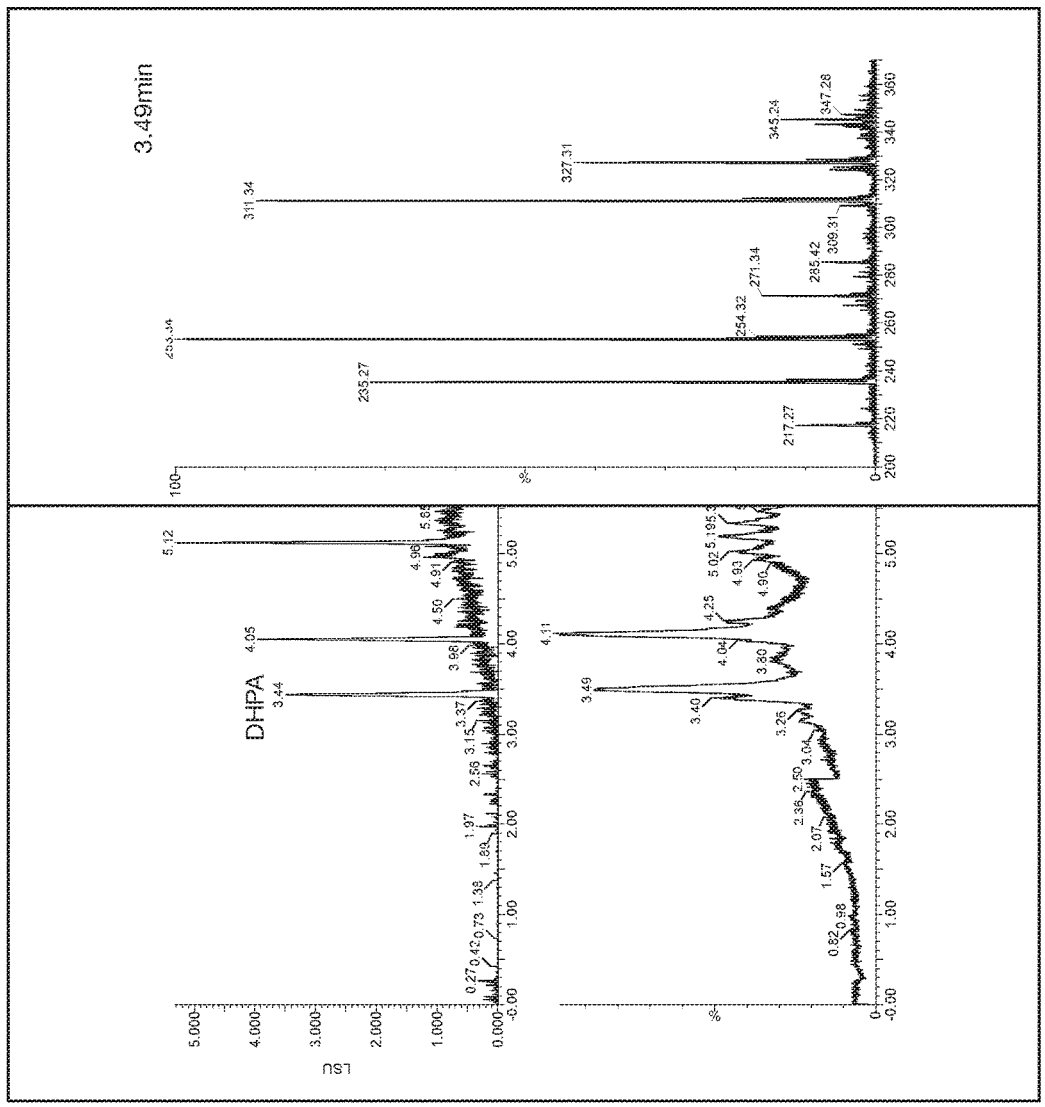
FIG. 18 shows UPLC traces and mass spectrometry analysis of 10,16-dihydroxyhexadecanoic acid recovered after hydrothermal depolymerization at 548 K for one hour before extraction.
Figure 19:
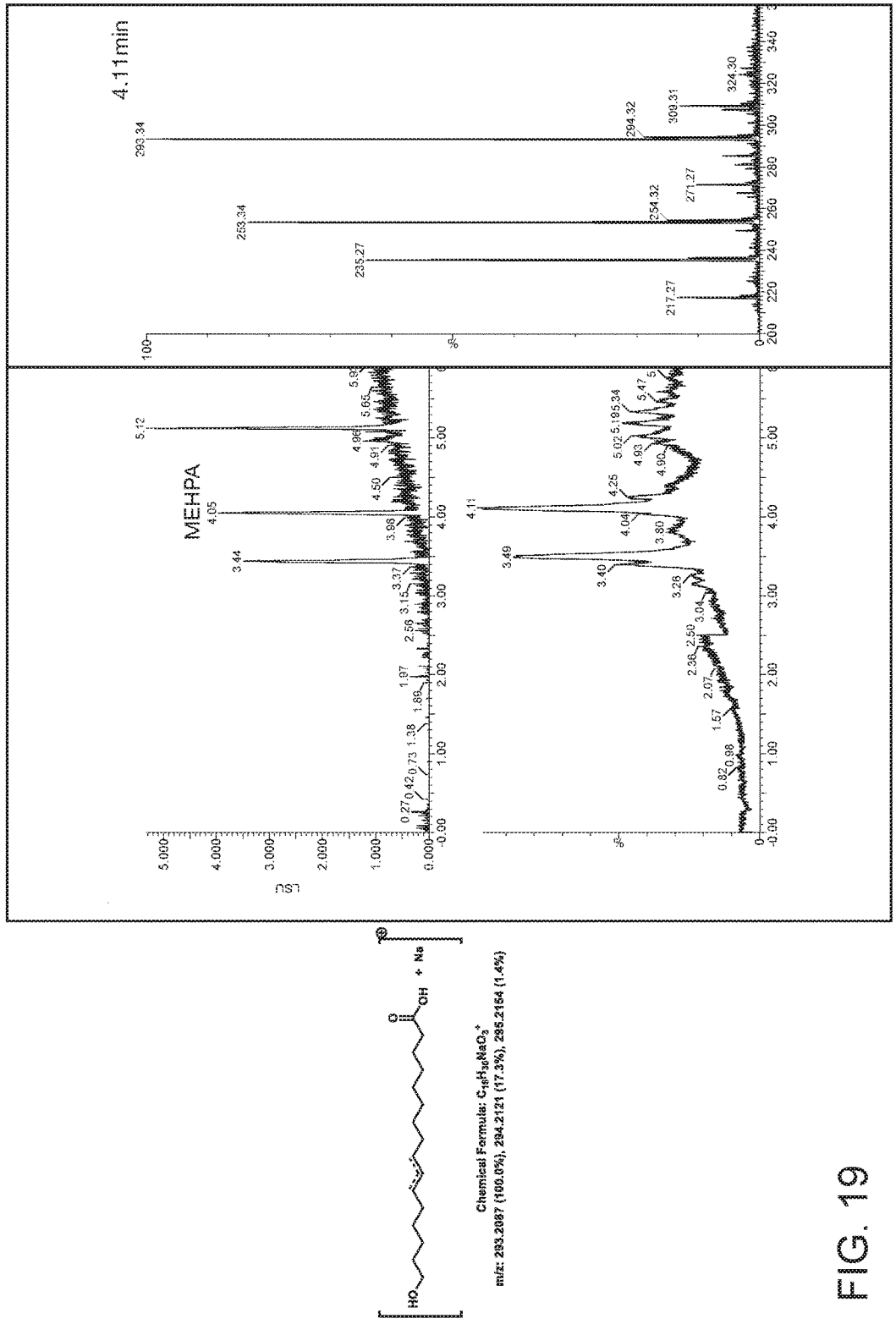
FIG. 19 shows UPLC traces and mass spectrometry analysis of unsaturated fatty acid recovered after hydrothermal depolymerization at 548 K for one hour before extraction.
Figure 20:
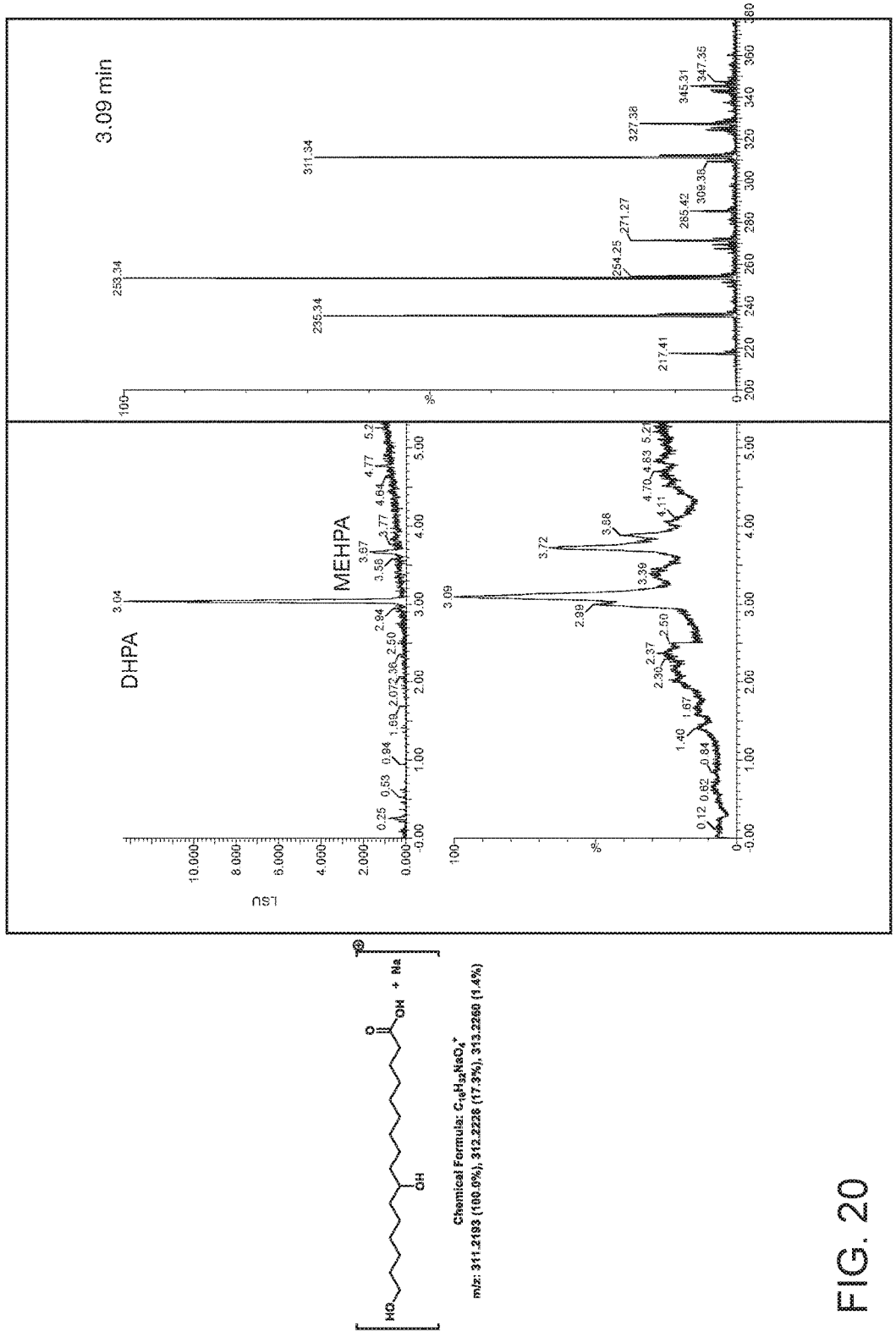
FIG. 20 shows UPLC traces and mass spectrometry analysis of 10,16-dihydroxyhexadecanoic acid recovered from the heptane precipitate after hydrothermal depolymerization at 548 K for one hour and soxhlet extraction with heptane.
Figure 21:
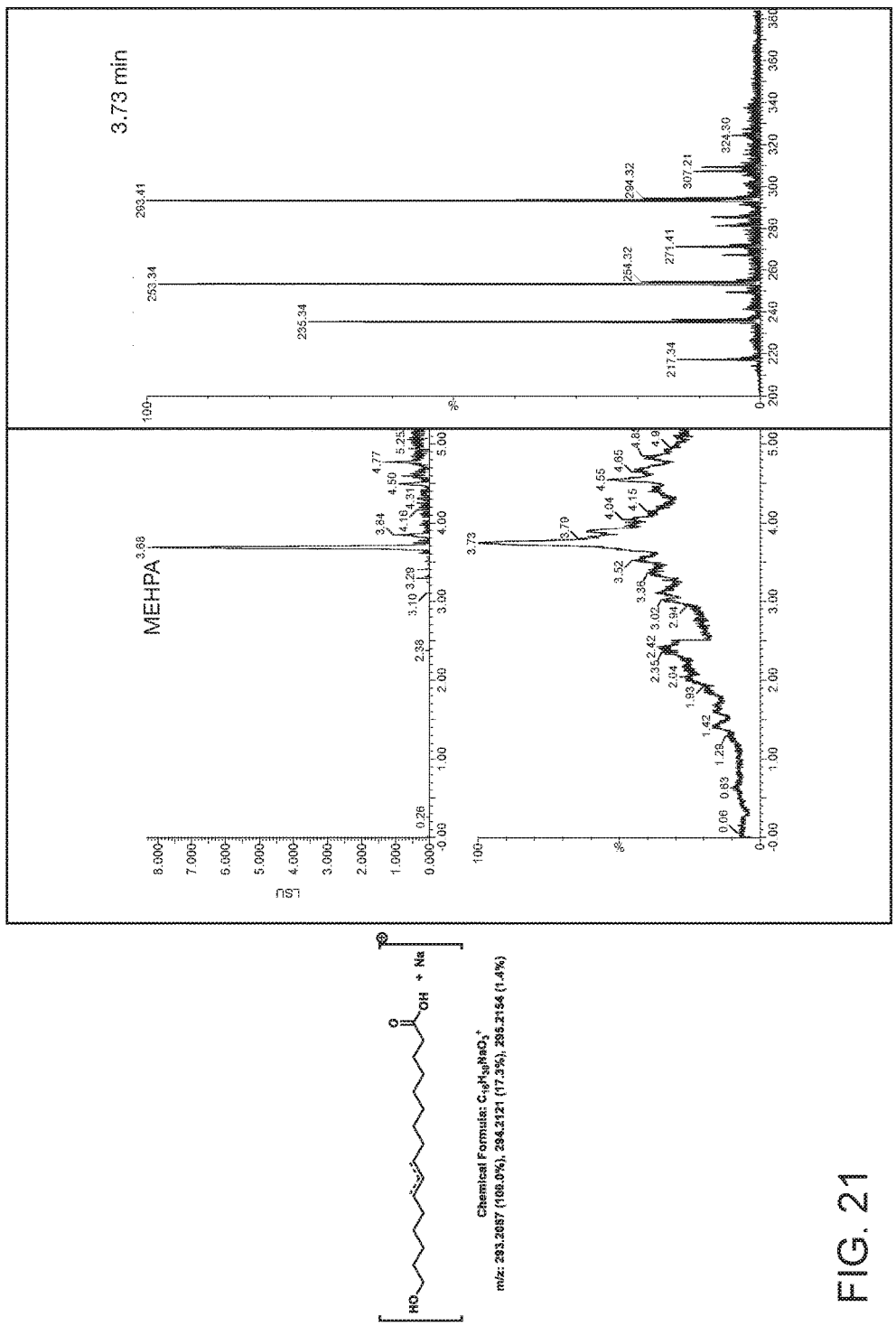
FIG. 21 shows UPLC traces and mass spectrometry analysis of unsaturated fatty acid recovered from heptane supernatant after hydrothermal depolymerization at 548 K for one hour and soxhlet extraction with heptane.
Figure 22:
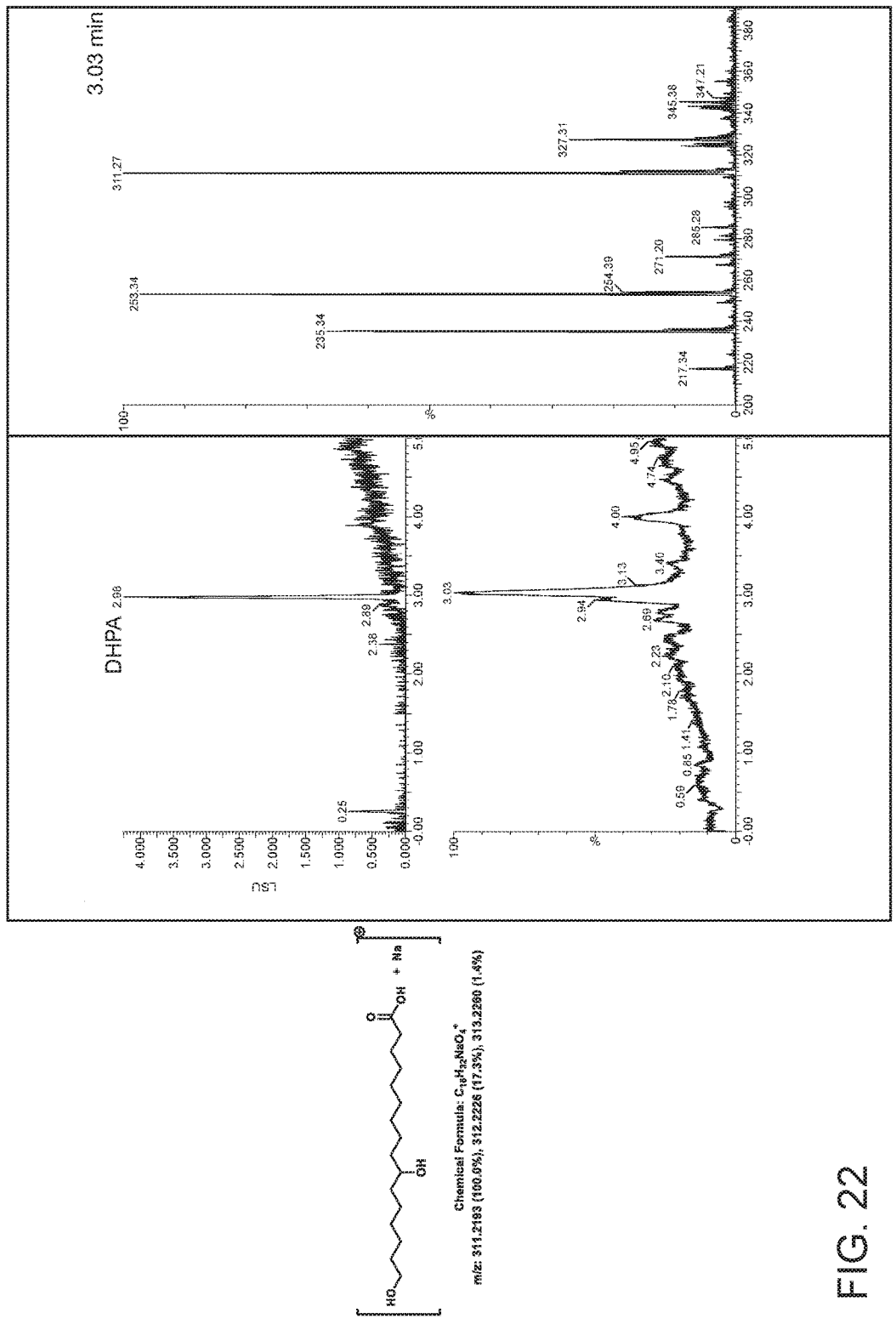
FIG. 22 shows UPLC traces and mass spectrometry analysis of 10,16-dihydroxyhexadecanoic acid recovered from the ethyl acetate supernatant after hydrothermal depolymerization at 548 K for one hour and soxhlet extraction with ethyl acetate.

FIG. 17 shows UPLC traces of crude product recovered after hydrothermal depolymerization at 548 K for one hour. FIG. 18 shows UPLC traces and mass spectrometry analysis of 10,16-dihydroxyhexadecanoic acid recovered after hydrothermal depolymerization at 548 K for one hour before extraction. FIG. 19 shows UPLC traces and mass spectrometry analysis of unsaturated fatty acid recovered after hydrothermal depolymerization at 548 K for one hour before extraction. FIG. 20 shows UPLC traces and mass spectrometry analysis of 10,16-dihydroxyhexadecanoic acid recovered from the heptane precipitate after hydrothermal depolymerization at 548 K for one hour and soxhlet extraction with heptane. FIG. 21 shows UPLC traces and mass spectrometry analysis of unsaturated fatty acid recovered from heptane supernatant after hydrothermal depolymerization at 548 K for one hour and soxhlet extraction with heptane. FIG. 22 shows UPLC traces and mass spectrometry analysis of 10,16-dihydroxyhexadecanoic acid recovered from the ethyl acetate supernatant after hydrothermal depolymerization at 548 K for one hour and soxhlet extraction with ethyl acetate.

In addition to the products of hydrothermal depolymerization, the products of ethanolysis (i.e., ethyl esters) can similarly be separated or at least partially separated using selective or at least partially selective extractions (e.g., soxhlet extractions) and different solvents (e.g., solvents of different polarity).

For example, as set forth in the Examples below (e.g., Examples 4, 5, and 8), the crude product isolated from ethanolysis can be soxhlet extracted using heptane. In some embodiments, the ethyl esters isolated from ethanolysis can be less polar than the free fatty acids isolated by hydrolysis. As set forth in the Examples below, after overnight soxhlet extraction of crude ethanolysis material using heptane and subsequent cooling, it was found that a precipitate formed from the heptane extract. The heptane precipitate was found to contain products that were enriched (e.g., more than 90%, more than 95%, more than 96%, more than 97%, more than 98%, or more than 99%) in saturated ethyl esters (e.g., hydroxylated products such as compound 600 or compound 602). In contrast, it was found that the supernatant contained dissolved products that were enriched (e.g., more than 90%, more than 95%, more than 96%, more than 97%, more than 98%, or more than 99%) in unsaturated ethyl esters, for example compounds such as those set forth in FIG. 7A-FIG. 7I. In some embodiments, no ethyl acetate extraction was performed on the heptane-extracted isolate of ethanolysis. For example, in some embodiments the selective precipitation of saturated (e.g., hydroxylated) products from the heptane extraction upon cooling was sufficient to enable purification of the hydroxylated products (e.g., by filtration).

Figure 14A:
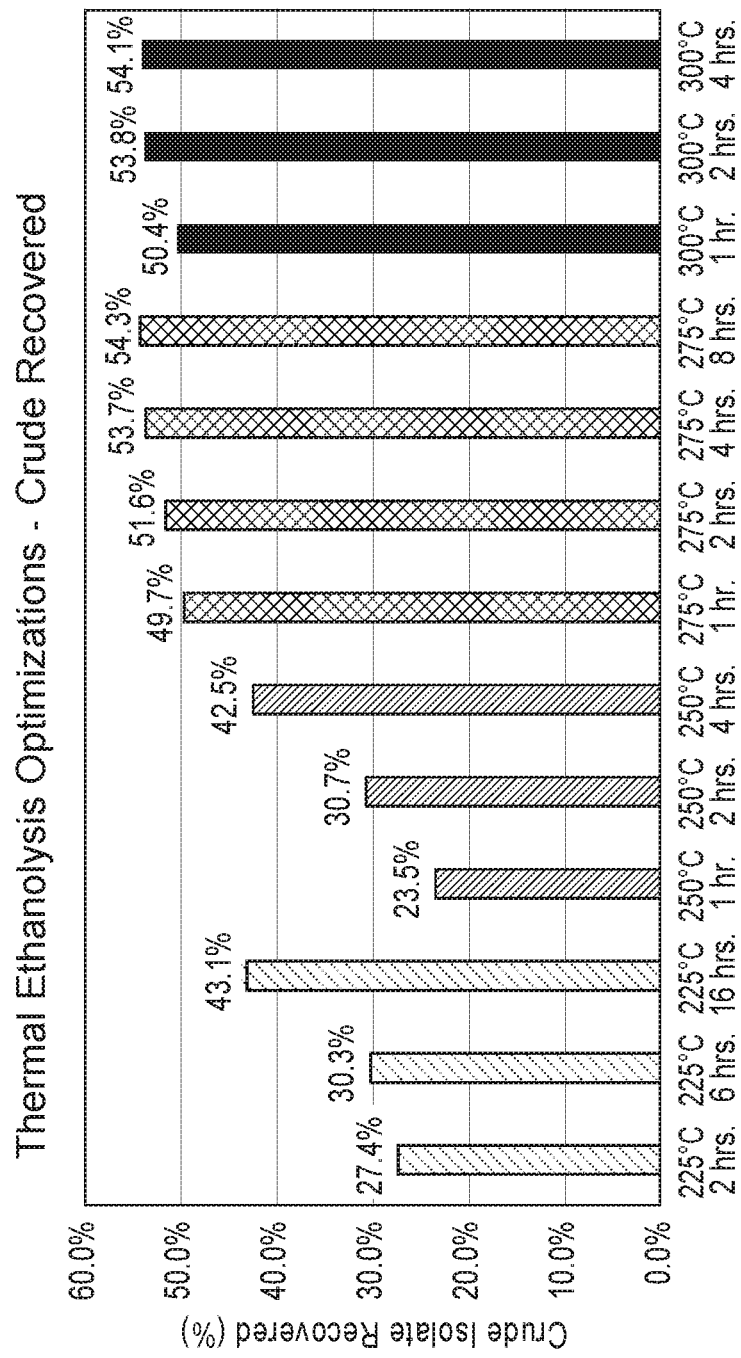
FIG. 14A is a plot of percentage of crude product recovered by thermal depolymerization of cutin in ethanol for various temperatures and residence times.

FIG. 14A shows a plot of the crude isolate recovered after thermal depolymerization in ethanol at various temperatures and reaction times using 15 g tomato pomace as a starting material. The recoveries are given as a percentage of the original 15 g input. As shown in FIG. 14A, generally more crude isolate (i.e., cutin-derived monomers and oligomers) is recovered after longer reaction times (e.g., about 4 hours) and at relatively higher temperatures (e.g., about 523 K or greater).

Figure 14B:
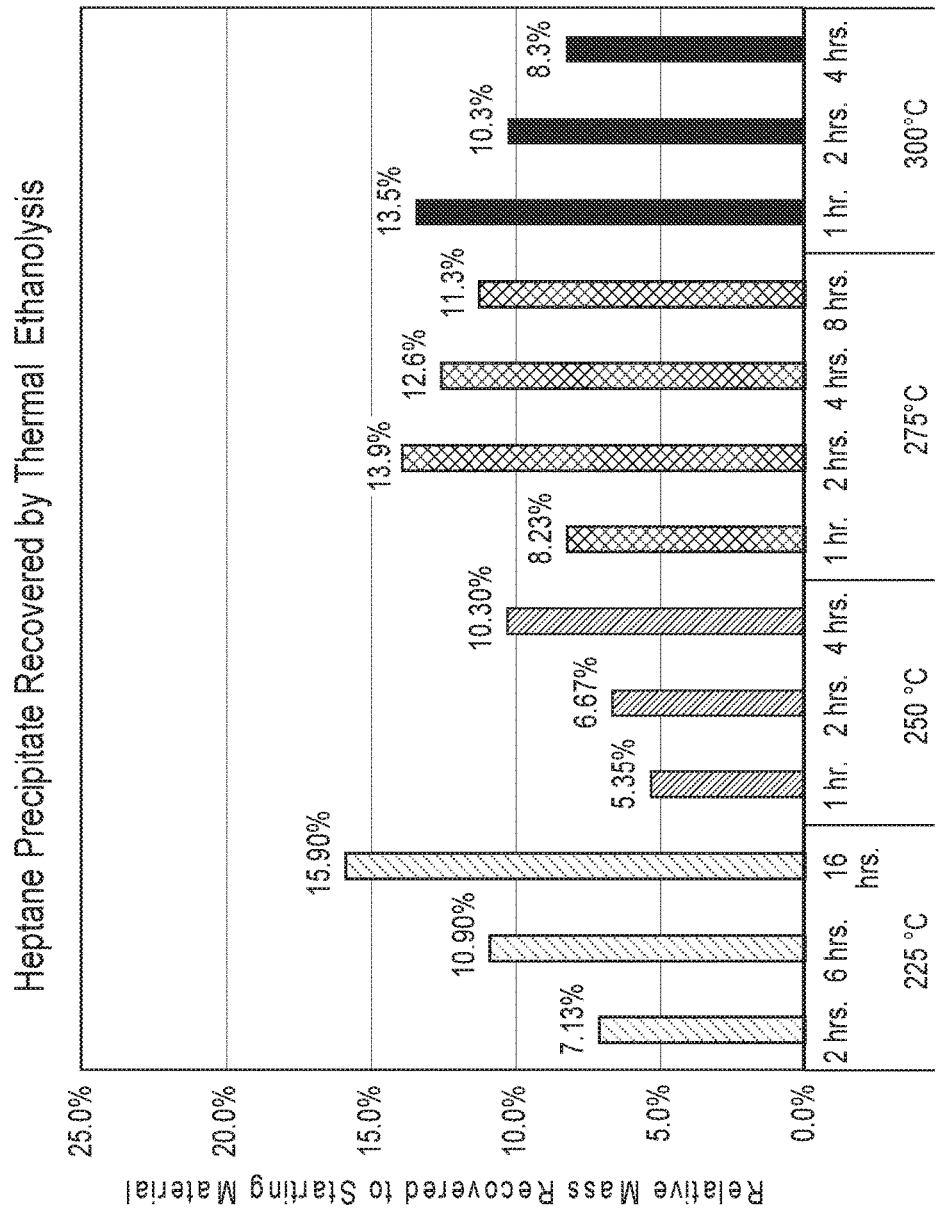
FIG. 14B is a plot of percentage of product recovered from a heptane precipitate during thermal depolymerization of cutin in ethanol for various temperatures and residence times.
Figure 14C:
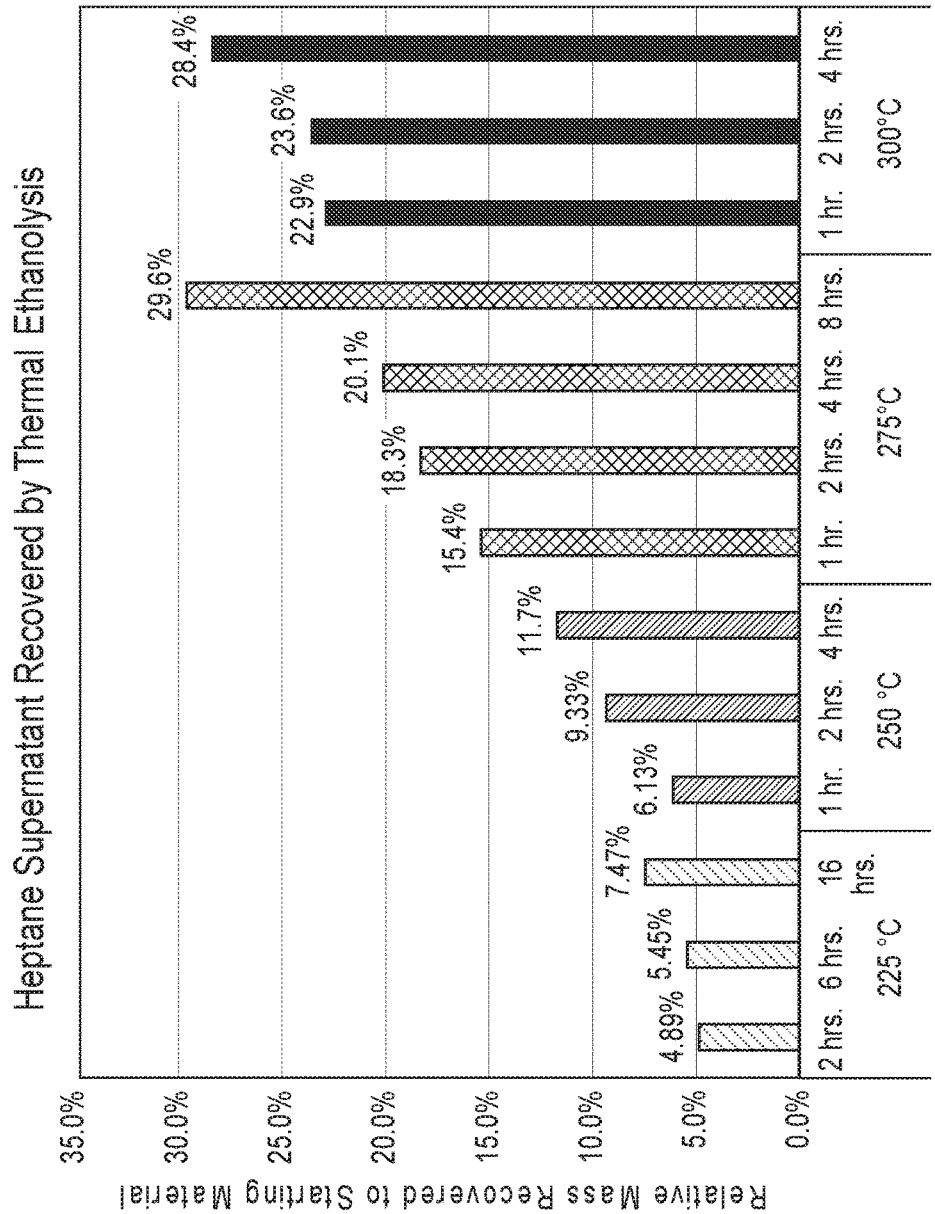
FIG. 14C is a plot of percentage of product recovered from a heptane supernatant during thermal depolymerization of cutin in ethanol for various temperatures and residence times.

The crude isolate from FIG. 14A was extracted using a soxhlet extractor using heptane. FIG. 14B shows the amount of isolate recovered after a soxhlet extraction using heptane relative to the initial 15 g of tomato pomace. In particular, FIG. 14B shows the amount of isolate that precipitated from the heptane after soxhlet extraction and cooling. In contrast, FIG. 14C shows the amount of isolate that remained dissolved in the heptane supernatant after soxhlet extraction (relative to the 15 g of tomato pomace used as starting material). Without wishing to be bound by theory, the supernatant of the hexane extraction was found to contain primarily (e.g., over 90% or substantially all) unsaturated ethyl ester byproducts (e.g., compounds such as 7A-7I from FIG. 7) of the hydrothermal reactions described herein (i.e., the unsaturated ethyl esters remained dissolved in the heptane supernatant).

Without wishing to be bound by theory, the material that precipitated from the heptane after extraction (which could be isolated by filtration) was found to contain primarily (e.g., over 90% or substantially all) saturated ethyl ester products (e.g., compounds such as 600 and 602 from FIG. 6) of the hydrothermal reactions described herein.

FIG. 15 gives a table summarizing the products isolated from the heptane precipitate and heptane supernatant after soxhlet extraction of crude isolate recovered from ethanolysis depolymerization. The columns on the left give the ethanolysis reaction conditions that were used to depolymerize the cutin to give crude cutin isolate.

Figure 23:
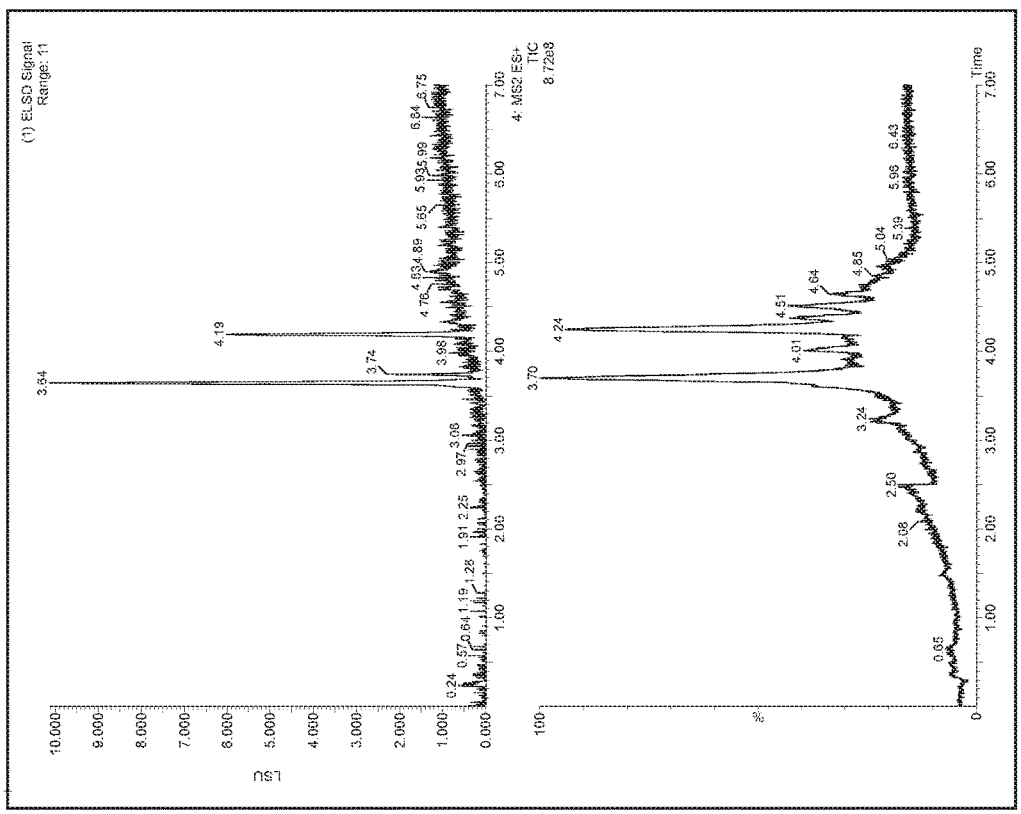
FIG. 23 shows UPLC traces of crude product recovered after ethanolysis depolymerization at 548 K for four hours.
Figure 24:
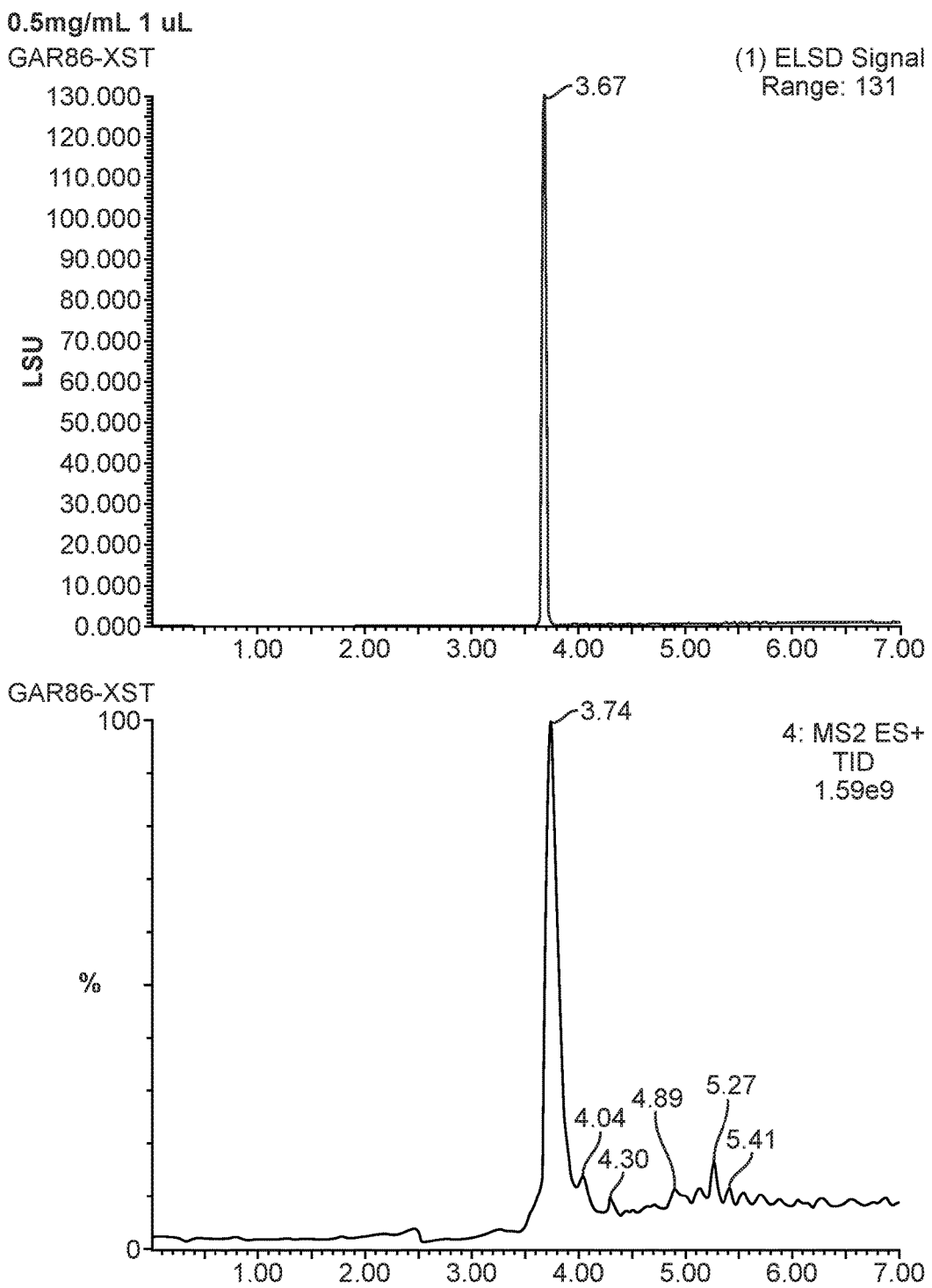
FIG. 24 shows UPLC traces and mass spectrometry analysis of ethyl 10,16-dihydroxyhexadecanoate recovered from the heptane supernatant after ethanolysis depolymerization at 548 K for four hours and soxhlet extraction with heptane.
Figure 24:
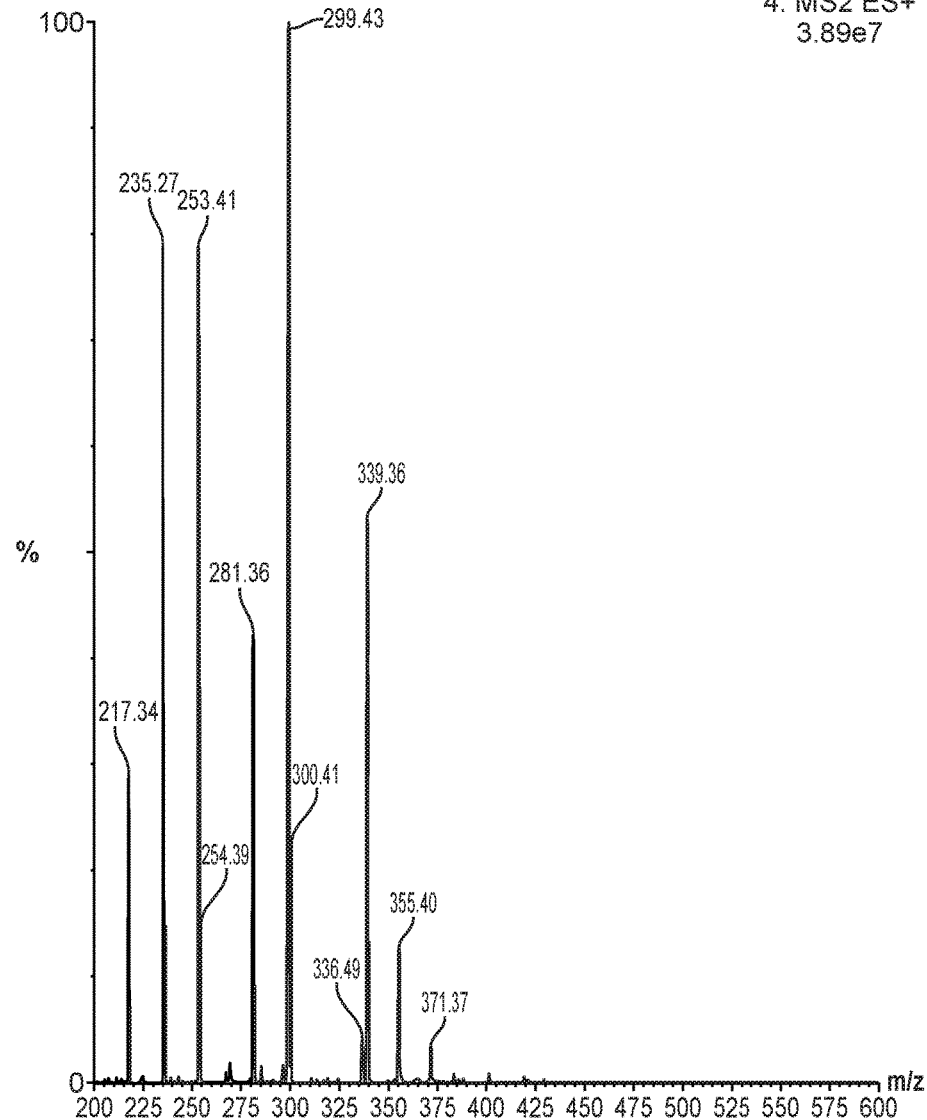
Figure 24:
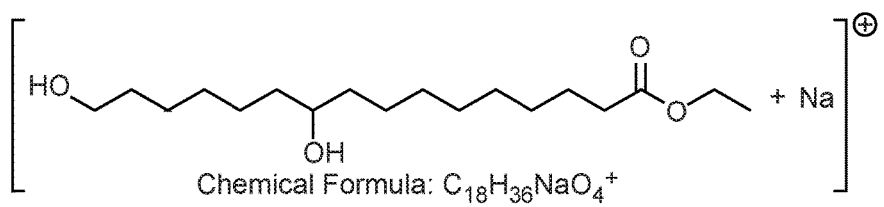
Figure 25:
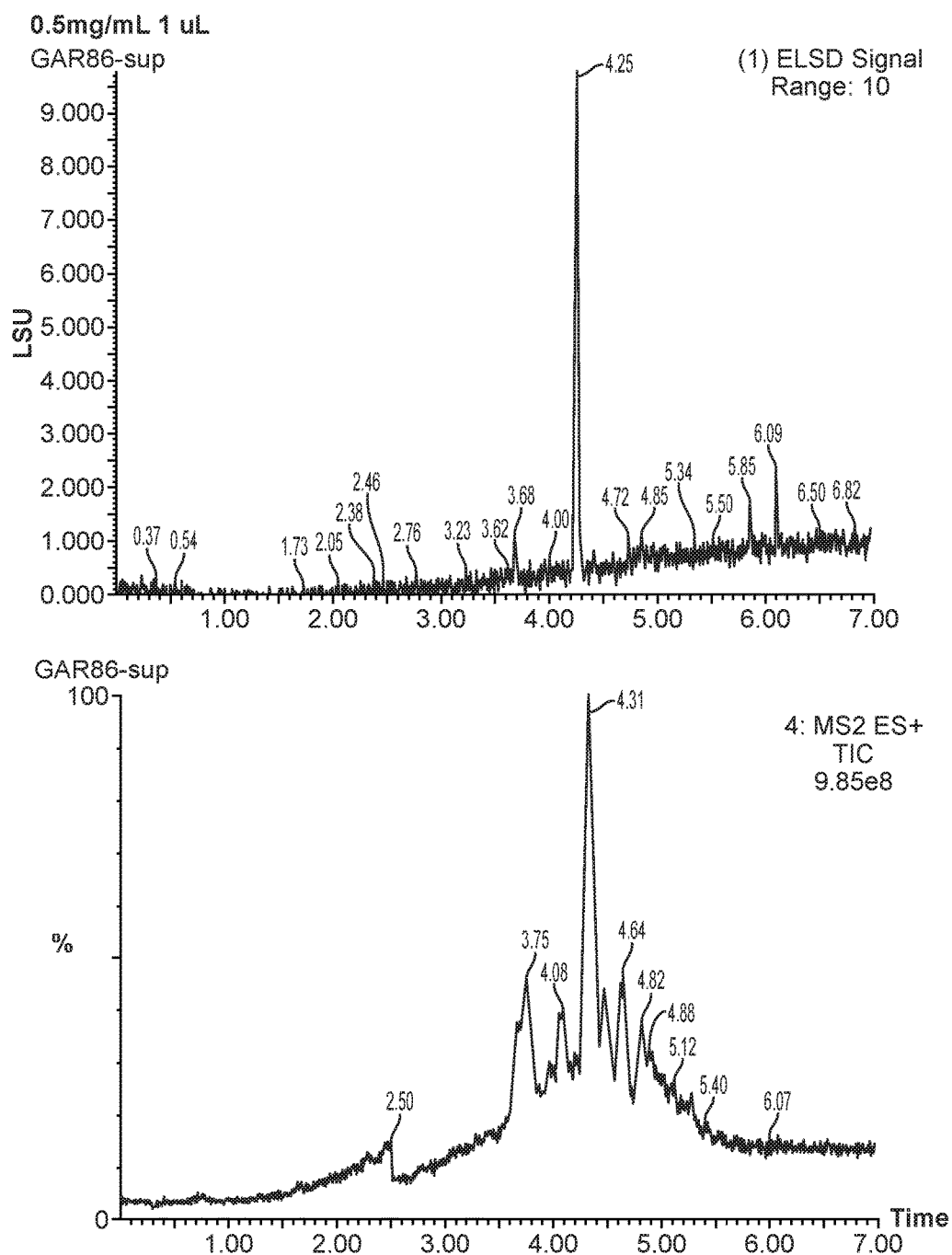
FIG. 25 shows UPLC traces and mass spectrometry analysis of unsaturated fatty acid ethyl ester recovered from the heptane supernatant after ethanolysis depolymerization at 548 K for four hours and soxhlet extraction with heptane.
Figure 25:
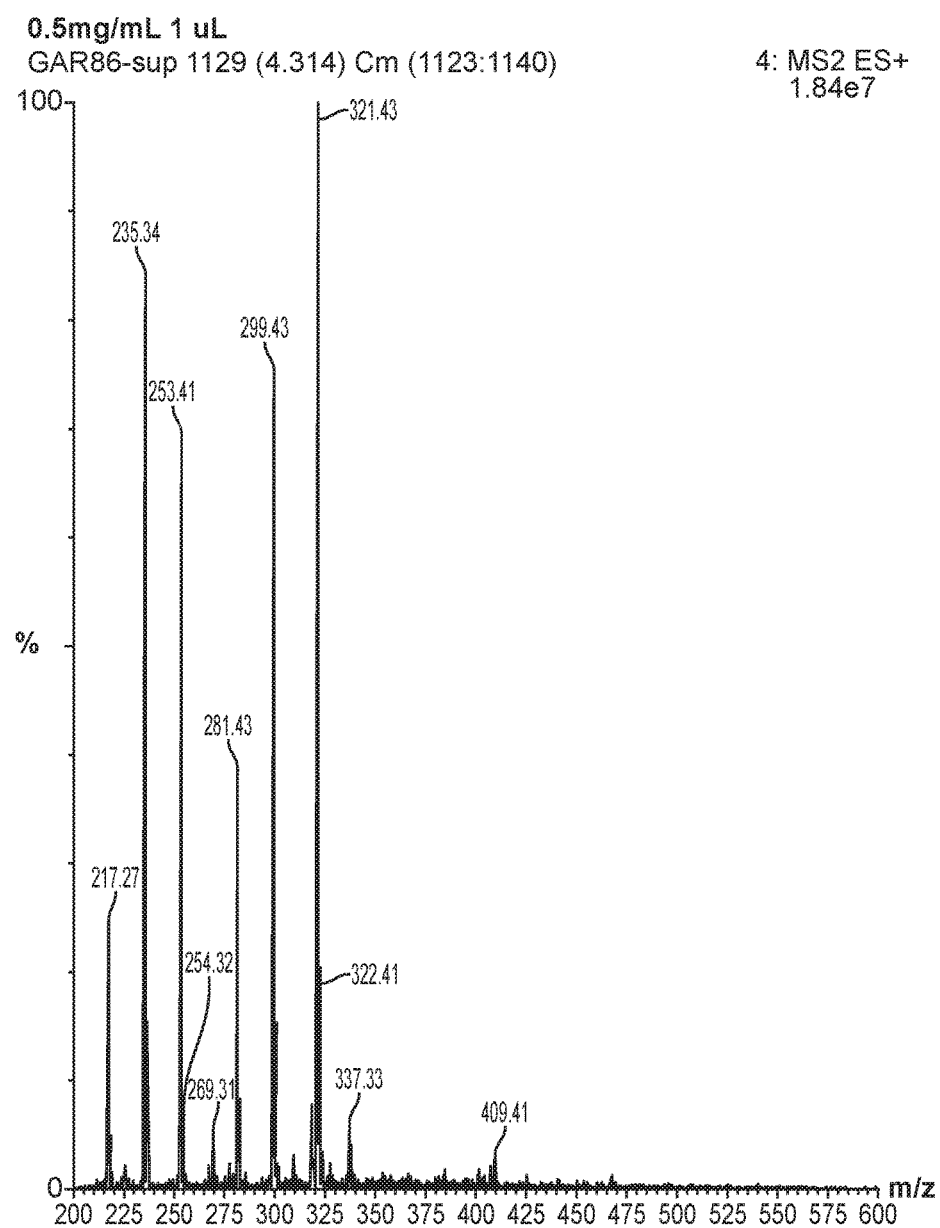
Figure 25:
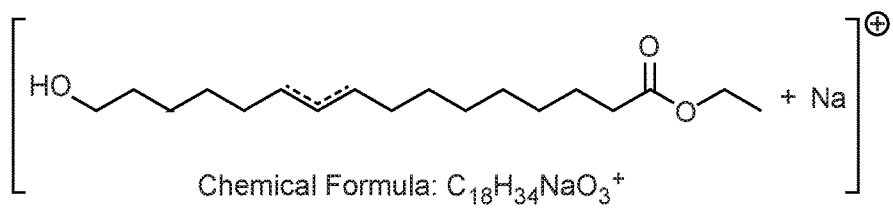

FIG. 23 shows UPLC traces of crude product recovered after ethanolysis depolymerization at 548 K for four hours. FIG. 24 shows UPLC traces and mass spectrometry analysis of ethyl 10,16-dihydroxyhexadecanoate recovered from the heptane supernatant after ethanolysis depolymerization at 548 K for four hours and soxhlet extraction with heptane. FIG. 25 shows UPLC traces and mass spectrometry analysis of unsaturated fatty acid ethyl ester recovered from the heptane supernatant after ethanolysis depolymerization at 548 K for four hours and soxhlet extraction with heptane.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims. All solvents and other chemical reagents were obtained from commercial sources (e.g., Sigma-Aldrich (St. Louis, Mo.)) and were used without further purification unless noted otherwise.

The following steps have been carried out to perform one or more of the thermal depolymerization processes described herein, in which cuticular material was thermally processed into free fatty acids. For each of Examples 2-5, the complete processes were carried out multiple times in order to collect statistically significant data. Where applicable in these examples, the data presented is given as an average value of the various iterations, along with the statistical deviation from the average.

Example 1: Method for Preparing Tomato Pomace Prior to Depolymerization

Tomato pomace obtained from a commercial tomato processing facility was milled in a cutting mill, and sifted to give different particle size distributions (e.g. >500 µm, 250-500 µm, 125-250 µm, etc.). The fraction corresponding to 250-500 m sequentially underwent soxhlet extractions with chloroform ($CHCl_3$) overnight and methanol overnight to remove the surface waxes and other soluble components, followed by drying under vacuum (<1 torr). The washed pomace was then lyophilized overnight (<0.02 torr) to remove water, and then stored in a desiccator before use.

Example 2: Depolymerization of Cutin in Water at 498K 15 g of the 250-500 m extracted tomato pomace (from Example 1) was added to a Parr 4563B reactor with an internal volume of 600 mL. To this was added 375 mL of water, after which the system was sealed and the reactor mounted to the system, followed by heating to a target temperature of about 498K. The heating time from ambient room temperature (typically about 298K) to the target temperature was about 45 minutes. The mixture was then held at 498K for about 8 hours, after which it was rapidly cooled by an internal cooling loop to a temperature between 25° C. and 40° C.

After cooling, the reactor was depressurized, unmounted, and unsealed. The reactor's internal components and walls were rinsed with ethyl acetate until all material was loosened from the walls, and the resulting solid/liquid mixture was filtered through a medium porosity filter frit. The reactor body was washed with a second portion of ethyl acetate, and this was filtered through the filter cake. The solid cake, giving the 'char' or residue material, was washed with an additional portion of ethyl acetate. Typical total volume of the ethyl acetate washings was about 350 mL. The water/ethyl acetate mixture collected from the filtration was separated in a 1 L separatory funnel. The phases were separated, and the organic layer was collected and dried by addition of magnesium sulfate before filtering through a porous frit. The ethyl acetate was then removed from the organic phase by rotary evaporation and further dried under high vacuum (P<0.1 torr). The total mass of the resulting crude extract composition, which included both saturated and unsaturated fatty acids, was on average 2.86 g [Avg.]±0.23 g (n=3).

Collection of the crude extract composition was followed by purification. First, the crude extract was dissolved in methanol, after which three times the mass of Celite 545 was added. The methanol was removed by rotary evaporation, allowing the material to be deposited onto the Celite. This mixture was transferred to a cellulose extraction thimble, and glass wool was placed on top of the mixture. The thimble was placed in a soxhlet extractor, flushed with nitrogen, and extracted with 500 mL heptane overnight.

Upon cooling, some of the monomer product (e.g., 200 in FIG. 2A) or unsaturated byproduct (e.g., 302, 306, and/or 308 in FIGS. 3A-3D, respectively) precipitated out of solution. The apparatus was disassembled, and the extraction thimble set aside. The heptane in the round bottom, referred to as the heptane supernatant, was then separated, and the heptane removed by rotary evaporation. The precipitate and supernatant fractions were kept separate, with the precipitate weighing 0.594 g [Avg.]±0.18 g (n=3), and the heptane supernatant (containing only unsaturated byproducts, e.g., 302, 304) weighing 0.500 g [Avg.]±0.06 g (n=3). The extraction thimble underwent soxhlet extraction with ethyl acetate following the same procedure as the previously described heptane soxhlet extraction. After cooling, the apparatus was disassembled, and the ethyl acetate in the round bottom was removed by rotary evaporation. Upon drying under high vacuum, a viscous oil was recovered having a mass of 1.20 g [Avg.]±0.21 g (n=3). Characterization showed that the product predominately comprised compounds 200 (FIG. 2A). Without wishing to be bound by theory, it was found that the different soxhlet extractions selectively isolated either the monomer product or the unsaturated byproduct, based on the solvent being used for the extraction. The unsaturated byproduct was selectively isolated in the heptane soxhlet's supernatant, whereas the monomer product was selectively isolated in the ethyl acetate soxhlet's supernatant.

Conversion of biomass and product characterization were performed by gravimetric, ultra-high performance liquid chromatography-electrospray or atmospheric-pressure chemical ionization mass spectrometry, and nuclear magnetic resonance experiments. Exemplary $^1$HNMR data for recovered products across multiple depolymerizations using the above procedure is given below.

10,16-dihydroxypalmtic acid: $^1$H NMR (600 MHz, Methanol-d4) δ 3.53 (td, J=6.8, 2.8 Hz, 2H), 3.49 (dq, J=7.4, 3.7 Hz, 1H), 2.26 (t, J=7.4 Hz, 3H), 1.60 (q, J=7.2 Hz, 4H), 1.52 (q, J=6.9 Hz, 4H), 1.43 (tt, J=9.1, 4.7 Hz, 6H), 1.39-1.22 (m, 23H).

(E/Z)-16-hydroxyhexadec-9-enoic acid: $^1$H NMR (600 MHz, Methanol-d4) δ 5.44-5.29 (m, 2H), 3.53 (td, J=6.7, 2.3 Hz, 2H), 2.26 (t, J=7.5 Hz, 3H), 2.03 (dd, J=8.3, 4.8 Hz, 1H), 1.97 (p, J=5.8 Hz, 3H), 1.59 (p, J=7.2 Hz, 3H), 1.56-1.48 (m, 3H), 1.43 (dt, J=11.2, 4.2 Hz, 1H), 1.40-1.27 (m, 20H).

Example 3: Depolymerization of Cutin in Water at 523K 15 g of the 250-500 m extracted tomato pomace (from Example 1) was added to a Parr 4563B reactor with an internal volume of 600 mL. To this was added 375 mL of water, after which the system was sealed and the reactor mounted to the system, followed by heating to a target temperature of about 523K. The heating time from ambient room temperature (typically about 298K) to the target temperature was about 45 minutes. The mixture was then held at 523K for about 2 hours, after which it was rapidly cooled by an internal cooling loop to a temperature between 25° C. and 40° C.

After cooling, the reactor was depressurized, unmounted, and unsealed. The reactor's internal components and walls were rinsed with ethyl acetate until all material was loosened from the walls, and the resulting solid/liquid mixture was filtered through a medium porosity filter frit. The reactor body was washed with a second portion of ethyl acetate, and this was filtered through the filter cake. The solid cake, giving the 'char' or residue material, was washed with an additional portion of ethyl acetate. Typical total volume of the ethyl acetate washings was about 350 mL. The water/ethyl acetate mixture collected from the filtration was separated in a 1 L separatory funnel. The phases were separated, and the organic layer was collected and dried by addition of magnesium sulfate before filtering through a porous frit. The ethyl acetate was then removed from the organic phase by rotary evaporation and further dried under high vacuum (P<0.1 torr). The total mass of the resulting crude extract composition, which included both saturated and unsaturated fatty acids, was 3.30 g [Avg.]±0.08 g (n=3).

Collection of the crude extract composition was followed by purification. First, the crude extract was dissolved in methanol, after which three times the mass of Celite 545 was added. The methanol was removed by rotary evaporation, allowing the material to be deposited onto the Celite. This mixture was transferred to a cellulose extraction thimble, and glass wool was placed on top of the mixture. The thimble was placed in a soxhlet extractor, flushed with nitrogen, and extracted with 500 mL heptane overnight.

Upon cooling, some of the monomer product (e.g., 200 in FIG. 2A) or unsaturated byproduct (302, 304, 306, and/or 308 in FIGS. 3A-3D, respectively) precipitated out of solution. The apparatus was disassembled, and the extraction thimble set aside. The heptane in the round bottom, referred to as the heptane supernatant, was then separated, and the heptane removed by rotary evaporation. The precipitate and supernatant fractions were kept separate, with the precipitate weighing 0.800 g and the heptane supernatant (containing the unsaturated byproducts (e.g., 302, 304)) weighing 0.530 g. The extraction thimble underwent soxhlet extraction with ethyl acetate following the same procedure as previously described for the heptane soxhlet extraction. After cooling, the apparatus was disassembled, and the ethyl acetate in the round bottom was removed by rotary evaporation. Upon drying under high vacuum, a viscous oil was recovered having a mass of 1.35 g [Avg.]±0.15 g (n=3). Without wishing to be bound by theory, characterization showed that the product predominately comprised compound 200 (see FIG. 2A). Conversion of biomass and product characterization were performed by gravimetric, ultra-high performance liquid chromatography-electrospray or atmospheric-pressure chemical ionization mass spectrometry, and nuclear magnetic resonance experiments.

Example 4: Depolymerization of Cutin in Ethanol at 498K 15 g of the 250-500 m extracted tomato pomace (from Example 1) was added to a Parr 4563B reactor with an internal volume of 600 mL. To this was added 170 mL of ethanol, after which the system was sealed and the reactor mounted to the system, followed by heating to a target temperature of about 498K. The heating time from ambient room temperature (typically about 298K) to the target temperature was about 45 minutes. The pressure in the sealed Parr 4563B reactor system was about 667 psi (about 45.4 atm). The mixture was then held at 498K for about 16 hours, after which it was rapidly cooled by an internal cooling loop to a temperature between 25° C. and 40° C.

After cooling, the reactor was depressurized, unmounted, and unsealed. The solid/liquid mixture was filtered through a medium porosity filter frit, and the reactor body and filter cake washed with additional ethanol until washing ran clear. Typical total volume of the washings was about 350 mL. The ethanol was removed from the liquid portion by rotary evaporation, after which the material was subjected to high vacuum (P<0.1 torr). The total mass of the resulting crude extract composition, which included both saturated and unsaturated fatty acid ethyl esters, was 6.79 g [Avg.]±0.14 g (n=3).

The unsaturated fatty acid ethyl esters were then separated from the crude extract composition as follows. The resulting mixture, including both the saturated and unsaturated fatty acid ethyl esters, was dissolved in ethyl acetate, and three times the mass of Celite 545 powder was added. The ethyl acetate was removed by rotary evaporation, allowing the material to be deposited onto the Celite. This mixture was transferred to a cellulose extraction thimble, and glass wool was placed on top of the mixture. The thimble was placed in a soxhlet extractor, flushed with nitrogen, and extracted with 500 mL heptane overnight. After cooling to room temperature, the system was disassembled, and the round-bottom flask was left to crystallize at room temperature overnight. The solids were then separated by filtration through a Buchner funnel and filter paper. This solid material, which comprised saturated fatty acid ethyl esters but not unsaturated fatty acid ethyl esters, was 2.28 g [Avg.]±0.25 g (n=3). Conversion of biomass and product characterization were performed by gravimetric, ultra-high liquid chromatography-electrospray or atmospheric-pressure chemical ionization mass spectrometry, and nuclear magnetic resonance experiments. Exemplary $^1$HNMR data for recovered products across multiple depolymerizations using the above procedure is given below.

Ethyl 10,16-dihydroxyhexdecanoate: $^1$H NMR (600 MHz, Chloroform-d) δ 4.11 (q, J=7.1 Hz, 2H), 3.63 (t, J=6.8 Hz, 2H), 3.57 (s, 1H), 2.27 (t, J=7.6 Hz, 2H), 1.66-1.51 (m, 6H), 1.49-1.25 (m, 21H), 1.24 (t, J=7.1 Hz, 3H).

Ethyl (E/Z)-16-hydroxyhexadec-9-enoate: $^1$H NMR (600 MHz, Chloroform-d) δ 5.45-5.27 (m, 2H), 4.11 (q, J=7.1 Hz, 2H), 3.63 (t, J=6.7 Hz, 2H), 2.27 (t, J=7.6 Hz, 2H), 2.05-1.89 (m, 4H), 1.64-1.51 (m, 5H), 1.38-1.22 (m, 22H).

Example 5: Depolymerization of Cutin in Ethanol at 548K 15 g of the 250-500 m extracted tomato pomace (from Example 1) was added to a Parr 4563B reactor with an internal volume of 600 mL. To this was added 170 mL of ethanol, after which the system was sealed and the reactor mounted to the system, followed by heating to a target temperature of about 548K. The heating time from ambient room temperature (typically about 298K) to the target temperature was about 60 minutes. The pressure in the sealed Parr 4563B reactor system was about 1348 psi (about 91.7 atm). The mixture was then held at 548K for about 2 hours, after which it was rapidly cooled by an internal cooling loop to a temperature between 25° C. and 40° C.

After cooling, the reactor was depressurized, unmounted, and unsealed. The solid/liquid mixture was filtered through a medium porosity filter frit, and the reactor body and filter cake washed with additional ethanol until washing ran clear. Typical total volume of the washings was about 350 mL. The ethanol was removed from the liquid portion by rotary evaporation, after which the material was subjected to high vacuum (P<0.1 torr). The total mass of the resulting crude extract composition, which included both saturated and unsaturated fatty acid ethyl esters, was 7.95 g [Avg.]±0.25 g (n=3).

The unsaturated fatty acid ethyl esters were then separated from the crude extract composition as follows. The resulting mixture, including both the saturated and unsaturated fatty acid ethyl esters, was dissolved in ethyl acetate, and three times the mass of Celite 545 powder was added. The ethyl acetate was removed by rotary evaporation, allowing the material to be deposited onto the Celite. This mixture was transferred to a cellulose extraction thimble, and glass wool was placed on top of the mixture. The thimble was placed in a soxhlet extractor, flushed with nitrogen, and extracted with 500 mL heptane overnight. After cooling to room temperature, the system was disassembled, and the round-bottom flask was left to crystallize at room temperature overnight. The solids were then separated by filtration through a Buchner funnel and filter paper. Without wishing to be bound by theory, this solid material, which comprised saturated fatty acid ethyl ester but not unsaturated fatty acid ethyl esters, was 2.03 g [Avg.]±0.25 g (n=3).

The heptane supernatant was evaporated to dryness using a rotary evaporator, before being placed under high vacuum (P<0.1 torr). This oily material, which was comprised of unsaturated fatty acids, was 2.89 g [Avg.]±0.09 g (n=3). Conversion of biomass and product characterization were performed by gravimetric, ultra-high performance liquid chromatography-electrospray or atmospheric-pressure chemical ionization mass spectrometry, and nuclear magnetic resonance experiments.

Example 6: Depolymerization of Cutin in Glycerol at 573K 15 g of the 250-500 m extracted tomato pomace (from Example 1) was added to a Parr 4563B reactor with an internal volume of 600 mL. To this was added 190 mL of glycerol and 10 mL H$_2$O, after which the system was sealed and the reactor mounted to the system, followed by heating to a target temperature of about 573K. The heating time from ambient room temperature (typically about 298K) to the target temperature was about 60 minutes. The pressure in the sealed Parr 4563B reactor system was about 290 psi (about 19.7 atm). The mixture was then held at 573K for about 4 hours, after which it was rapidly cooled by an internal cooling loop to a temperature between 25° C. and 40° C.

After cooling, the reactor was depressurized, unmounted, and unsealed. The components of the extract composition that remained in the liquid and solid portions of the mixture were extracted by diluting the mixture with 300 mL of water. The desired product was then extracted with 400 mL ethyl acetate. Residual glycerol was removed from the ethyl acetate mixture by washing it with 1 L of water. The ethyl acetate was removed by rotary evaporation. The final mass was recorded once the liquid was evaporated to complete dryness. Without wishing to be bound by theory, the total mass of the resulting crude composition, which were found to be enriched in unsaturated fatty acid glycerol esters (e.g., compounds 902, 904, 906, and 908 in FIGS. 9A-9D, respectively), was 8.01 g. Conversion of biomass and product characterization was performed by gravimetric, ultra-high performance liquid chromatography-electrospray or atmospheric-pressure chemical ionization mass spectrometry, and nuclear magnetic resonance experiments. Exemplary $^1$HNMR data for recovered products across multiple depolymerizations using the above procedure is given below.

$^1$H NMR (600 MHz, Methanol-d4) δ 5.41-5.31 (m, 2H), 4.14 (dd, J=11.4, 4.3 Hz, 1H), 4.05 (dd, J=11.3, 6.3 Hz, 1H), 3.81 (p, J=5.6 Hz, 1H), 3.65 (dtd, J=16.8, 11.6, 5.2 Hz, 2H), 2.34 (t, J=7.4 Hz, 4H), 2.03 (t, 2H), 1.97 (d, J=7.2 Hz, 3H), 1.60 (s, 3H), 1.54-1.49 (m, 3H), 1.30 (m, 28H).

Example 7: Optimization of Extraction Conditions and Depolymerization of Cutin in Water Various additional optimizations of the steps described in Examples 2-3 above were also performed. For example, in addition to the temperatures and residence times described in Examples 2-3 (thermal depolymerization in water), cutin depolymerization in water through the methods described herein was also carried out at 225° C. (498K) for 1 hour, 2 hours, 4 hours, and 8 hours; at 250° C. (523K) for 1 hour, 2 hours, and 4 hours; and at 275° C. (548K) for 1 hour, 2 hours, and 4 hours. The percentage of saturated and unsaturated fatty acids recovered, relative to the 15 g of tomato pomace originally inserted into the reactor, was determined at each temperature and time point and plotted in FIG. 12A. As seen in FIG. 12A, the percent of crude extract recovered increases at higher temperatures and longer residence times.

Following the soxhlet purification, the quantity of direct monomer product (e.g., 200 in FIG. 2A) and unsaturated byproduct (e.g., 302, 304, 306, and 308 in FIGS. 3A-3D, respectively) was determined. As previously described and also shown below with reference to FIG. 13, either the direct monomer products, a mixture of the direct monomer and unsaturated byproducts, or the unsaturated byproducts are collected in the heptane precipitate, whereby the relative amounts of each in the heptane precipitate depend on the temperature and residence time. Without wishing to be bound by theory, it is believed that this variation in precipitate composition may be due to the high temperature of the solvent wash leading to melting of the materials and subsequent flow out of the soxhlet extractor (a non-selective process), rather than dissolution in the solvent and removal as a solution (a more selective process). This may be overcome by modified equipment design (e.g., a cooled receiver), or use of pressure to modulate the boiling point of the solvent and consequently the temperature of the condensed solvent. FIG. 12B plots the amounts (as a percentage relative to the initial 15 g of tomato pomace) recovered from the heptane precipitate. As previously described, the unsaturated byproduct is selectively isolated in the heptane supernatant, of which the amount recovered (as a percentage relative to the initial 15 g of tomato pomace) is shown in FIG. 12C. Recall that the ethyl acetate supernatant selectively isolates the direct monomer product, of which the amount recovered (as a percentage relative to the initial 15 g of tomato pomace) is shown in FIG. 12D. In general, longer residence times and higher temperatures resulted in increased conversion to the byproducts.

As described above, the soxhlet extractions can selectively isolate either the direct monomer product or unsaturated byproduct. Furthermore, adjusting the times and temperatures can at least partially determine which fatty acid product (direct monomer product or unsaturated byproduct) is produced. FIG. 13 is a table indicating which products were recovered from the heptane precipitate, from the heptane supernatant, and from the ethyl acetate supernatant at the various depolymerization temperatures and residence times tested. In FIG. 13, 'Sat' refers to direct monomer products (including, for example, 200 in FIG. 2A), and 'Unsat' refers to unsaturated byproducts (including, for example, any of compounds 302, 304, 306, and 308 in FIGS. 3A-3D, respectively). Referring first to the heptane precipitate products, at lower depolymerization temperatures (e.g., at 498K), only the direct monomer products were recovered for all residence times up to 8 hours (and no substantial product of any kind was recovered at a 1 hour residence time). At intermediate depolymerization temperatures (523 K), only direct monomer products were recovered for the 1 hour residence time, whereas a mixture of the direct monomer products and unsaturated byproducts were recovered for longer residence times (2 hours and 4 hours). At higher depolymerization temperatures (548K), a mixture of the direct monomer products and unsaturated byproducts were recovered for shorter residence times (1 hour and 2 hours), whereas only unsaturated byproducts were recovered for the longer (4 hour) residence time.

FIGS. 17-22 shows UPLC characterization data for depolymerization of tomato pomace at 548 K for 1 h in water. Referring now to the heptane supernatant products, in which the unsaturated byproducts are selectively isolated, the unsaturated byproducts were not observed at low depolymerization temperature (498 K) at residence times of 4 hours or less, but were observed at 498 K for the case of an 8 hour residence time. At intermediate and higher depolymerization temperatures (523 K and 548 K, respectively), the unsaturated byproducts were observed for all residence times (1 hour, 2 hours, and 4 hours).

Referring now to the ethyl acetate supernatant products, in which the direct monomer products are selectively isolated, the direct monomer products were not observed at low depolymerization temperature (498 K) at residence times of 2 hours or less, but were observed at 498 K for the cases of 4 hour and 8 hour residence times. At intermediate depolymerization temperatures (523 K), the direct monomer products were observed for all residence times (1 hour, 2 hours, and 4 hours). At higher depolymerization temperatures (548 K), the direct monomer products were observed for 1 hour and 2 hour residence times, but were not observed in the case of a 4 hour residence time.

Example 8: Optimization of Extraction Conditions and Depolymerization of Cutin in Ethanol In addition to the optimization of the steps in Examples 2-3 (thermal depolymerization in water) described in Example 7 above, additional optimization of the steps described in Examples 4-5 above (thermal depolymerization in ethanol) were also performed. For example, in addition to the temperatures and residence times described in Examples 4-5, cutin depolymerization in ethanol through the methods described herein was also carried out at 225° C. (498K) for 2 hours and 6 hours; at 250° C. (523K) for 1 hour, 2 hours, and 4 hours; at 275° C. (548K) for 1 hour and 4 hours; and at 300° C. for 1 hour, 2 hours, and 4 hours. The percentage of saturated and unsaturated fatty acids recovered, relative to the 15 g of tomato pomace originally inserted into the reactor, was determined at each temperature and time point and plotted in FIG. 14A. As seen in FIG. 14A, the percent of crude extract recovered increases at higher temperatures and longer residence times.

Following the heptane soxhlet purification procedure, the respective quantity of direct monomer ethyl ester product (e.g., 600 in FIG. 6A) and unsaturated ethyl ester byproduct (e.g., 702, 704, 706, and 708 in FIGS. 7A-7D, respectively) was determined. As previously described, the direct monomer products are collected in the heptane precipitate, thereby separating the direct monomer products from the unsaturated byproducts. FIG. 14B plots the amounts (as a percentage relative to the initial 15 g of tomato pomace) recovered from the heptane precipitate. As previously described, the unsaturated byproduct is selectively isolated in the heptane supernatant, of which the amount recovered (as a percentage relative to the initial 15 g of tomato pomace) is shown in FIG. 14C. In general, longer residence times and higher temperatures resulted in increased conversion to desired products.

As described above, the soxhlet extractions can selectively isolate either the direct monomer ester product or unsaturated ester byproduct. Furthermore, adjusting the times and temperatures can at least partially determine which fatty acid ester product (direct monomer ester product or unsaturated ester byproduct) is produced. FIG. 15 is a table indicating which products were recovered from the heptane precipitate and from the heptane supernatant at the various depolymerization temperatures and residence times tested. In FIG. 15, 'Sat' refers to direct monomer ester products (e.g., 600 in FIG. 6A) and 'Unsat' refers to unsaturated ester byproducts (including, for example, any of compounds 702, 704, 706, and 708 in FIGS. 7A-7D, respectively). Referring first to the heptane precipitate products, at lower depolymerization temperatures (e.g., at 498 K), only the direct monomer products were recovered for residence times of at least 6 hours (and no substantial product of any kind was recovered at 2 hours residence time). At higher depolymerization temperatures (523K, and 573K), direct monomer product was recovered for residence times of 1 hour, 2 hours, and 4 hours. At a depolymerization temperature of 548K, direct monomer product was recovered for residence times of 1 hour, 2 hours, 4 hours, and 8 hours.

Referring now to the heptane supernatant products, in which the unsaturated byproducts are selectively isolated, the unsaturated byproducts were not observed at low depolymerization temperature (498K) at residence times of 2 hours, 4 hours, or 16 hours. At intermediate depolymerization temperatures (523K), the unsaturated byproducts were not observed at residence times of 2 hours or less, but were observed at 523K for the case of a 4 hour residence time. At higher depolymerization temperatures (548K and 573K) the unsaturated byproducts were observed for all residence times (1 hour, 2 hours, and 4 hours).

FIGS. 23-25 give UPLC characterization data after depolymerization of tomato pomace at 548K for 4 hr in ethanol.

Example 9: Protective Coatings Formed Over Avocados

Protective coatings were formed over avocados by extracting compounds by method described herein (thermal depolymerization of cutin) and depositing the compounds over the outer surface of the (unpeeled) avocados. The mass loss rates of the avocados were then measured and compared to those of uncoated avocados. All coatings were formed by dipping the avocados in a solution comprising the associated compounds dissolved in substantially pure ethanol at a concentration of 10 mg/mL, placing the avocados on drying racks, and allowing the avocados to dry under ambient room conditions at a temperature in the range of about 23° C.-27° C. and humidity in the range of about 40%-55%. The avocados were held at these same temperature and humidity conditions for the entire duration of the time they were tested.

Figure 16:
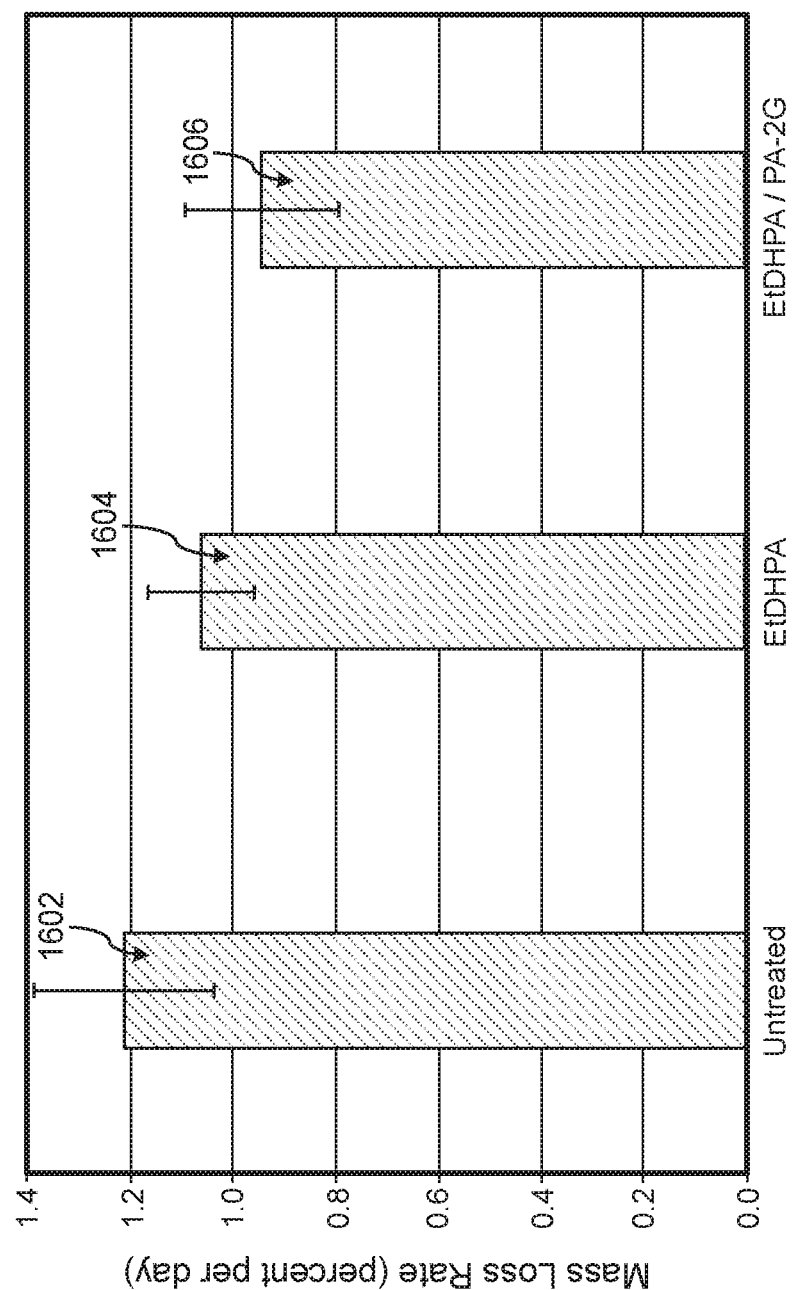
FIG. 16 is a plot of mass loss rates of avocados coated with compositions formed by methods described herein.

Mass loss rates are shown in FIG. 16 for untreated (e.g., uncoated) avocados in bar 1602, for avocados coated with ethyl 10,16-dihydroxyhexadecanoate (referred to as "EtDHPA") in bar 1604, and for avocados coated with a mixture of EtDHPA and 1,3-dihydroxypropan-2-yl hexadecanoate (referred to as "PA-2G") in bar 1606, where for bar 1606 the EtDHPA and PA-2G were mixed at a mass ratio of 30:70. For bars 1604 and 1606, the EtDHPA was formed by thermal depolymerization of cutin in ethanol as described herein, while the PA-2G was formed by a multi-step process utilizing palmitic acid as the starting material, where the process is described in detail in U.S. patent application Ser. No. 15/530,403 titled "PRECURSOR COMPOUNDS FOR MOLECULAR COATINGS." Each bar in the graph represents a group of 30 avocados. All avocados were obtained from the same source, were picked at about the same time, and were at a similar stage of ripening.

As seen in FIG. 16, the mass of the uncoated avocados (bar 1602) decreased at an average rate of about 1.21% per day, the mass of the avocados coated with EtDHPA (bar 1604) decreased at an average rate of about 1.06% per day, and the mass of the avocados coated with the EtDHPA/PA-2G mixture (bar 1606) decreased at an average rate of about 0.94% per day. As such, the average mass loss rate of avocados coated with EtDHPA (bar 1604) was reduced by more than 12% as compared to the uncoated avocados (bar 1602), and the average mass loss rate of avocados coated with the EtDHPA/PA-2G mixture (bar 1606) was reduced by more than 22% as compared to the uncoated avocados (bar 1602).

Various implementations of the compositions and methods have been described above. However, it should be understood that they have been presented by way of example only, and not limitation. Where methods and steps described above indicate certain events occurring in certain order, those of ordinary skill in the art having the benefit of this disclosure would recognize that the ordering of certain steps may be modified and such modification are in accordance with the variations of the disclosure. The implementations have been particularly shown and described, but it will be understood that various changes in form and details may be made. Accordingly, other implementations are within the scope of the following claims.

The invention claimed is:

1. A method of preparing cutin-derived monomers, oligomers, or combinations thereof from cutin-containing plant matter, comprising:
   obtaining cutin from the cutin-containing plant matter;
   adding the cutin to a solvent to form a first mixture, the solvent having a boiling point at a first temperature at a pressure of one atmosphere; and
   heating the first mixture to a second temperature and second pressure, the second temperature being higher than the first temperature and the second pressure being higher than one atmosphere, to form a second mixture comprising the cutin-derived monomers, oligomers, or combinations thereof.

2. The method of claim 1, further comprising separating the solvent from the cutin-derived monomers, oligomers, or combinations thereof in the second mixture to isolate the cutin-derived monomers, oligomers, or combinations thereof.

3. The method of claim 2, further comprising dissolving the isolated cutin-derived monomers, oligomers, or combinations thereof in a second solvent.

4. The method of claim 1, wherein at least a portion of the cutin-derived monomers, oligomers, or combinations thereof in the second mixture are unsaturated.

5. The method of claim 4, further comprising hydrogenating the unsaturated cutin-derived monomers, oligomers, or combinations thereof.

6. The method of claim 1, wherein a rate of depolymerization of the cutin in the solvent is at least 100 times greater at the second temperature and the second pressure than at the first temperature at one atmosphere.

7. The method of claim 1, wherein the second temperature is at least 393 K.

8. The method of claim 7, wherein the second pressure is greater than 5 atm.

9. The method of claim 8, wherein the first mixture is held at the second temperature and second pressure for at least about two hours.

10. The method of claim 7, wherein the second pressure is sufficiently high to maintain at least a portion of the solvent in a liquid phase at the second temperature.

11. The method of claim 1, wherein the solvent is selected from the group consisting of water, glycerol, methanol, ethanol, liquid $CO_2$, and supercritical $CO_2$.

12. The method of claim 1, wherein the solvent is substantially free of added acid or base.

13. The method of claim 1, wherein the process of forming the second mixture results in the production of both saturated and unsaturated fatty acids.

14. The method of claim 13, wherein a concentration of saturated fatty acids is higher than a concentration of unsaturated fatty acids in the second mixture.

15. The method of claim 1, wherein the process of forming the second mixture results in the production of both saturated and unsaturated fatty acid esters.

16. The method of claim 15, wherein a concentration of saturated fatty acid esters is higher than a concentration of unsaturated fatty acid esters in the second mixture.

17. The method of claim 1, wherein a depolymerization reaction at the second temperature results in the cutin-derived monomers, oligomers, or combinations thereof in the second mixture being uncharged.

18. A method of preparing cutin-derived monomers, oligomers, or combinations thereof from cutin-containing plant matter, comprising:
    obtaining cutin from the cutin-containing plant matter;
    adding the cutin to a solvent to form a first mixture, the solvent having a boiling point at a first temperature at a pressure of one atmosphere; and
    heating the first mixture to a second temperature and second pressure, the second temperature being higher than the first temperature and the second pressure being higher than one atmosphere, to form a second mixture comprising a first group of compounds of Formula I:

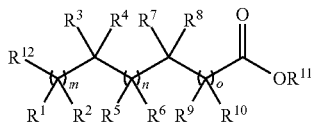

(Formula I)

wherein:
$R^1$, $R^2$, $R^3$, $R^4$, $R^5$, $R^6$, $R^7$, $R^8$, $R^9$, and $R^{10}$ are each independently —H, —$OR^{13}$, —$NR^{13}R^{14}$, —$SR^{13}$, halogen, —$C_1$-$C_6$ alkyl, —$C_1$-$C_6$ alkenyl, —$C_1$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{13}$, —$NR^{13}R^{14}$, —$SR^{13}$, or halogen;

$R^{13}$ and $R^{14}$ are each independently —H, —$C_1$-$C_6$ alkyl, —$C_1$-$C_6$ alkenyl, or —$C_1$-$C_6$ alkynyl;

$R^{11}$ is —H, -glyceryl, —$C_1$-$C_6$ alkyl, —$C_1$-$C_6$ alkenyl, —$C_1$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{13}$, —$NR^{13}R^{14}$, —$SR^{13}$, or halogen;

$R^{12}$ is —OH, —H, —$C_1$-$C_6$ alkyl, —$C_1$-$C_6$ alkenyl, —$C_1$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{13}$, —$NR^{13}R^{14}$, —$SR^{13}$, halogen, —COOH, or —$COOR^{11}$; and m, n, and o are each independently an integer in the range of 0 to 30, and 0≤m+n+o≤30.

19. The method of claim 18, wherein forming the second mixture further comprises producing compounds of Formula II:

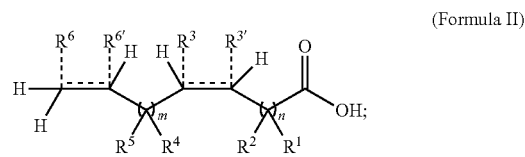

(Formula II)

wherein:
$R^1$, $R^2$, $R^4$ and $R^5$ are each independently —H, —$OR^{11}$, —$NR^{11}R^{12}$, —$SR^{11}$, halogen, —$C_1$-$C_6$ alkyl, —$C_1$-$C_6$ alkenyl, —$C_1$-$C_6$ alkynyl, —$C_3$-$C_7$ cycloalkyl, aryl, or 5- to 10-membered ring heteroaryl, wherein each alkyl, alkenyl, alkynyl, cycloalkyl, aryl, or heteroaryl is optionally substituted with —$OR^{11}$, —$NR^{11}R^{12}$, —$SR^{11}$, or halogen;

$R^{11}$ and $R^{12}$ are each independently —H, —$C_1$-$C_6$ alkyl, —$C_1$-$C_6$ alkenyl, or —$C_1$-$C_6$ alkynyl;

the symbol ===== represents an optionally single or cis or trans double bond;

$R^3$ is —OH and $R^{3'}$ is selected from the group consisting of —H, —$C_1$-$C_6$ alkyl, —$C_1$-$C_6$ alkenyl, —$C_1$-$C_6$ alkynyl, —$C_3$-$C_7$ cycloalkyl, and aryl when ===== between $R^3$ and $R^{3'}$ is a single bond, and $R^3$ and $R^{3'}$ are absent when ===== between $R^3$ and $R^{3'}$ represents a double bond;

$R^6$ is —OH and $R^{6'}$ is selected from the group consisting of —H, —$C_1$-$C_6$ alkyl, —$C_1$-$C_6$ alkenyl, —$C_1$-$C_6$ alkynyl, —$C_3$-$C_7$ cycloalkyl, and —$C_6$-$C_{10}$ aryl when ===== between $R^6$ and $R^{6'}$ is a single bond, and $R^6$ and $R^{6'}$ are absent when ===== between $R^6$ and $R^{6'}$ represents a double bond;

n is an integer in the range of 0 to 11;
m is an integer in the range of 0 to 25; and
0≤m+n≤25.

20. The method of claim 19, wherein a concentration of the compounds of Formula I is greater than a concentration of the compounds of Formula II in the second mixture.

21. The method of claim 19, wherein a concentration of the compounds of Formula II is greater than a concentration of the compounds of Formula I in the second mixture.

22. The method of claim 21, further comprising modifying the compounds of Formula II to form a second group of compounds of Formula I.

23. The method of claim 18, wherein forming the second mixture further comprises producing compounds of Formula III:

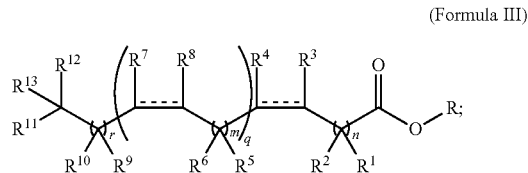

(Formula III)

wherein:
R¹, R², R⁵, R⁶, R⁹, R¹⁰, R¹¹, R¹² and R¹³ are each independently, at each occurrence, —H, —OR¹⁴, —NR¹⁴R¹⁵, —SR¹⁴, halogen, —C₁-C₆ alkyl, —C₂-C₆ alkenyl, —C₂-C₆ alkynyl, —C₃-C₇ cycloalkyl, aryl, or heteroaryl, wherein each alkyl, alkenyl, alkynyl, cycloalkyl, aryl, or heteroaryl is optionally substituted with one or more —OR¹⁴, —NR¹⁴R¹⁵, —SR¹⁴, or halogen;

R³, R⁴, R⁷, and R⁸ are each independently, at each occurrence, —H, —OR¹⁴, —NR¹⁴R¹⁵, —SR¹⁴, halogen, —C₁-C₆ alkyl, —C₂-C₆ alkenyl, —C₂-C₆ alkenyl, —C₂-C₆ alkynyl, —C₃-C₇ cycloalkyl, aryl, or heteroaryl wherein each alkyl, alkynyl, cycloalkyl, aryl, or heteroaryl is optionally substituted with one or more —OR¹⁴, —NR¹⁴R¹⁵, —SR¹⁴, or halogen; or R³ and R⁴ can combine with the carbon atoms to which they are attached to form a C₃-C₆ cycloalkyl, a C₄-C₆ cycloalkenyl, or 3- to 6-membered ring heterocycle; and/or R⁷ and R⁸ can combine with the carbon atoms to which they are attached to form a C₃-C₆ cycloalkyl, a C₄-C₆ cycloalkenyl, or 3- to 6-membered ring heterocycle;

R¹⁴ and R¹⁵ are each independently, at each occurrence, —H, —C₁-C₆ alkyl, —C₂-C₆ alkenyl, or —C₂-C₆ alkynyl;

the symbol ===== represents a single bond or a cis or trans double bond;

n is 0, 1, 2, 3, 4, 5, 6, 7 or 8;
m is 0, 1, 2 or 3;
q is 0, 1, 2, 3, 4 or 5; and
r is 0, 1, 2, 3, 4, 5, 6, 7 or 8; and
R is selected from —H, —C₁-C₆ alkyl, —C₂-C₆ alkenyl, —C₂-C₆ alkynyl, —C₃-C₇ cycloalkyl, aryl, 1-glycerol, 2-glycerol, or heteroaryl.

24. The method of claim 23, wherein a concentration of the compounds of Formula I is greater than a concentration of the compounds of Formula III in the second mixture.

25. The method of claim 23, wherein a concentration of the compounds of Formula III is greater than a concentration of the compounds of Formula I in the second mixture.

26. The method of claim 25, further comprising modifying the compounds of Formula III to form a second group of compounds of Formula I.

27. A method of preparing cutin-derived monomers, oligomers, or combinations thereof from cutin-containing plant matter, comprising:
obtaining cutin from the cutin-containing plant matter;
adding the cutin to a solvent to form a first mixture, the solvent having a boiling point at a first temperature at a pressure of one atmosphere; and
heating the first mixture to a second temperature and second pressure, the second temperature being higher than the first temperature and the second pressure being higher than one atmosphere, to form a second mixture comprising a first group of compounds of Formula III:

(Formula III)

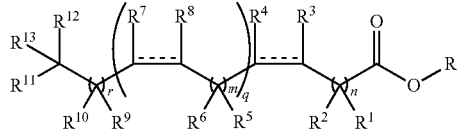

wherein:
R¹, R², R⁵, R⁶, R⁹, R¹⁰, R¹¹, R¹² and R¹³ are each independently, at each occurrence, —H, —OR¹⁴, —NR¹⁴R¹⁵, —SR¹⁴, halogen, —C₁-C₆ alkyl, —C₂-C₆ alkenyl, —C₂-C₆ alkynyl, —C₃-C₇ cycloalkyl, aryl, or heteroaryl, wherein each alkyl, alkenyl, alkynyl, cycloalkyl, aryl, or heteroaryl is optionally substituted with one or more —OR¹⁴, —NR¹⁴R¹⁵, —SR¹⁴, or halogen;

R³, R⁴, R⁷, and R⁸ are each independently, at each occurrence, —H, —OR¹⁴, —NR¹⁴R¹⁵, —SR¹⁴, halogen, —C₁-C₆ alkyl, —C₂-C₆ alkenyl, —C₂-C₆ alkenyl, —C₂-C₆ alkynyl, —C₃-C₇ cycloalkyl, aryl, or heteroaryl wherein each alkyl, alkynyl, cycloalkyl, aryl, or heteroaryl is optionally substituted with one or more —OR¹⁴, —NR¹⁴R¹⁵, —SR¹⁴, or halogen; or R³ and R⁴ can combine with the carbon atoms to which they are attached to form a C₃-C₆ cycloalkyl, a C₄-C₆ cycloalkenyl, or 3- to 6-membered ring heterocycle; and/or R⁷ and R⁸ can combine with the carbon atoms to which they are attached to form a C₃-C₆ cycloalkyl, a C₄-C₆ cycloalkenyl, or 3- to 6-membered ring heterocycle;

R¹⁴ and R¹⁵ are each independently, at each occurrence, —H, —C₁-C₆ alkyl, —C₂-C₆ alkenyl, or —C₂-C₆ alkynyl;

the symbol ===== represents a single bond or a cis or trans double bond;

n is 0, 1, 2, 3, 4, 5, 6, 7 or 8;
m is 0, 1, 2 or 3;
q is 0, 1, 2, 3, 4 or 5; and
r is 0, 1, 2, 3, 4, 5, 6, 7 or 8; and
R is selected from —H, —C₁-C₆ alkyl, —C₂-C₆ alkenyl, —C₂-C₆ alkynyl, —C₃-C₇ cycloalkyl, aryl, 1-glycerol, 2-glycerol, or heteroaryl.

28. The method of claim 27, further comprising modifying the compounds of Formula III to form compounds of Formula I:

(Formula I)

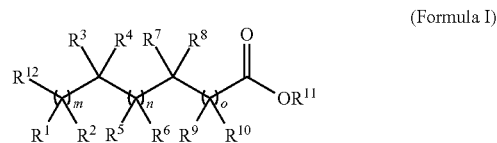

wherein:
R¹, R², R³, R⁴, R⁵, R⁶, R⁷, R⁸, R⁹, and R¹⁰ are each independently —H, —OR¹³, —NR¹³R¹⁴, —SR¹³, halogen, —C₁-C₆ alkyl, —C₁-C₆ alkenyl, —C₁-C₆ alkynyl, —C₃-C₇ cycloalkyl, aryl, or 5- to 10-membered ring heteroaryl, wherein each alkyl, alkenyl, alkynyl, cycloalkyl, aryl, or heteroaryl is optionally substituted with —OR¹³, —NR¹³R¹⁴, —SR¹³, or halogen;

R¹³ and R¹⁴ are each independently —H, —C₁-C₆ alkyl, —C₁-C₆ alkenyl, or —C₁-C₆ alkynyl;

R¹¹ is —H, -glyceryl, —C₁-C₆ alkyl, —C₁-C₆ alkenyl, —C₁-C₆ alkynyl, —C₃-C₇ cycloalkyl, aryl, or 5- to 10-membered ring heteroaryl, wherein each alkyl, alkenyl, alkynyl, cycloalkyl, aryl, or heteroaryl is optionally substituted with —OR¹³, —NR¹³R¹⁴, —SR¹³, or halogen;

R¹² is —OH, —H, —C₁-C₆ alkyl, —C₁-C₆ alkenyl, —C₁-C₆ alkynyl, —C₃-C₇ cycloalkyl, aryl, or 5- to 10-membered ring heteroaryl, wherein each alkyl, alkenyl, alkynyl, cycloalkyl, aryl, or heteroaryl is optionally substituted with —$OR^{13}$, —$NR^{13}R^{14}$, —$SR^{13}$, halogen, —COOH, or —$COOR^{11}$; and m, n, and o are each independently an integer in the range of 0 to 30, and 0≤m+n+o≤30.

29. A method of preparing cutin-derived monomers, oligomers, or combinations thereof from cutin-containing plant matter, comprising:

obtaining cutin from the cutin-containing plant matter;

adding the cutin to a solvent to form a first mixture; and heating the first mixture to a temperature of at least 498K and a pressure of at least 360 psi, thereby forming a second mixture comprising the cutin-derived monomers, oligomers, or combinations thereof.

30. The method of claim 29, wherein the first mixture is held at the temperature of at least 498K and the pressure of at least 360 psi for at least two hours.

* * * * *